(12) United States Patent
Jones et al.

(10) Patent No.: US 7,655,434 B2
(45) Date of Patent: Feb. 2, 2010

(54) LIVE-CELL BIOSENSOR POLYPEPTIDES AND METHODS OF USE

(75) Inventors: Joshua T. Jones, Salt Lake City, UT (US); Angela Teresa Hahn, Redwood City, CA (US); Tobias Meyer, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 609 days.

(21) Appl. No.: 11/052,001

(22) Filed: Feb. 3, 2005

(65) Prior Publication Data

US 2005/0233356 A1    Oct. 20, 2005

Related U.S. Application Data

(60) Provisional application No. 60/541,297, filed on Feb. 3, 2004.

(51) Int. Cl.
*C12Q 1/02* (2006.01)
*C12N 5/06* (2006.01)

(52) U.S. Cl. .................................... 435/29; 435/325

(58) Field of Classification Search ........................ None
See application file for complete search history.

(56) References Cited

U.S. PATENT DOCUMENTS

| | | | | |
|---|---|---|---|---|
| 6,225,636 | B1 * | 5/2001 | Ginestet | 250/458.1 |
| 7,090,976 | B2 * | 8/2006 | Anderson et al. | 435/6 |
| 2003/0032597 | A1 * | 2/2003 | Sebestyen | 514/12 |
| 2006/0247862 | A1 * | 11/2006 | Arini et al. | 702/19 |

OTHER PUBLICATIONS

Margalit A, Vlcek S, Gruenbaum Y, Foisner R. J Cell Biochem Jun. 1, 2005;95(3):454-65.*
BD Clontech ApoAlert™ pCaspase3-Sensor Vector, Clontechniques Apr. 2002.
Campbell et al., "A monomeric red fluorescent protein", PNAS 99(12):7877-7882.
Gu et al., "Cell cycle-dependent regulation of a human DNA helicase that localizes in DNA damage foci", MBC 15:3320-3332 (2004).
Gu et al., "Cell cycle-regulated subcellular localization of human DNA helicase B (HDHB) and its association with Mrell/Rad50/NBSI complex", JBC 14 Abstract 44 (2003).
Jones et al., "Probing the precision of the mitotic clock with a live-cell fluorescent biosensor", Nature Biotechnology, 22(3):306-312 (2004).
Jones et al., "Probing the precision of the mitotic clock with a live-cell fluorescent biosensor", Poster abstracts 207, Keystone Symposia, Cell Cycle and Development Jan. 6-11, 2004.
Leonhardt et al., "Dynamics of DNA replication factories in living cells", JCB 149(2):271-279 (2000).
Meyer, et al., "Probing the precision of the mitotic clock with. a live cell fluorescent biosensor", Annual meeting program, The American Society for Cell Biology, 43$^{rd}$ Annual Meeting, #1641, Dec. 13-17, 2003.
pCaspase3-Sensor Vector Information PT3649-5 (Clonetech Catalog #8185-1, 2002.
Rekas et al., "Crystal structure of venus, a yellow fluorescent protein with improved maturation and reduced environmental sensitivity", J. Biol. Chem. 50:573-578 (2002).
Taneja et al., "A dominant-negative mutant of human DNA helicase B blocks the onset of chromosomal DNA replication", JBC 277(43):40853-40861 (2002).
A Dissertation Submitted to the Department of Molecular Pharmacology and the Committee of Graduate Studies of Stanford University in Partial Fulfillment of the Requirements for the Degree of Doctor of Philosophy, Entitled "Using a live cell mitosis biosensor to probe mechanism of the mitotic clock: from single molecule to gene family studies", by Josha T. Jones, Nov. 2004.

* cited by examiner

*Primary Examiner*—Nancy Vogel
(74) *Attorney, Agent, or Firm*—Carol L. Francis; Bozicevic, Field & Francis, LLP

(57) ABSTRACT

Methods and compositions for determining the duration of a cell cycle phase of a mammalian cell, as well as identification of the cell cycle stage of fixed mammalian cells, are provided. In practicing the subject methods, at least one biosensor polypeptide that monitors a cell-cycle phase in a mammalian cell, such as mitosis, G1, S, or G2 phase, is used to determine the duration of a cell-cycle phase of a mammalian cell. Also provided are methods for identifying an agent (e.g., a gene product or small molecule compound) that modulates the duration of a cell-cycle phase of a mammalian cell, as well as kits and systems for practicing the subject methods.

18 Claims, 26 Drawing Sheets

FIG 10A

```
ATGGCTTCGTGGGGATCCCCGAAGAAGAAGCGCAAAGTACTGGTACCGGTCGCCACCATG
GTGAGCAAGGGCGAGGAGCTGTTCACCGGGGTGGTGCCCATCCTGGTCGAGCTGGACGGC
GACGTAAACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCCACCCTC
GTGACCACCTTCGGCTACGGCCTGCAGTGCTTCGCCCGCTACCCCGACCACATGAAGCAG
CACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGTG
AACCGCATCGAGCTGAAGGGCATCGACTTCAAGGAGGACGGCAACATCCTGGGGCACAAG
CTGGAGTACAACTACAACAGCCACAACGTCTATATCATGGCCGACAAGCAGAAGAACGGC
ATCAAGGTGAACTTCAAGATCCGCCACAACATCGAGGACGGCAGCGTGCAGCTCGCCGAC
CACTACCAGCAGAACACCCCCATCGGCGACGGCCCCGTGCTGCTGCCCGACAACCACTAC
CTGAGCTACCAGTCCGCCCTGAGCAAAGACCCCAACGAGAAGCGCGATCACATGGTCCTG
CTGGAGTTCGTGACCGCCGCCGGGATCACTCTCGGCATGGACGAGCTGTACAAGGGCGAA
GGGCAAGGGCAAGGGCAAGGGCCGGGCCGCGGCTACGCGTATCGATCCATGTTCGAGGCG
CGCCTGGTCCAGGGCTCCATCCTCAAGAAGGTGTTGGAGGCACTCAAGGACCTCATCAAC
GAGGCCTGCTGGGATATTAGCTCCAGCGGTGTAAACCTGCAGAGCATGGACTCGTCCCAC
GTCTCTTTGGTGCAGCTCACCCTGCGGTCTGAGGGCTTCGACACCTACCGCTGCGACCGC
AACCTGGCCATGGGCGTGAACCTCACCAGTATGTCCAAAATACTAAAATGCGCCGGCAAT
GAAGATATCATTACACTAAGGGCCGAAGATAACGCGGATACCTTGGCGCTAGTATTTGAA
GCACCAAACCAGGAGAAAGTTTCAGACTATGAAATGAAGTTGATGGATTTAGATGTTGAA
CAACTTGGAATTCCAGAACAGGAGTACAGCTGTGTAGTAAAGATGCCTTCTGGTGAATTT
GCACGTATATGCCGAGATCTCAGCCATATTGGAGATGCTGTTGTAATTTCCTGTGCAAAA
GACGGAGTGAAATTTCTGCAAGTGGAGAACTTGGAAATGGAAACATTAAATTGTCACAG
ACAAGTAATGTCGATAAGAGGAGGAAGCTGTTACCATAGAGATGAATGAACCAGTTCAA
CTAACTTTTGCACTGAGGTACCTGAACTTCTTTACAAAAGCCACTCCACTCTCTTCAACG
GTGACACTCAGTATGTCTGCAGATGTACCCCTTGTTGTAGAGTATAAAATTGCGGATATG
GGACACTTAAAATACTACTTGGCTCCCAAGATCGAGGATGAAGAAGGATCTTAG
```
(SEQ ID NO:03)

FIG. 10B

```
     NLS              GFP
MASWGSPKKKRKVLVPVATMSKGEELFTGVVPILVELDGDVNGHKFSVSGEGEGDATYG

KLTLKFICTTGKLPVPWPTLVTTFGYGLQCFARYPDHMKQHDFFKSAMPEGYVQERTIFF

KDDGNYKTRAEVKFEGDTLVNRIELKGIDFKEDGNILGHKLEYNYNSHNVYIMADKQKNG

IKVNFKIRHNIEDGSVQLADHYQQNTPIGDGPVLLPDNHYLSYQSALSKDPNEKRDHMVL
                Flexible Linker    Full Length PCNA
LEFVTAAGITLGMDELYKGEGQGQGQGPGRGYAYRSMFEARLVQGSILKKVLEALKDLIN

EACWDISSSGVNLQSMDSSHVSLVQLTLRSEGFDTYRCDRNLAMGVNLTSMSKILKCAGN

EDIITLRAEDNADTLALVFEAPNQEKVSDYEMKLMDLDVEQLGIPEQEYSCVVKMPSGEF

ARICRDLSHIGDAVVISCAKDGVKFSASGELGNGNIKLSQTSNVDKEEEAVTIEMNEPVQ

LTFALRYLNFFTKATPLSSTVTLSMSADVPLVVEYKIADMGHLKYYLAPKIEDEEGS
(SEQ ID NO:04)
```

FIG. 10C

```
CTCTCCTCTAGCGGCGCACCTCCAGCAGATTTTCCGTCCCCACGGAAGAGCTCTGGAGAC
AGTGGAGGACCCAGCACACCGTCAGCATCTCCACTCCCTGTAGTCACAGACCACGCCATG
ACAAATGATGTCACCTGGAGCGAGGCCTCTTCGCCTGATGAGAGGACACTCACCTTTGCT
GAAAGATGGCAATTATCTTCACCTGATGGAGTAGATACAGATGATGATTTACCAAAATCG
CGAGCATCCAAAAGAACCTGTGGTGTGAATGATGATGAAAGTCCAAGCAAAATTTTTATG
GTGGGAGAATCTCCACAAGTGTCTTCCAGACTTCAGAATTTGAGACTGAATAATTTAATT
CCCAGGCAACTTTTCAAGCCCACCGATAATCAAGAAACTCGGGGTACCGCCACCATGGTG
GCCTCCTCCGAGGACGTCATCAAAGAGTTCATGCGCTTCAAGGTGCGCATGGAGGGCTCC
GTGAACGGCCACGAGTTCGAGATCGAGGGCGAGGGCGAGGGCCGCCCCTACGAGGGCACC
CAGACCCCCAAGCTGAAGGTGACCAAGGGCGGCCCCTGCCCTTCGCCTGGGACATCCTG
TCCCCCCAGTTCCAGTACGGCTCCAAGGCGTACGTGAAGCACCCCGCCGACATCCCCGAC
TACAAGAAGCTGTCCTTCCCCGAGGGCTTCAAGTGGGAGCGCGTGATGAACTTCGAGGAC
GGCGGCGTGGTGACCGTGACCCAGGACTCCTCCCTGCAGGACGGCACGCTGATCTACAAG
GTGAAGTTCGCGGCACCAACTTCCCCCCCGACGGCCCCGTAATGCAGAAGAAGACCATG
GGCTGGGAGGCCTCCACCGAGCGCCTGTACCCCGCGACGGCGTGCTGAAGGGCGAGATC
CACCAGGCCCTGAAGCTGAAGGACGGCGGCCACTACCTGGTGGAGTTCAAGACCATCTAC
ATGGCCAAGAAGCCCGTGCAGCTGCCCGGCTACTACTACGTGGACACCAAGCTGCACATC
ACCTCCCACAACGAGGACTACACCATCGTGGAACAGTACGAGCGCTCCGAGGGCCGCCAC
CACCTGTTCCTGGGGCATGGCACCGGCAGCACCGGCAGCGGCAGCTCCGGCACCGCCTCC
TCCGAGGACGTCATCAAAGAGTTCATGCGCTTCAAGGTGCGCATGGAGGGCTCCGTGAAC
GGCCACGAGTTCGAGATCGAGGGCGAGGGCGAGGGCCGCCCCTACGAGGGCACCCAGACC
GCCAAGCTGAAGGTGACCAAGGGCGGCCCCCTGCCCTTCGCCTGGGACATCCTGTCCCCC
CAGTTCCAGTACGGCTCCAAGGCGTACGTGAAGCACCCCGCCGACATCCCCGACTACAAG
AAGCTGTCCTTCCCCGAGGGCTTCAAGTGGGAGCGCGTGATGAACTTCGAGGACGGCGGC
GTGGTGACCGTGACCCAGGACTCCTCCCTGCAGGACGGCACGCTGATCTACAAGGTGAAG
TTCGCGGCACCAACTTCCCCCCCGACGGCCCCGTAATGCAGAAGAAGACCATGGGCTGG
GAGGCCTCCACCGAGCGCCTGTACCCCGCGACGGCGTGCTGAAGGGCGAGATCCACCAG
GCCCTGAAGCTGAAGGACGGCGGCCACTACCTGGTGGAGTTCAAGACCATCTACATGGCC
AAGAAGCCCGTGCAGCTGCCCGGCTACTACTACGTGGACACCAAGCTGGACATCACCTCC
CACAACGAGGACTACACCATCGTGGAACAGTACGAGCGCTCCGAGGGCCGCCACCACCTG
TTCCTGTAG
```

(SEQ ID NO:05)

FIG. 10D

HDHB
LSSSGAPPADFPSPRKSSGDSGGPSTPSASPLPVVTDHAMTNDVTWSEASSPDERTLTFA

ERWQLSSPDGVDTDDDLPKSRASKRTCGVNDDESPSKIFMVGESPQVSSRLQNLRLNNLI

Red Fluorescent Protein (tdimer2)
PRQLFKPTDNQETRGTATMVASSEDVIKEFMRFKVRMEGSVNGHEFEIEGEGEGRPYEGT

QTAKLKVTKGGPLPFAWDILSPQFQYGSKAYVKHPADIPDYKKLSFPEGFKWERVMNFED

GGVVTVTQDSSLQDGTLIYKVKFRGTNFPPDGPVMQKKTMGWEASTERLYPRDGVLKGEI

HQALKLKDGGHYLVEFKTIYMAKKPVQLPGYYYVDTKLDITSHNEDYTIVEQYERSEGRH

HLFLGHGTGSTGSGSSGTASSEDVIKEFMRFKVRMEGSVNGHEFEIEGEGEGRPYEGTQT

AKLKVTKGGPLPFAWDILSPQFQYGSKAYVKHPADIPDYKKLSFPEGFKWERVMNFEDGG

VVTVTQDSSLQDGTLIYKVKFRGTNFPPDGPVMQKKTMGWEASTERLYPRDGVLKGEIHQ

ALKLKDGGHYLVEFKTIYMAKKPVQLPGYYYVDTKLDITSHNEDYTIVEQYERSEGRHHL

FL (SEQ ID NO:06)

FIG. 12
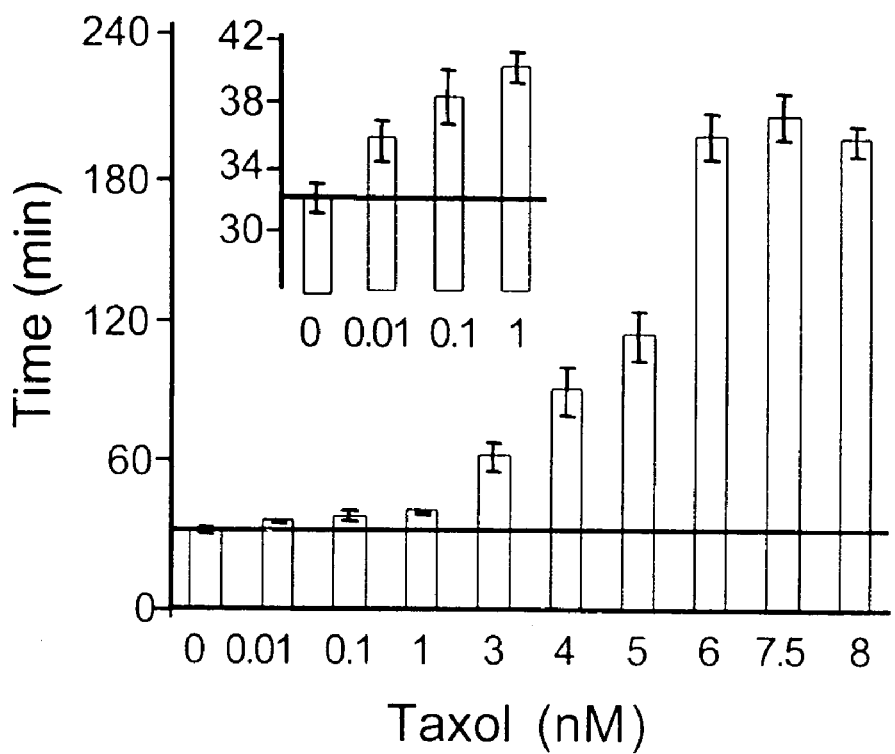
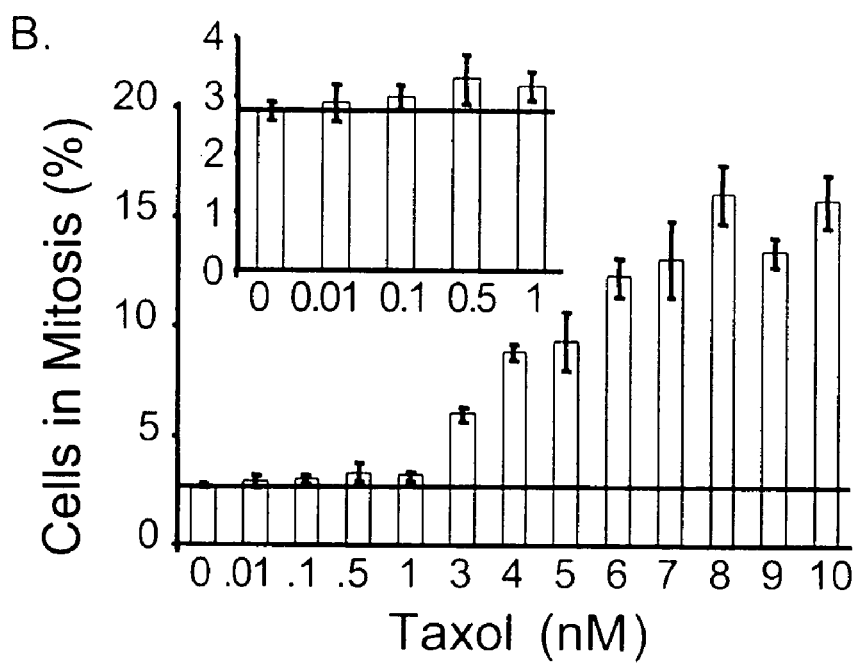

Figure 14A

TAGTTATTAATAGTA ATCAATTACGGGGTCAT TAGTTCATAGCCCATAT ATGGAGTTCCGCGTTAC ATA
ACTTACGGTAAATGG CCCGCCTGGCTGACCGC CCAACGACCCCCGCCCA TTGACGTCAATAATGAC GTA
TGTTCCCATAGTAAC GCCAATAGGGACTTTCC ATTGACGTCAATGGGTG GAGTATTTACGGTAAAC TGC
CCACTTGGCAGTACA TCAAGTGTATCATATGC CAAGTACGCCCCCTATT GACGTCAATGACGGTAA ATG
GCCCGCCTGGCATTA TGCCCAGTACATGACCT TATGGGACTTTCCTACT TGCAGTACATCTACGT ATT
AGTCATCGCTATTAC CATGGTGATGCGGTTTT GGCAGTACATCAATGGG CGTGGATAGCGGTTTGA CTC
ACGGGGATTTCCAAG TCTCCACCCCATTGACG TCAATGGGAGTTTGTTT GGCACCAAAATCAACG GGA
CTTTCCAAAATGTCG TAACAACTCCGCCCCAT TGACGCAAATGGGCGGT AGGCGTGTACGGTGGGA CGT
CTATATAAGCAGAGC TGGTTTAGTGAACCGTC AGATCCGCTAGCATGGA GAAAAAATCTAAGCCCA AAA
ACAGTGTATGGAAGA GGCTAAAATCACCATTC CGGAAGAAGAAAGATTC AGTAACTGGACCGGTCG CCA
CCATGGTGAGCAAGG GCGAGGAGCTGTTCACC GGGGTGGTGCCCATCCT GGTCGAGCTGGACGGCG ACG
TAAACGGCCACAAGT TCAGCGTGTCCGGCGAG GGCGAGGGCGATGCCAC CTACGGCAAGCTGACCC TGA
AGTTCATCTGCACCA CCGGCAAGCTGCCCGTG CCCTGGCCCACCCTCGT GACCACCTTCGCCTACG GCC
TGCAGTGCTTCGCCC GCTACCCCGACCACATG AAGCAGCACGACTTCTT CAAGTCCGCCATGCCCG AAG
GCTACGTCCAGGAGC GCACCATCTTCTTCAAG GACGACGGCAACTACAA GACCCGCGCCGAGGTGA AGT
TCGAGGGCGACACCC TGGTGAACCGCATCGAG CTGAAGGGCATCGACTT CAAGGAGGACGGCAACA TCC
TGGGGCACAAGCTGG AGTACAACTACAACAGC CACAACGTCTATATCAT GGCCGACAAGCAGAAGA ACG
GCATCAAGGTGAACT TCAAGATCCGCCACAAC ATCGAGGACGGCAGCGT GCAGCTCGCCGACCACT ACC
AGCAGAACACCCCCA TCGGCGACGGCCCCGTG CTGCTGCCCGACAACCA CTACCTGAGCTACCAGT CCG
CCCTGAGCAAAGACC CCAACGAGAAGCGCGAT CACATGGTCCTCCTGGA GTTCGTGACCGCCGCCG GA
TCACTCTCGGCATGG ACGAGCTGTACAAGTCC GGACTCAGATCTCGAGC TGATCCAAAAAAGAAGA GAA
AGGTAGATCCAAAAA AGAAGAGAAAGGTAGAT CCAAAAAAGAAGAGAAA GGTAGGATCCACCGGAT CTA
GATAACTGATCATAA TCAGCCATACCACATTT GTAGAGGTTTTACTTGC TTTAAAAAACCTCCCAC ACC
TCCCCCTGAACCTGA AACATAAAATGAATGCA ATTGTTGTTGTTAACTT GTTTATTGCAGCTTATA ATG
GTTACAAATAAAGCA ATAGCATCACAAATTTC ACAAATAAAGCATTTTT TTCACTGCATTCTAGTT GTG
GTTTGTCCAAACTCA TCAATGTATCTTAAGGC GTAAATTGTAAGCGTTA ATATTTTGTTAAAATTC GCG
TTAAATTTTTGTTAA ATCAGCTCATTTTTTAA CCAATAGGCCGAAATCG GCAAAATCCCTTATAAA TCA
AAAGAATAGACCGAG ATAGGGTTGAGTGTTGT TCCAGTTTGGAACAAGA GTCCACTATTAAAGAAC GTG
GACTCCAACGTCAAA GGGCGAAAAACCGTCTA TCAGGGCGATGGCCCAC TACGTGAACCATCACCC TAA
TCAAGTTTTTTGGGG TCGAGGTGCCGTAAAGC ACTAAATCGGAACCCTA AAGGGAGCCCCCGATTT AGA

Figure 14B

```
GCTTGACGGGGAAAG CCGGCGAACGTGGCGAG AAAGGAAGGGAAGAAAG CGAAAGGAGCGGGCGCT ACG
GCGCTGGCAAGTGTA GCGGTCACGCTGCGCGT AACCACCACACCCGCCG CGCTTAATGCGCCGCTA CAG
GGCGCGTCAGGTGGC ACTTTTCGGGGAAATGT GCGCGGAACCCCTATTT GTTTATTTTTCTAAATA CAT
TCAAATATGTATCCG CTCATGAGACAATAACC CTGATAAATGCTTCAAT AATATTGAAAAACGAAG AGT
CCTGAGGCGGAAAGA ACCAGCTGTGGAATGTG TGTCAGTTAGGGTGTGG AAAGTCCCCAGGCTCCC CAG
CAGGCAGAAGTATGC AAAGCATGCATCTCAAT TAGTCAGCAACCAGGTG TGGAAAGTCCCCAGGCT CCC
CAGCAGGCAGAAGTA TGCAAAGCATGCATCTC AATTAGTCAGCAACCAT AGTCCCGCCCCTAACTC CGC
CCATCCCGCCCCTAA CTCCGCCCAGTTCCGCC CATTCTCCGCCCCATGG CTGACTAATTTTTTTTA TTT
ATGCAGAGGCCGAGG CCGCCTCGGCCTCTGAG CTATTCCAGAAGTAGTG AGGAGGCTTTTTTGGAG GCC
TAGGCTTTTGCAAAG ATCGATCAAGAGACAGG ATGAGGATCGTTTCGCA TGATTGAACAAGATGGA TTG
CACGCAGGTTCTCCG GCCGCTTGGGTGGAGAG GCTATTCGGCTATGACT GGGCACAACAGACAATC GGC
TGCTCTGATGCCGCC GTGTTCCGGCTGTCAGC GCAGGGGCGCCCGGTTC TTTTTGTCAAGACCGAC CTG
TCCGGTGCCCTGAAT GAACTGCAAGACGAGGC AGCGCGGCTATCGTGGC TGGCCACGACGGGCGTT CCT
TGCGCAGCTGTGCTC GACGTTGTCACTGAAGC GGGAAGGGACTGGCTGC TATTGGGCGAAGTGCCG GGG
CAGGATCTCCTGTCA TCTCACCTTGCTCCTGC CGAGAAAGTATCCATCA TGGCTGATGCAATGCGG CGG
CTGCATACGCTTGAT CCGGCTACCTGCCCATT CGACCACCAAGCGAAAC ATCGCATCGAGCGAGCA CGT
ACTCGGATGGAAGCC GGTCTTGTCGATCAGGA TGATCTGGACGAAGAGC ATCAGCGGCTCGCGCCA GCC
GAACTGTTCGCCAGG CTCAAGGCGAGCATGCC CGACGGCGAGGATCTCG TCGTGACCCATGGCGAT GCC
TGCTTGCCGAATATC ATGGTGGAAAATGGCCG CTTTTCTGGATTCATCG ACTGTGGCCGGCTGGGT GTG
GCGGACCGCTATCAG GACATAGCGTTGGCTAC CCGTGATATTGCTGAAG AGCTTGGCGGCGAATGG GCT
GACCGCTTCCTCGTG CTTTACGGTATCGCCGC TCCCGATTCGCAGCGCA TCGCCTTCTATCGCCTT CTT
GACGAGTTCTTCTGA GCGGGACTCTGGGGTTC GAAATGACCGACCAAGC GACGCCCAACCTGCCAT CAC
GAGATTTCGATTCCA CCGCCGCCTTCTATGAA AGGTTGGGCTTCGGAAT CGTTTTCCGGGACGCCG GCT
GGATGATCCTCCAGC GCGGGATCTCATGCTG GAGTTCTTCGCCCACCC TAGGGGGAGGCTAACTG AAA
CACGGAAGGAGACAA TACCGGAAGGAACCCGC GCTATGACGGCAATAAA AAGACAGAATAAAACGC ACG
GTGTTGGGTCGTTTG TTCATAAACGCGGGGTT CGGTCCCAGGGCTGGCA CTCTGTCGATACCCCAC CGA
GACCCCATTGGGGCC AATACGCCCGCGTTTCT TCCTTTTCCCCACCCCA CCCCCAAGTTCGGGTG AAG
GCCCAGGGCTCGCAG CCAACGTCGGGGCGGCA GGCCCTGCCATAGCCTC AGGTTACTCATATATAC TTT
AGATTGATTTAAAAC TTCATTTTTAATTTAAA AGGATCTAGGTGAAGAT CCTTTTTGATAATCTCA TGA
CCAAAATCCCTTAAC GTGAGTTTTCGTTCCAC TGAGCGTCAGACCCCGT AGAAAGATCAAAGGAT CTT
CTTGAGATCCTTTTT TTCTGCGCGTAATCTGC TGCTTGCAAACAAAAAA ACCACCGCTACCAGCCG TGG
```

Figure 14C

```
TTTGTTTGCCGGATCAAGAGCTACCAACTCTTTTTCCGAAGGTAACTGGCTTCAGCAGACCGCAGAT
ACCAAATACTGTCCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGGGGGGTTCGTGCAC
ACAGCCCAGCTTGGAGCGAACGACCTACACCGAACTGAGATACCTACAGCGTGAGCTATGAGAAAGC
GCCACGCTTCCCGAAGGGAGAAAGGCGGACAGGTATCCGGTAAGCGGCAGGGTCGGAACAGGAGAGC
GCACGAGGGAGCTTCCAGGGGGAAACGCCTGGTATCTTTATAGTCCTGTCGGGTTTCGCCACCTCTG
ACTTGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCCCTG
ATTCTGTGGATAACCGTATTACCGCCATGCAT
```
(SEQ ID NO.:01)
(Underlined sequence: SEQ ID NO.:16)

Figure 14D

Polybasic Plasma Membrane Targeting Domain      EYFP

MEKKSKPKNSVWKRLKSPFRKKKDSVTGPVATMVSKGEELFTGVVPILVELD

GDVNGHKFSVSGEGEGDATYGKLTLKFICTTGKLPVPWPTLVTTFGYGLQCF

ARYPDHMKQHDFFKSAMPEGYVQERTIFFKDDGNYKTRAEVKFEGDTLVNRI

ELKGIDFKEDGNILGHKLEYNYNSHNVYIMADKQKNGIKVNFKIRHNIEDGS

VQLADHYQQNTPIGDGPVLLPDNHYLSYQSALSKDPNEKRDHMVLLEFVTAA

Nuclear Localization Signal

GITLGMDELYKSGLRSRADPKKKRKVDPKKKRKVDPKKKRKVGSTGSR (SEQ ID NO.:02)

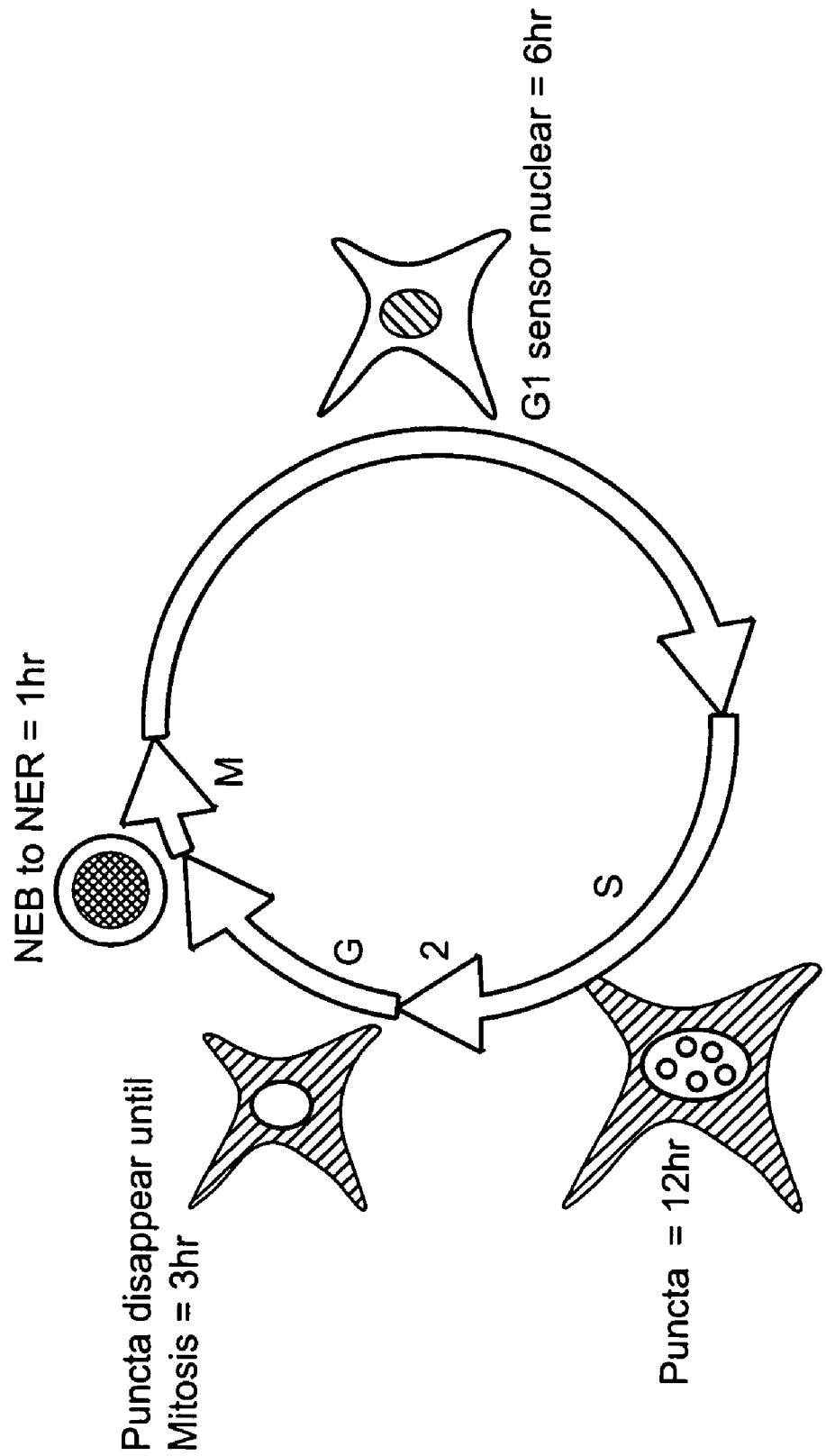

FIG. 17A
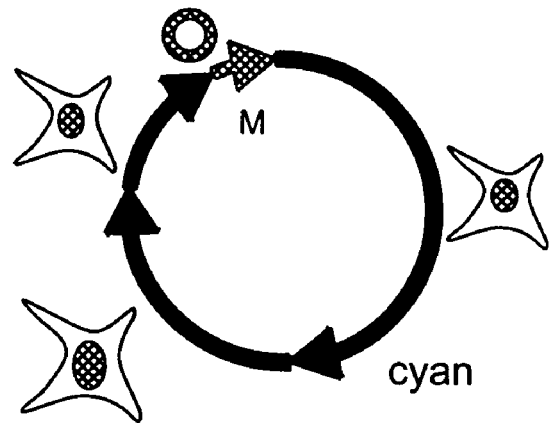
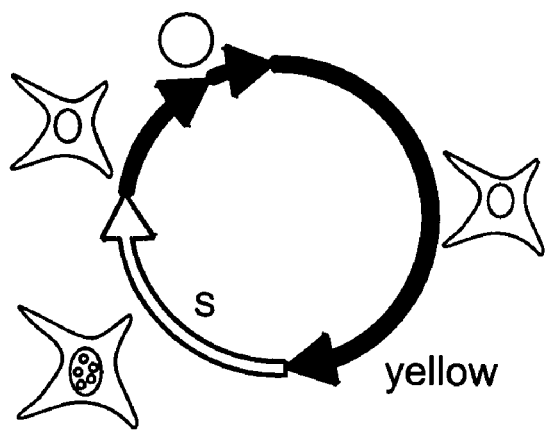
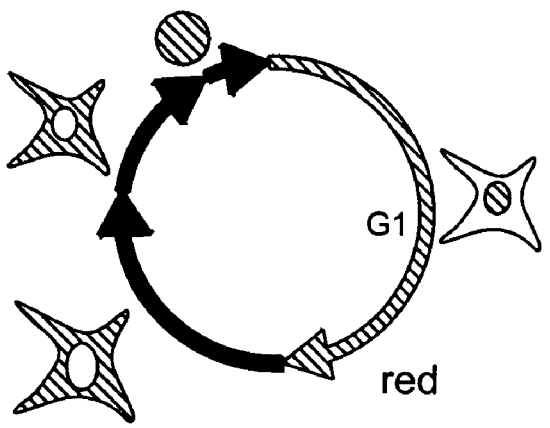

LIVE-CELL BIOSENSOR POLYPEPTIDES AND METHODS OF USE

CROSS-REFERENCE TO RELATED APPLICATIONS

This application claims the benefit of U.S. Provisional Application No. 60/541,297, filed Feb. 3, 2004, which application is incorporated herein by reference in its entirety.

GOVERNMENT RIGHTS

This invention was made with Government support under contract CA083229 awarded by the National Institutes of Health. The United States Government has certain rights in this invention.

BACKGROUND OF THE INVENTION

Progression through the cell cycle is the result of a highly regulated series of events in four defined phases. In the DNA synthesis phase (the S phase) the cell duplicates its DNA, which is followed by a gap phase (the G2 phase) in which the cell grows and prepares itself for mitosis. During mitosis (M phase) the cell divides its DNA and all of its contents into two separate daughter cells. Another gap phase (the G1 phase) follows mitosis and precedes the S phase. During the G1 phase cellular components are checked for repair, including DNA, prior to progressing into S phase. The majority of variability in the timing of the cell cycle is accounted for by differences in the rate of passage through G1. Progression though G1 is primarily dependent upon receiving and processing external and internal signals, as well as monitoring of cellular activity. The other cell cycle phases are generally autonomously programmed events, which while normally insulated from extracellular growth signals, are still susceptible to the misregulation of proteins disrupting the checkpoints within the cell cycle phase.

Since cell duplication relies on accurate chromosome separation, mitosis is thought to be one of the most tightly regulated cellular processes. Cells have solved the fidelity problem in part by relying on a sequential processing strategy that involves timing of individual cell cycle steps and on checkpoints that monitor the completion of different cell cycle phases (Ekholm et al., Mol. Cell. Biol. 21, 3256-65 (2001); Elledge et al., Science 274, 1664-72 (1996)). For example, during mitosis, the spindle checkpoint ensures the correct alignment and spindle attachment of sister chromatids (Musacchio et al., Nature Rev. Mol. Cell Biol. 3, 731-41 (2002); Yu, Curr. Opin. Cell Biol. 14, 706-714 (2002)). Failures at this critical checkpoint lead to genetic instability, which is a hallmark of cancer and is correlated with aggressive tumor behavior (e.g., unregulated cellular proliferation).

Techniques such as immunohistochemistry and FACS analysis have provided valuable information for understanding cell-cycle events. However, since these methods provide snapshots of single cells that are usually synchronized (e.g., arrested at the same cell cycle phase prior to analysis), temporal resolution of specific cell cycle phases (e.g., mitosis) at the single cell level is difficult. Phase contrast, differential interference contrast (DIC) or fluorescence imaging of live mitotic cells eliminates some of these problems, and has been used to measure mitotic times of individual cells. Nevertheless, observing mitotic timing in statistically significant cell numbers remains a challenge.

Accordingly, there remains a need in this art for systems and methods for monitoring cell cycle events, including methods for screening agents for use in treating cell cycle associated diseases, such as cancer. The present invention addresses this need.

RELEVANT LITERATURE

Jones et al., Nature Biotechnology, 22(3):306-312 (2004); Gu et al., MBC 15:3320-3332 (2004); Taneja et al., JBC 277(43):40853-40861 (2002); Campbell et al., PNAS 99(12): 7877-7882; Leonhardt et al., JCB 149(2):271-279 (2000); Gu et al., JBC 14 Abstract 44 (2003); Rekas et al., J. Biol. Chem. 50:573-578 (2002); pCaspase3-Sensor Vector Information PT3649-5 (Clonetech Catalog #8185-1; BD Clontech ApoA-lert™ pCaspase3-Sensor Vector, Clontechniques April 2002.

SUMMARY OF THE INVENTION

Methods and compositions for determining the duration of a cell cycle phase of a mammalian cell, as well as identification of the cell cycle stage of fixed mammalian cells are provided. In practicing the subject methods, at least one biosensor polypeptide that provides a fluorescence pattern indicative of a cell-cycle phase such as mitosis, G1, S, or G2 phase is introduced into a mammalian cell, and the fluorescence pattern analyzed to, for example, determine the duration of a cell-cycle phase of a live mammalian cell or to establish or identify the cell cycle stage of a fixed mammalian cell. Also provided are method for identifying an agent (e.g., a gene product or small molecule compound) that modulates the duration of a cell cycle phase of a mammalian cell, as well as kits and systems for practicing the subject methods.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 10A shows the nucleic acid sequence for an exemplary SBP of the invention (SEQ ID NO.:03).

FIG. 10B is the amino acid sequence predicted from translation of the nucleic acid sequence for the SBP (SEQ ID NO.:04) as shown in FIG. 10A.

FIG. 10C shows the nucleic acid sequence for an exemplary G1BP of the invention (SEQ ID NO.:05).

FIG. 10D is the amino acid sequence predicted from translation of the nucleic acid sequence for the G1BP (SEQ ID NO.:06) as shown in FIG. 10C.

FIG. 12 are a series of graphs showing the effect of the cancer therapeutic TAXOL™ on mitotic timing. In Panel A, TAXOL™ was added at the stated dose to the perfusion media and cells were monitored as described in FIG. 4, Panels A-B. Panel A shows a plot of the average time between NEB and NER with the black line representing the average time in between NEB and NER of untreated cells. The inset is a plot of the lower concentrations of TAXOL™ studied. Panel B shows TAXOL™ concentration dependence for mitotic arrest. The black line represents the percentage of mitotic cells in untreated cells. The inset is a plot of the lower concentrations of TAXOL™ studied. See Table 2 for detailed analysis.

FIGS. 14A-14C show the nucleic acid sequence for an exemplary MBP of the invention, pFMB-EYFP (SEQ ID NO.:01). The coding sequence for MBP is represented in underlined typeface (SEQ ID NO:16).

FIG. 14D is the amino acid sequence predicted from translation of the nucleic acid sequence for MBP (SEQ ID NO.:02) as shown in FIGS. 8A-8C in underlined typeface.

FIG. 16 is a schematic showing the estimated duration the cell cycle phases using G1BP and SBP. The time when the daughter cells form nuclear envelopes until the G1 sensor translocates to the cytoplasm is measured as G1. During this time no puncta appear in the S phase sensor fluorescence. After the translocation of the G1 sensor, the S phase sensor forms puncta. The formation and persistence of these puncta mark S phase. When these puncta disappear, the cell has entered G2. Nuclear envelope breakdown (NEB) signals the start of M phase (which includes mitosis and cytokinesis) which endures until nuclear envelope reformation (NER), signaling the start of G1 in the two daughter cells.

FIG. 17A is a schematic of the location of the biosensor polypeptides during the four phases of the cell cycle. The MBP, top, contains the cyan fluorescent protein (CFP). The MBP remains in the nucleus until nuclear envelope breakdown (NEB) during mitosis (M) after which the MBP translocates to the plasma membrane. The SBP, middle, containing the fluorescent protein (YFP) is diffuse in the nucleus in G1 and G2, punctate in the nucleus in S phase, and located throughout the cell during M phase. The G1BP, bottom, containing a red fluorescent protein (tdimer2) is located throughout the cell during M phase, and is nuclear during G1, but is cytoplasmic during S and G2.

DEFINITIONS

Figure 1:
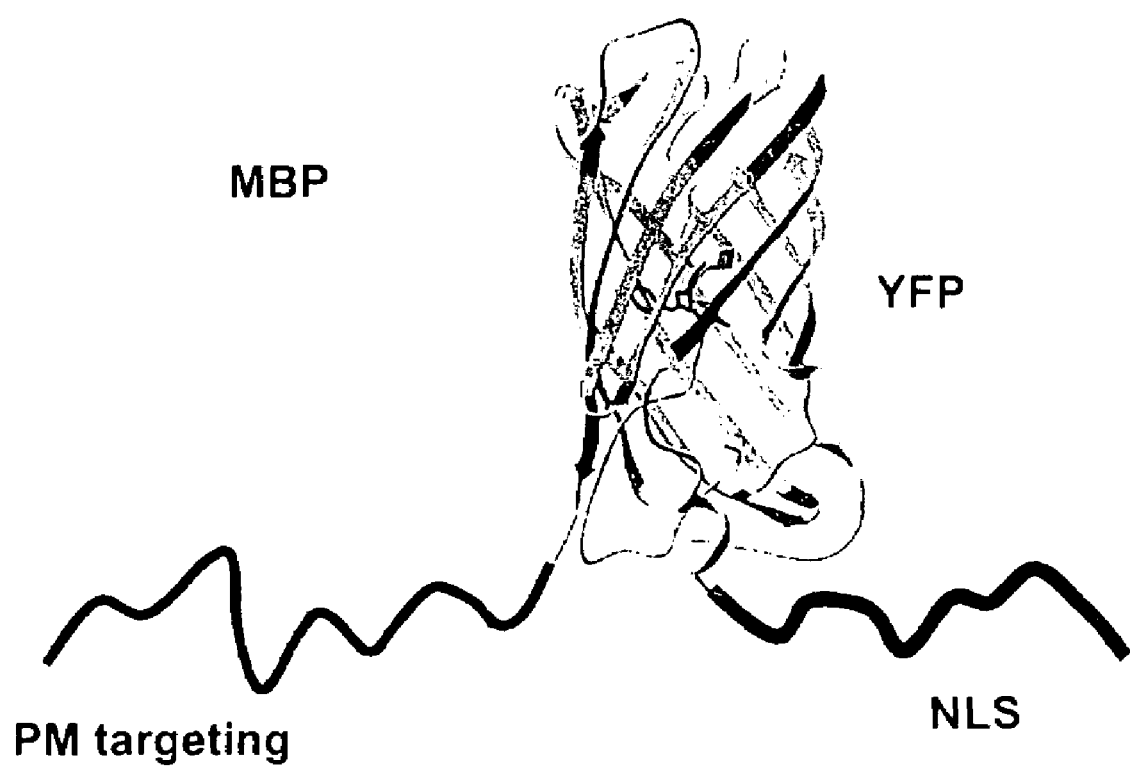
FIG. 1 shows a schematic of an exemplary fluorescent mitosis biosensor polypeptide. A plasma membrane (PM) targeting motif (exemplified by a polypeptide composed of polybasic residues) was added at the N-terminus of a fluorescent polypeptide (exemplified by yellow fluorescent protein (YFP)) fused to a nuclear localization signal (NLS).

Unless defined otherwise, all technical and scientific terms used herein have the same meaning as commonly understood by those of ordinary skill in the art to which this invention pertains. Any methods and materials similar or equivalent to those described herein can be used in the practice or testing of the present invention, the described methods and materials being exemplary.

As used herein "cell cycle" refers to the series of events involving the growth, replication, and division of a eukaryotic cell. A "phase of a cell cycle" or "cell cycle phase" refers to a distinct phase or period of the cell cycle, such as the mitosis phase (M phase), the first gap phase (G1 phase), the DNA synthesis phase (S phase), and the second gap phase (G2 phase). A "complete cell cycle" refers to entire single cell cycle including a G1 phase, S phase, G2 phase, and an M phase. Analysis of a complete cell cycle does not require beginning at a particular phase within the cell cycle. For example, a "complete cell cycle phase" may begin with an S phase and end at completion of G1 phase, or likewise, a "complete cell cycle phase" may begin with an M phase and end with completion of G2 phase.

The term "agent" includes any substance, molecule, element, compound, entity, or a combination thereof. It includes, but is not limited to, e.g., proteins (including antibodies), oligopeptides, small organic molecules, polysaccharides, polynucleotides (e.g., DNA or RNA, including polynucleotides encoding a gene product of interest, or which act as a cell modulator without transcription or without translation), and the like. It can be a natural product, a synthetic compound, or a chemical compound, or a combination of two or more substances. Unless otherwise specified, the terms "agent," "substance," and "compound" can be used interchangeably.

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

The term "biological preparation" refers to biological samples taken in vivo or in vitro (either with or without subsequent manipulation), as well as those prepared synthetically. Representative examples of biological preparations include cells, tissues, solutions and bodily fluids, lysates of natural or recombinant cells, and samples derived from such sources.

As used herein, the term "functional derivative" of a native protein or a polypeptide is used to define biologically active amino acid sequence variants that possess the biological activities (either functional or structural) that are substantially similar to those of the reference protein or polypeptide.

The terms "substantially pure" or "isolated," when referring to proteins and polypeptides denote those polypeptides that are separated from proteins or other contaminants with which they are naturally associated. A protein or polypeptide is considered substantially pure when that protein makes up greater than about 50% of the total protein content of the composition containing that protein; and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

The terms "nucleic acid molecule" and "polynucleotide" are used interchangeably and refer to a polymeric form of nucleotides of any length, either deoxyribonucleotides or ribonucleotides, or analogs thereof Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

As used herein, "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "recombinant" when used with reference to a cell indicates that the cell replicates a heterologous nucleic acid, or expresses a peptide or protein encoded by such a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence", "heterologous nucleic acid", "heterologous polypeptide" or "heterologous amino acid sequence" as used herein, is one that originates from a source foreign to the particular host cell, or, if from the same source, is modified from its original form. Thus, a heterologous nucleic acid in a host cell includes nucleic acid that, although being endogenous to the particular host cell, has been modified (e.g., so that it encodes an amino acid sequence different from that of the endogenous nucleic acid, to a nucleic acid to provide a sequence not normally found in the host cell, and the like). Modification of the heterologous sequence can occur, e.g., by treating the DNA with a restriction enzyme to generate a DNA fragment that is capable of being operably linked to the promoter or by operably linking the DNA to a heterologous promoter to provide an expression cassette that is not endogenous to the host cell. Techniques such as site-directed mutagenesis are also useful for modifying a heterologous nucleic acid.

The term "operably linked" refers to functional linkage between nucleic acids to provide a desired activity, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide (e.g., a nuclear localization signal is operably linked to a heterologous amino acid sequence to provide to association of the fusion protein with the nucleus in a mammalian cell).

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

As used herein, "contacting" has its normal meaning and refers to combining two or more entities (e.g., two proteins, a polynucleotide and a cell, a cell and a candidate agent, etc.). Contacting can occur in vitro (e.g., two or more agents [e.g., a test compound and a cell lysate] are combined in a test tube or other container) or in situ (e.g., two polypeptides can be contacted in a cell by coexpression in the cell, of recombinant polynucleotides encoding the two polypeptides), in a cell lysate.

By "genetic transformation" is meant a permanent or transient genetic change induced in a cell following incorporation of exogenous nucleic acid (e.g., DNA or RNA exogenous to the cell). Genetic change can be accomplished by, for example, incorporation of exogenous DNA into the genome of a host cell, by transient or stable maintenance of the exogenous DNA as an episomal element, or by transient introduction of an exogenous RNA into the host cell. Where the cell is a mammalian cell, a permanent genetic change is generally achieved by introduction of the DNA into the genome of the cell.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as CD4+ cells, T lymphocytes, macrophages, peripheral blood mononuclear cells (PBMC), and the like. The term "biological sample" encompasses a clinical sample, and also includes cells in culture, cell supernatants, tissue samples, organs, bone marrow, and the like.

DETAILED DESCRIPTION OF THE INVENTION

Methods and compositions for determining the duration of a cell cycle phase of a mammalian cell, as well as identification of the cell cycle stage of fixed mammalian cells are provided. In practicing the subject methods, at least one biosensor polypeptide that provides a fluorescence pattern indicative of a cell-cycle phase such as mitosis, G1, S, or G2 phase is introduced into a mammalian cell, and the fluorescence pattern analyzed to, for example, determine the duration of a cell-cycle phase of a live mammalian cell or to establish or identify the cell cycle stage of a fixed mammalian cell. Also provided are methods for identifying an agent (e.g., a gene product or small molecule compound) that modulates the duration of a cell-cycle phase of a mammalian cell, as well as kits and systems for practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the biosensor" includes reference to one or more biosensor and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Various biochemical and molecular biology methods referred to herein are well known in the art, and are described in, for example, Sambrook et al., Molecular Cloning: A Laboratory Manual, Cold Spring Harbor Press, N.Y. Second (1989) and Third (2000) Editions, and Current Protocols in Molecular Biology, (Ausubel, F. M. et al., eds.) John Wiley & Sons, Inc., New York (1987-1999).

OVERVIEW OF THE INVENTION

The present invention provides methods and compositions for monitoring one or more cell cycle phases, and for determining the duration of a cell cycle phase of a mammalian cell. While use of the methods and compositions of the invention find particular use in live mammalian cells, the methods of the invention can also be adapted to determine the cell cycle stage of a fixed mammalian cell. As provided in greater detail below, the subject methods of the present invention are practiced using at least one biosensor polypeptide that provides a fluorescent pattern indicative of one or more mammalian cell-cycle phases, such as M, G1, S, or G2. Monitoring of the fluorescence pattern of the one or more biosensors can be used to determine the duration of one or more cell-cycle phases. Accordingly, the subject methods can be used for identifying an agent (e.g., a gene product or small molecule compound) that modulates the duration of a cell-cycle phase of a mammalian cell, particularly a live mammalian cell.

The methods of the present invention are premised on the use of one or more genetically encoded biosensor polypeptide that can be used to directly monitor one ore more cell cycle phases. In general, the biosensor polypeptides described herein each contain a fluorescent polypeptide linked to a cell cycle phase polypeptide which contains amino acid sequences to target the fluorescence to different cellular locations depending on the specific cell cycle phase in which the cell resides. As a result, distinct fluorescence patterns associated with each biosensor polypeptide and cell cycle phase are generated.

For example, in one embodiment the mitosis biosensor polypeptide (MBP) contains a fluorescent polypeptide operably linked to a transmembrane spanning domain (e.g., a plasma membrane targeting domain) and a nuclear localization signal (NLS). As a result, the NLS of the MBP provides for localization of the MBP at the nuclear membrane until nuclear envelope breakdown (NEB) occurs at the beginning of the mitosis phase of the cell cycle. Thus, during interphase (G1/S/G2) MBP is contained within the nucleus. After NEB, the MBP is localized at the plasma membrane, indicating the cell is in mitosis. Upon nuclear envelope reformation (NER) at the end of the mitosis phase, the MBP is localized in the nucleus once again, indicating the cell is in interphase. Accordingly, this localization pattern results in a MBP fluorescence pattern that is indicative of a cell cycle phase (e.g., mitosis or interphase). Further, the MBP can be used to monitor live cells to determine the time of onset and ending of mitosis and interphase, as well as stages of mitosis (e.g., prometaphase).

The biosensor polypeptides of the subject invention can be used individually to monitor progression of a single cell-cycle phase. Alternatively, two or more, including all three, biosensor polypeptides described herein can be used in the same cell to measure the duration, either quantitatively or qualitatively, of different or distinct cell cycle phases, as well as determine which phase the cell is in at any one point in time. Accordingly, in some embodiments, the MBP may be used in conjunction with S phase biosensor polypeptide (SBP) and/or a G1 phase biosensor polypeptide (G1BP). In such embodiments, the SBP fluorescence patterns resulting from SBP localization during the cell cycle, as well as the G1BP fluorescence patterns resulting from G1BP localization during the cell cycle, are used with the MBP fluorescence patterns to determine which phase the cell is in at any one point in time or to measure the duration, either quantitatively or qualitatively, of different or distinct cell cycle phases of the cell.

The methods of the subject invention are simple and rapid to perform. The methods provide a highly sensitive and specific assay, allowing quantitative and qualitative determination of the cell cycle phase of a fixed mammalian cell, as well as allowing quantitative and qualitative determination of the duration of a cell cycle in a live mammalian cell. Importantly, the methods of the invention provide for determination of the duration of a cell cycle or a cell cycle phase in live cells without the need for synchronizing the cell cycle phase of the cells (e.g., by serum starving the cells in order to arrest cellular division), measuring DNA content, or the need for antibody staining of proteins expressed during specific cell cycle phases. This assay not only offers a powerful tool to dissect cell cycle phases, but can also be used to identify new modulators of cell cycle phases, such as a small molecule or an endogenous gene product, as well as providing valuable information on the toxicity of known and unknown modulators of cell cycle phases.

The following description provides guidance for making and using the compositions of the invention, and for carrying out the methods of the invention.

Biosensor Polypeptides

In general, cell cycle biosensor polypeptides of the present invention are fusion proteins comprising: 1) a fluorescent polypeptide domain; and 2) one of more subcellular targeting domains. The subcellular targeting domain enables the biosensor polypeptide to localize to specific regions of the cell during the cell cycle while the fluorescent polypeptide portion enables rapid detection of the biosensor polypeptide. Accordingly, following expression of the biosensor polypeptide, the localization pattern of the biosensor polypeptide can be detected, either quantitative or qualitatively, by detecting the fluorescence pattern of the polypeptide within the cell during a cell cycle, wherein the fluorescence pattern of the biosensor polypeptide is indicative of a cell cycle phase.

Any fluorescent polypeptide (also referred to herein as a fluorescent label) well known in the art is suitable for use as a domain of the subject biosensor polypeptides of the present invention. A suitable fluorescent polypeptide will be one that can be expressed in a desired host cell, such as a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

In some embodiments where multiple biosensor polypeptides are present in a cell, the fluorescent polypeptide of the biosensor is selected so that each biosensor polypeptide in the cell has a detectably different emission spectrum. For example, in such embodiments, the G1BP fluorescent label, the SBP fluorescent label, and the MBP fluorescent label, when present in the same cell, are designed to have detectably distinct emission spectra to facilitate detection of a distinct signal from each biosensor (e.g., through use of different filters in the imaging system).

Furthermore, in such embodiments where multiple biosensor polypeptides are present in a cell, the subcellular targeting domain is selected so that each biosensor polypeptide in the cell has a different localization pattern associated with the cell cycle. For example, in such embodiments, the G1BP targeting domain, the SBP targeting domain, and the MBP targeting domain when present in the same cell are designed to have detectably distinct targeting patters to facilitate detection of a distinct localizing pattern for each biosensor during the cell cycle.

The cell cycle biosensor polypeptides are described in more detail below.

Mitosis Biosensor Polypeptide

The mitosis biosensor polypeptide (MBP) of the present invention is a fusion polypeptide comprising: 1) a first reversible subcellular target associating domain (e.g., a domain which facilitates association of the MBP with a plasma membrane (PM) and condensed chromatin), 2) a fluorescent polypeptide domain, and 3) a second reversible subcellular target binding domain (e.g., a nuclear localization signal).

In representative embodiments, the MBP of the present invention is represented by the formula:

X—F—N wherein

X is a first reversible subcellular target associating domain selected from a reversible subcellular target associating domain (e.g., plasma membrane (PM) and condensed chromatin associating domain) or a nuclear localization signal (NLS);

F is a fluorescent polypeptide domain; and

N is a second reversible subcellular target binding domain selected from a reversible subcellular target associating domain (e.g., plasma membrane (PM) and condensed chromatin associating domain) or a nuclear localization signal (NLS);

wherein X and N are selected so that the MBP comprises at least one reversible subcellular target associating domain (e.g., PM and condensed chromatin associating domain) and at least one NLS.

The present invention thus contemplates MBPs comprising, in order from N- to C-terminus, a reversible subcellular target associating domain (e.g., PM and condensed chromatin associating domain), a fluorescent domain, and a NLS, as well as a MBPs comprising, in order from N- to C-terminus, an NLS, a fluorescent domain, and a reversible subcellular target associating domain (e.g., PM and condensed chromatin associating domain).

In one embodiment, the first reversible subcellular target associating domain (X) is a polypeptide encoding a membrane associating domain that enables predominant association with the plasma membrane and condensed chromatin (e.g., a plasma membrane targeting domain) and the second reversible subcellular target binding domain (N) is a nuclear localization signal (NLS).

Membrane associating domains can be selected from any amino acid sequence that provides for association of the biosensor with a cellular membrane, particularly a plasma membrane. As used herein a "membrane associating domains" also refers to a domain that provides for localization of the MBP to the condensed chromatin of the mammalian cell. In general, membrane associating domains facilitate specific or non-specific localization of a polypeptide with a plasma membrane and condensed chromatin, e.g., through charge-based interaction with plasma membrane and condensed chromatin components due to the presence of polar and/or positively-charged amino acid residues (e.g., tryptophan, lysine, arginine, and the like). An exemplary plasma membrane targeting domain is that of the C-terminus of the plasma membrane targeting sequence of small GTPase Ras-like protein (Rit). A representative sequence of the plasma membrane targeting domain is provided in SEQ ID NO:07, with the minimal sequence for providing targeting to the plasma membrane provided in SEQ ID NO:08. In one embodiment, the membrane association domain contains an amino acid sequence of about 20, 21, 22, 24, 26, 28, or more amino acids, which amino acid sequence is of the formula:

$\underline{Z_1Z_2}XZ_3XZ_4XXXZ_5\underline{Z_6Z_7}XZ_8XXXZ_9\underline{Z_{10}Z_{11}Z_{12}}$   (SEQ ID NO.:17)

Wherein Z is a polar or charged residue selected from lysine (K), tryptophan (W), arginine (R), and the like. In some embodiments, $Z_{1-4, 6-12}$ are positively charged residues, such as lysine, (L), arginine (R), aspartic acid (D), glutamic acid (E), and histidine (H), and $Z_5$ is a polar reside, such as tryptophan (W).

In another embodiment, the membrane association domain comprises the amino acid sequence exemplified in SEQ ID NO:09, wherein X is any genetically-encodable amino acid. Further exemplary embodiments are illustrated in SEQ ID NOS:07 and 08.

| | |
|---|---|
| MEKKSKPKNSVWKRLKSPFRKKKDSVTG | (SEQ ID NO.:07) |
| KKSKPKNSVWKRLKSPFRKKK | (SEQ ID NO.:08) |
| KKXKPKXXVWKRLKXPFRKKK | (SEQ ID NO.:09) |

Exemplary nuclear localization sequences suitable for use with the subject MBP include, but are not limited to, an NLS domain having an amino acid sequence of an NLS domain of karyopherin (importin) beta 3 (KPNB3), karyopherin alpha 6 (importin alpha 7) (KPNA6), Homo sapiens importin 8 (IPO8), the NLS from SV40, such as a triplit repeat of the SV40 NLS. A nucleic acid sequence of an exemplary MBP is provided in FIGS. 14A-14C (represented in underlined typeface). The amino acid sequence predicted from translation of the nucleic acid sequence for the exemplary MBP as shown in FIGS. 14A-14C in provided in FIG. 14D (represented in underlined typeface).

In such embodiments, during the cell cycle, the MBP fluorescence pattern results in a localized fluorescence in the nucleus during interphase. At the onset of the mitosis phase of the cell cycle and nuclear envelope breakdown (NEB), the localization of the MBP fluorescence pattern moves from the nucleus to the plasma membrane. At the completion of the mitosis phase of the cell cycle and nuclear envelope reformation (NER), the localization of the MBP fluorescence pattern changes once again resulting in a localized fluorescence within the nucleus.

G1 Phase Biosensor Polypeptide

The G1 phase biosensor polypeptide (G1BP) of the present invention is a fusion polypeptide comprising: 1) a reversible subcellular localizing domain (e.g., a phosphorylation-dependent nuclear exclusion domain); and 2) a fluorescent polypeptide domain.

In a representative embodiment, the G1BP includes a peptide domain derived from human DNA Helicase B (HDHB). In such embodiments, during the cell cycle, the G1BP fluorescence pattern results in localized fluorescence in either the nucleus or cytoplasm, depending on the particular phase of the cell cycle in which the cell resides. At the transition between the mitosis phase of the cell cycle and that G1 phase of the cell cycle, the G1BP fluorescence pattern changes resulting in a localized fluorescence in the nucleus of the cell. This nuclear localized fluorescence pattern is maintained throughout the G1 phase. At the transition between the G1 phase of the cell cycle and the S phase of the cell cycle the G1BP fluorescence pattern changes resulting in a localized fluorescence in the cytoplasm of the cell. This cytoplasmic localized fluorescence patterns continues through the G2 phase and the mitosis phase of the cell cycle.

A nucleic acid sequence of an exemplary G1BP is provided in FIG. 10C. The amino acid sequence predicted from translation of the nucleic acid sequence for the exemplary G1BP as shown in FIG. 10C is provided in FIG. 10D.

S Phase Biosensor Polypeptide

The S phase biosensor polypeptide (SBP) of the present invention is a fusion polypeptide comprising: 1) a reversible subcellular localizing domain (e.g., a nuclear localization signal), 2) a fluorescent polypeptide domain, 3) a flexible linker; and 4) a reversible DNA binding motif.

In representative embodiments, the SBP of the present invention is represented by the formula:

N-F-L-D wherein
N is a reversible subcellular target binding domain, such as a nuclear localization signal (NLS);
F is a fluorescent polypeptide domain;
L is a flexible linker domain; and
D is a reversible DNA binding motif.

The present invention thus contemplates SBPs comprising, in order from N- to C-terminus, a NLS, a fluorescent domain, and flexible linker; and a reversible DNA binding domain.

In a representative embodiment, the SBP includes a reversible DNA binding motif from the proliferating cell nuclear antigen (PCNA). Exemplary nuclear localization sequences suitable for use with the subject MBP include, but are not limited to, an NLS domain having an amino acid sequence of an NLS domain of karyopherin (importin) beta 3 (KPNB3), karyopherin alpha 6 (importin alpha 7) (KPNA6), Homo sapiens importin 8 (IPO8), the NLS from SV40, such as a triplit repeat of the SV40 NLS.

At the onset of the S phase of the cell cycle, the SBP fluorescence pattern is composed of localized fluorescence puncta within the nucleus of the cell. This SBP fluorescence pattern is maintained throughout the S phase of the cell cycle. At the completion of the S phase of the cell cycle, the SBP fluorescence pattern is one of more homogenous, non-punctate fluorescence throughout the nucleus of the cell.

A nucleic acid sequence of an exemplary SBP is provided in FIG. 10A. The amino acid sequence predicted from translation of the nucleic acid sequence for the exemplary SBP as shown in FIG. 10A is provided in FIG. 10B.

Nucleic Acids

The subject invention also provides nucleic acid compositions encoding the cell cycle biosensor polypeptides described herein. Nucleic acid compositions of particular interest comprise a sequence of DNA having an open reading frame that encodes a cell cycle biosensor polypeptide of the subject invention (e.g., a MBP coding sequence, SBP coding sequence, G1BP coding sequence) and is capable, under appropriate conditions, of being expressed as a protein according to the subject invention. Also encompassed in this term are nucleic acids that are homologous, substantially similar or identical to the nucleic acids of the present invention. Thus, the subject invention provides coding sequences encoding the proteins of the subject invention, as well as homologs thereof.

In addition to the above described specific nucleic acid compositions, also of interest are homologues of the above sequences. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). Of particular interest in certain embodiments are nucleic acids of substantially the same length as the nucleic acid identified as SEQ ID NO:01; SEQ ID NO:03; and SEQ ID NO:05, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e. the same as) or identical to the sequences of SEQ ID NO:01; SEQ ID NO:03; and SEQ ID NO:05. By substantially similar is meant that sequence identity will generally be at least about 60%, usually at least about 75% and often at least about 80, 85, 90, or even 95%.

Also provided are nucleic acids that encode the proteins encoded by the above described nucleic acids, but differ in sequence from the above described nucleic acids due to the degeneracy of the genetic code.

Also provided are nucleic acids that hybridize to the above described nucleic acids under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the cell cycle biosensor polypeptides of the invention are also provided. Mutant nucleic acids can be generated by random mutagenesis or targeted mutagenesis, using well-known techniques that are routine in the art. In some embodiments, biosensor polypeptides encoded by nucleic acids encoding homologues or mutants having the same biological properties as the polypeptides described herein.

The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. victoria*), and the like; in vivo and/or in vitro stability (e.g., half-life); as well as specificity for subcellular localization during the cell cycle, etc. By specificity for subcellular localization is meant either an increase or decrease, preferably an increase, in specificity for subcellular localization as compared to the non-mutated version of the fluorescent biosensor polypeptide by at least about 2 fold, including at least about 5 fold, about 10 fold, and more.

The subject nucleic acids may be present in an appropriate vector for extrachromosomal maintenance or for integration into a host genome, as described in greater detail below.

The nucleic acid compositions of the subject invention may encode all or a part of the subject targeting domains (subcellular localizing domains) or fluorescent labels, with the proviso that the biosensor polypeptides retain the desired function in emitting a fluorescent signal or targeting the biosensor to a subcellular location to retain the function of the biosensor polypeptide. Double or single stranded fragments of the subject targeting domains (subcellular localizing domains) or fluorescent labels may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject polynucleotides and constructs thereof are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual,* 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Also provided are constructs comprising the subject nucleic acids inserted into a vector, where such constructs may be used for a number of different applications, including propagation, protein production, etc. In some embodiments, a single vector (e.g., a plasmid) will contain nucleic acid coding sequence for a single cell cycle biosensor polypeptide, such as MBP, G1BP or SBP. In such embodiments, the nucleic acid coding sequence for each of MBP, G1BP, and SBP are inserted into three different vectors, such as plasmids. In other embodiments, a single vector (e.g., plasmid) will contain the nucleic acid coding sequence for one or more of the cell cycle biosensor polypeptides. In such embodiments, a single vector may contain the nucleic acid coding sequence for one, two, or all three, of the biosensor polypeptides. For example, a single vector may contain the nucleic acid coding sequence for both MBP and SBP, or the vector may contain the nucleic acid coding sequence for MBP, SBP, and G1BP.

Viral and non-viral vectors may be prepared and used, including plasmids, which provide for replication of biosensor-encoding DNA and/or expression in a host cell. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transformation and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Eukaryotic promoters suitable for use include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gal1 gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Promoters may be, furthermore, either constitutive or regulatable. Inducible elements are DNA sequence elements that act in conjunction with promoters and may bind either repressors (e.g. lacO/LAC Iq repressor system in *E. coli*) or inducers (e.g. gal1/GAL4 inducer system in yeast). In such cases, transcription is virtually "shut off" until the promoter is derepressed or induced, at which point transcription is "turned-on."

Expression vectors generally have convenient restriction sites located near the promoter sequence to provide for the insertion of nucleic acid sequences encoding heterologous proteins. A selectable marker operative in the expression host may be present. Expression vectors may be used for, among other things, the screening methods described in greater detail below.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (USA) (1983) 80:21-25; and Siebenlist et al., *Cell* (1980) 20:269.

Mammalian expression is accomplished as described in Dijkema et al., *EMBO J.* (1985) 4:761, Gorman et al., *Proc. Natl. Acad. Sci.* (USA) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

The subject nucleic acids may be mutated in various ways known in the art to generate targeted changes in the sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4.

Polypeptides

Also provided by the subject invention are biosensor polypeptides and biosensor polypeptides comprising mutants of the subject targeting domains (subcellular localizing domains) or fluorescent labels encoded by the subject nucleic acids, as well as polypeptide compositions related thereto. The term polypeptide composition as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described in greater detail below.

Homologs (or fragments thereof) of the subject polypeptide targeting domains (subcellular localizing domains) or fluorescent labels that vary in sequence from the amino acid sequences of the above provided cell cycle biosensor polypeptides are also provided. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive Multiple Sequence Alignments on a Microcomputer," (1989) CABIOS, 5: 151-153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the sequences of the above provided specific subject targeting domains (subcellular localizing domains) or fluorescent labels, where by substantially identical is meant that the protein has an amino acid sequence identity to the one of the above specifically provided proteins of at least about 60%, usually at least about 65% and more usually at least about 70%, where in some instances the identity may be much higher, e.g., 75%, 80%, 85%, 90%, 95% or higher.

Proteins which are mutants of the above specifically described subject targeting domains (subcellular localizing domains) or fluorescent labels are also provided. Mutants may retain biological properties of the wild-type (e.g., naturally occurring) proteins, or may have biological properties that differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. victoria*), and the like; in vivo and/or in vitro stability (e.g., half-life); as well as specificity for subcellular localization during the cell cycle, etc. By specificity for subcellular localization is meant either an increase or decreases in specificity for subcellular localization as compared to the non-mutated version of the biosensor polypeptide by at least about 2 fold, including at least about 5 fold, about 10 fold, and more. Mutants include single amino acid changes, deletions of one or more amino acids, N-terminal truncations, C-terminal truncations, insertions, etc. Mutants can be generated using standard techniques of molecular biology, e.g., random mutagenesis, and targeted mutagenesis.

The subject proteins and polypeptides may be synthetically produced using any convenient protocol, e.g., by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Cell Lines

The invention also features host cells engineered to express one or more of the florescent biosensor polypeptides as well as practicing the methods of the subject invention. In general, the subject cell lines are mammalian cells that support production of one or more of the biosensor polypeptides, such as MBP, SBP, or G1BP, according to the invention. Preferably, the cell line is one that can be readily propagated in culture and is readily manipulated using recombinant techniques. Exemplary cell lines, include, but are not necessarily limited to, mammalian cell lines (particularly human cell lines), such as 293T cells, HeLa cells, and the like.

In general, the cell lines are generated by introduction of one or more constructs for expression of one or more of the biosensor polypeptides (e.g., MBP and SBP, or all three polypeptides) of the invention. As described in greater detail above, in some embodiments a single polynucleotide e.g., plasmid, may encode all three of the biosensor polypeptides. In other embodiments, a single polynucleotide e.g., plasmid, may encode one or two of the biosensor polypeptides, or any combination thereof, wherein if a cell line engineered to express all three biosensor polypeptides is desired, all the necessary constructs will be introduced in the cells. For example, where each biosensor polypeptide is encoded on a different construct, all three constructs will be introduced in the cell line in order to generate a cell line expressing all three biosensor polypeptides.

The constructs can be introduced into the host cell by any one of the standard means practiced by one with skill in the art to produce a cell line of the invention. The nucleic acid constructs can be delivered, for example, with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", and the like.

In some embodiments, the one or more biosensor polypeptides are introduced into the cell as a polynucleotides encoding the one or more biosensor polypeptides and an expression cassette, optionally carried on one or more transient expression vectors (e.g., the vector is maintained in an episomal manner by the cell), which comprise the polynucleotides encoding the one or more biosensor polypeptides.

In other embodiments, one or more expression constructs encoding one or more biosensor polypeptides can be stably integrated into the cell line. In addition or alternatively, one or more of polynucleotides encoding one or more biosensor polypeptides can be stably integrated into the cell, while one or more other biosensor polypeptides can be optionally carried on one or more transient expression vectors. For example, a polynucleotide encoding the MBP may be stably integrated in the cell line, while a polynucleotide encoding SBP and G1BP are carried on one or more transient expression vectors. Likewise, a polynucleotide encoding SBP and G1BP may be stably integrated in the cell line, while a polynucleotide the MBP is carried on one or more transient expression vectors.

Methods of Using Biosensor Polypeptides

As mentioned above, the subject cell cycle biosensor polypeptides find particular utility in assays designed to monitor the duration of a cell cycle phase of a mammalian cell, as well as identification of the cell cycle stage of fixed mammalian cells. In addition, the subject cell cycle biosensor polypeptides also find particular utility in screening assays designed to identify an agent (e.g., a gene product or small molecule compound) that modulates the duration of a cell-cycle phase of a mammalian cell.

Monitoring Cell Cycle Phases

As noted above, the present invention provides a method for monitor the duration of a cell cycle phase of a mammalian cell, as well as identification of the cell cycle stage of fixed mammalian cells. In practicing the subject method, a mammalian cell comprising one or more cell cycle biosensor polypeptide that monitors a cell-cycle phase, such as mitosis, G1, S, or G2 phase, is cultured under conditions suitable for proliferation of the mammalian cell, and based on the fluorescence pattern of the cell cycle biosensor polypeptide used, the specific cell cycle phase of the cell can be determined.

Cells

Cells suitable for use with the subject methods of the present invention are generally any higher eukaryotic cell, such as mammalian cells. In some embodiments, the cells are an easily manipulated, easily cultured mammalian cell line, preferably human cell lines such as, not necessarily limited to 293 cells, HeLa cells, and the like. In other embodiments, cells suitable for use are non-transformed primary human cells. In still other embodiments, cells suitable for use with subject invention are cells derived from a patient sample such as a cell biopsy, wherein the cells may or may not have distinct characteristics associated with certain diseases, such as a cell cycle disease, including cancer. The cells used in the assay can contain an expression vector encoding one or more biosensor polypeptides. Alternatively, although less practically, the cells can contain one or more biosensor polypeptides as a result of introduction of the biosensor polypeptide into the cell (e.g., by microinjection of the protein).

MBP Fluorescence Pattern

In one embodiment, the subject method is carried out by culturing a mammalian cell comprising a mitosis biosensor polypeptide (MBP) under conditions suitable for proliferation of the mammalian cell, wherein the MBP comprises a fluorescent label; and determining a time interval between nuclear envelope breakdown (NEB) and nuclear envelope reformation (NER) by detecting a MBP fluorescence pattern, wherein the time interval is indicative of a cell cycle phase. In such embodiments, the time interval between NEB and NER determines a time-duration of mitosis phase of a cell cycle. In addition, the time interval between NER and NEB determines a time-duration of G1, S, and G2 phase of a cell cycle. Furthermore, the time interval between NEB and NEB or NER and NER determines a complete cell cycle phase. In some embodiments, the method further includes determining a time interval between at least two of NEB, prometaphase, metaphase, anaphase, cytokinesis, and NER, wherein NEB and NER are established by detection of a MBP fluorescence pattern and prometaphase, metaphase, anaphase, cytokinesis are established by detection of a condensed chromatin associated MBP fluorescence pattern.

As used herein "a MBP fluorescence pattern" or "fluorescence pattern of MBP", means the fluorescence pattern associated with the subcellular localization pattern of the MBP during specific cell cycle events. Such a "MBP fluorescence pattern" or "fluorescence pattern of MBP" can be determined either at a single moment in time (e.g., a single image of the fluorescence pattern of the cell for determining the cell cycle phase of a fixed cell) or over a period of time (e.g., time lapse images of the fluorescence pattern of the cell over a period of time). As noted above, the subcellular localization pattern of the MBP will be dependent upon the cellular targeting domain used, which enables the biosensor polypeptide to localize to specific regions of the cell during the cell cycle.

As used herein "a condensed chromatin associated MBP fluorescence patter" or "fluorescence pattern of MBP associated with condensed chromatin", means the fluorescence pattern associated with the subcellular localization pattern of the MBP during specific cell cycle events of mitosis. Such a "condensed chromatin associated MBP fluorescence pattern" or "fluorescence pattern of MBP associated with condensed chromatin" can be determined either at a single moment in time (e.g., a single image of the fluorescence pattern of the cell for determining the cell cycle phase of a fixed cell, such as prometaphase, metaphase, anaphase, or cytokinesis) or over a period of time (e.g., time lapse images of the fluorescence pattern of the cell over a period of time). As noted above, the subcellular localization pattern of the MBP will be dependent upon the cellular targeting domain used, which enables the biosensor polypeptide to localize to the condensed chromatin of the cell during the cell cycle.

In a representative embodiment, the MBP includes a plasma membrane targeting domain and a nuclear localization signal. In such embodiments, during the cell cycle in a live cell, a MBP fluorescence pattern in which fluorescence is localized in the nucleus indicates the cells is in a cell cycle phase other than mitosis (e.g., the cell is in one of G1, S or G2). An MBP fluorescence pattern in which fluorescence is localized to the nucleus may be referred to as a "non-M phase MBP pattern" or "interphase MBP pattern". As is well known in the art, "interphase" refers the period of the cell cycle between mitotic phases and is composed of G1, S and G2.

At the onset of the mitosis phase which is associated with nuclear envelope breakdown (NEB), the MBP fluorescence pattern shifts to one of localized fluorescence at the plasma membrane, which indicates the cell is in the mitosis phase of the cell cycle. This latter plasma membrane-localized MBP fluorescence pattern may be referred to as an "M phase MBP pattern".

At the completion of the mitosis phase of the cell cycle, which is associated with nuclear envelope reformation (NER), the MBP fluorescence pattern changes to the non-M phase (interphase) MBP fluorescence pattern, with localized fluorescence in the nucleus indicating the cell is no longer in mitosis. Accordingly, the MBP fluorescence pattern is indicative of a cell cycle phase in the mammalian cell.

During M Phase the MBP has a chromatin associated MBP fluorescence pattern, where the chromatin associated MBP fluorescence pattern is predominately localized at the plasma membranes as well as the condensed chromatin. The chromatin associated MBP fluorescence pattern associated with the plasma membranes and condensed chromatic occurs upon NEB. Since the chromatin associated MBP fluorescence pattern is associated with the condensed chromatin of mitotic cells, different stages of mitosis (e.g., prometaphase, metaphase, anaphase, cytokinesis, etc.) can be visualized. Accordingly, the chromatin associated MBP fluorescence pattern is indicative of different stages of the mitosis phase in the mammalian cell. The chromatin associated MBP fluorescence pattern remains associated with both the plasma membrane and the condensed chromatin until after anaphase onset when the nuclear envelopes are reformed (NER) around the daughter chromatin.

As such, the MBP fluorescence pattern can be used to assess initiation/end of the mitosis by assessing whether the MBP fluorescence pattern is nuclear vs. predominantly plasma membrane associated. However, as noted above, during M phase the MBP fluorescence pattern is predominantly associated with the plasma membrane as well as the condensed chromatin of the mammalian cell. As such, condensed chromatin associated MBP fluorescence pattern allows for monitoring and determining the duration of discrete phases of the M phase, such as prometaphase, metaphase, anaphase, cytokinesis, etc, on a finer scale.

It will be readily appreciated that when live cells are monitored, the MBP of the invention facilitates monitoring of cell cycle beginning at any cell cycle phase, or any stage of the mitotic phase. Moreover, the MBP can be used in a variety of ways to assess the cell cycle. For example, the MBP and its associated fluorescence pattern can be used to determine the duration of M phase, the duration of interphase (G1/S/G2), the time interval from end of M phase to beginning of the next M phase in a cell cycle, the time interval from the end of interphase to beginning of interphase in a cell cycle, the length of a complete cell cycle including M phase and interphase. In addition the MBP and its associated fluorescence pattern with condensed chromatin can be used to determine the duration of prometaphase, the time interval from the beginning of M phase (NEB) to metaphase, the time interval from the and of metaphase to the beginning of anaphase, the time interval from the beginning of M phase to anaphase, the time interval from the beginning of M phase to cytokinesis, the time interval from the beginning of metaphase to the end of M phase, the time interval from the beginning of anaphase to the end of M phase, etc.

Use of Two or More Biosensor Polypeptides

In further embodiments, the mammalian cell is modified to contain two or more biosensor polypeptides according to the invention. In one embodiment, the cell contains an MBP and further contains at least one of a G1 phase biosensor polypeptide (G1BP) or an S phase biosensor polypeptide (SBP). In such embodiments, the G1BP fluorescent label has a different emission spectrum than the SBP fluorescent label. In still further embodiments, the G1BP fluorescent label and the SBP fluorescent label may have different emission spectrum than the MBP fluorescent label, such that each biosensor polypeptide has a fluorescent polypeptide with a different emission spectrum than the fluorescent polypeptide of another biosensor polypeptide.

Furthermore, each biosensor polypeptide has a distinct fluorescence pattern throughout the cell cycle that correlates with a distinct phase of the cell cycle (see FIG. 16). For example, the exemplary G1BP described above has a nuclear pattern of fluorescence during the G1 phase of the cell cycle and a cytoplasmic pattern of fluorescence during the S, G2 and M phases of the cell cycle. Therefore, two or more, including all three biosensor polypeptides, can be to establish more time points in order to determine the specific cell cycle phase of a cell.

In such embodiments, the method further includes determining a time interval between at least two of NEB (e.g., as detected by a MBP pattern), NER (e.g., as detected by a MBP pattern), formation of fluorescence puncta in a nuclear region of the mammalian cell (e.g., as detected by a SBP pattern), disappearance of fluorescence puncta in the nuclear region of the mammalian cell (e.g., as detected by a SBP pattern), appearance of fluorescence in a nuclear region of the mammalian cell (e.g., as detected by a G1BP pattern), and translocation of fluorescence from a nuclear region to a cytoplasmic region of the mammalian cell (e.g., as detected by a G1BP pattern), wherein the time interval is indicative of a cell cycle phase. As described above, NEB and NER are detectable by determining the MBP fluorescence pattern associated with the subcellular localization of the MBP during the cell cycle. In addition, formation of fluorescence puncta and disappearance of fluorescence puncta are detectable by determining the SBP fluorescence pattern associated with the subcellular localization f the SBP during the cell cycle.

In some embodiments, the time interval between NER and formation of fluorescence puncta in a nuclear region of the mammalian cell indicates the duration of G1 phase of a cell cycle. In other embodiments, the time interval between formation of fluorescence puncta in a nuclear region of the mammalian cell and disappearance of fluorescence puncta in the nuclear region of the mammalian cell indicates the duration of S phase of a cell cycle. In still other embodiments, the time interval between disappearance of fluorescence puncta in a nuclear region of the mammalian cell and NEB indicates the duration of G2 phase of a cell cycle. In still other embodiments, the time interval between NER and translocation of fluorescence from a nuclear region to a cytoplasmic region of the mammalian cell by the G1BP determines a time-duration of G1 phase of a cell cycle. In still other embodiments, the time interval between translocation of fluorescence from a nuclear region to a cytoplasmic region of the mammalian cell by the G1BP and disappearance of fluorescence puncta in a nuclear region of the mammalian cell by the SBP determines a time-duration of S phase of a cell cycle. In still other embodiments, the time interval between appearance of fluorescence in a nuclear region of the mammalian cell by the G1BP and translocation of fluorescence from a nuclear region to a cytoplasmic region of the mammalian cell by the G1BP determines a time-duration of G1 phase of a cell cycle.

G1BP Fluorescence Pattern

As used herein "a G1BP fluorescence pattern" or "fluorescence pattern of G1BP", means the fluorescence pattern associated with the subcellular localization pattern of the G1BP during specific cell cycle events. Such a "G1BP fluorescence pattern" or "fluorescence pattern of G1BP" can be determined either at a single moment in time (e.g., a single image of the fluorescence pattern of the cell for determining the cell cycle phase of a fixed cell) or over a period of time (e.g., time lapse images of the fluorescence pattern of the cell over a period of time).

In a representative embodiment, the G1BP includes a peptide domain derived from human DNA Helicase B. In such embodiments, during the cell cycle, the G1BP fluorescence pattern results in localized fluorescence at either the nucleus or cytoplasm, depending on the particular phase of the cell cycle in which the cell resides. At the transition between the mitosis phase and entering into the G1 phase, the localization of the G1BP fluorescence pattern changes, resulting in a localized fluorescence in the nucleus of the cell. This nuclear localized fluorescence pattern is maintained through the G1 phase of the cell cycle. At the transition between the G1 phase of the cell cycle and the S phase of the cell cycle the G1BP fluorescence pattern changes, resulting in a localized fluorescence in the cytoplasm of the cell. This cytoplasmic localized fluorescence patterns is maintained through the S, G2 and the mitosis phases of the cell cycle. Accordingly, the G1BP fluorescence pattern is indicative of a cell cycle phase-either a period of the cell cycle encompassing G1 phase (G1) or encompassing S, G2 and mitosis (S/G2/M).

SBP Fluorescence Pattern

As used herein "a SBP fluorescence pattern" or "fluorescence pattern of SBP", means the fluorescence pattern associated with the subcellular localization pattern of the SBP during specific cell cycle events. Such a "SBP fluorescence pattern" or "fluorescence pattern of SBP" can be determined either at a single moment in time (e.g., a single image of the fluorescence pattern of the cell for determining the cell cycle phase of a fixed cell) or over a period of time (e.g., time lapse images of the fluorescence pattern of the cell over a period of time).

In a representative embodiment, the SBP includes a polypeptide domain from the proliferating cell nuclear antigen (PCNA). At the onset of the S phase of the cell cycle, the SBP fluorescence pattern results in localized fluorescence puncta within the nucleus of the cell. This SBP fluorescence pattern is maintained throughout the S phase of the cell cycle. At the completion of S phase, the SBP fluorescence pattern changes so that fluorescence is no longer punctate, but rather more homogenously present throughout the nucleus of the cell. Accordingly, the SBP fluorescence pattern is indicative of a cell cycle phase, and indicates whether the cell is in S phase (a punctate nuclear SBP fluorescence pattern) or in a cell cycle phase other than S phase (a "non-S phase cell cycle, indicated by a non-punctate nuclear SBP fluorescence pattern).

Detection of Fluorescence

Methods of measuring and/or monitoring fluorescence are well known in the art. Both qualitative assessments (positive/negative) and quantitative assessments (comparative degree of fluorescence) may be provided by the present methods. Brightness can be measured using any known method, including, but not limited to, visual screening, spectrophotometry, spectrofluorometry, fluorescent microscopy, by fluorescence activated cell sorting (FACS) machines, etc. In some embodiments, monitoring of fluorescent biosensor polypeptides includes the use of an automated imaging system such as an Axon ImageXpress 5000 equipped with a live cell imaging chamber. Other suitable imaging systems include, but are not limited to, BD Biosciences (Pathway HT); Cellomics (ArrayScan V); Amersham (IN Cell Analyzer 1000,  IN Cell Analyzer 3000); Molecular Devices (Discovery-1, Discovery-TMA, ImageXpress), and the like.

Fixed Cells

As noted above, the subject biosensor polypeptides can also be used to identify the specific cell cycle phase a fixed cell resides in. As such, the present invention provides a method of monitoring a cell-cycle phase of a mammalian cell, comprising culturing a mammalian cell comprising a MBP under conditions suitable for proliferation of the mammalian cell, wherein the MBP comprises a fluorescent label; and detecting a MBP fluorescence pattern established by NEB or NER, wherein the MBP fluorescence pattern is indicative of a phase of a cell cycle. In some embodiments, the cells are fixed prior to detection of a MBP fluorescence pattern. As described in greater detail above, a MBP fluorescence pattern established by NEB is indicative of a mitosis phase of a cell cycle and a MBP fluorescence pattern established by NER is indicative of interphase of a cell cycle.

The subject cell cycle phase may be determined qualitatively (positive/negative) or quantitatively (comparative degree of fluorescence) for the cell by any known method described above. In some embodiments, it is desirable to know the specific cell cycle phase a population of cells resides at two different time points. In such embodiments, the percentage of cells in a particular cell cycle phase can be determined in a given field (e.g., a microscope field) compared to the total number of cells in the given field. The percentage of cells in the same cell cycle phase can then be recalculated at a second time point. This can be repeated as desired. In some embodiments, the method is carried out in the presence of a candidate agent in order to determine whether the candidate agent modulates the duration (e.g., increases or decreases) of a cell cycle phase.

In other embodiments, more than one biosensor polypeptide may be used in order to further determine the cell cycle phase of the cell. In such embodiments, the mammalian cell further comprises a G1 phase biosensor polypeptide (G1BP) comprising a fluorescent label, and an S phase biosensor polypeptide (SBP) comprising a fluorescent label, wherein the fluorescent labels of the G1BP and of the SBP emit in different fluorescence emission spectra. As such, the method further includes detecting at least one of a) G1BP fluorescence pattern established by a nuclear localized fluorescence and a cytoplasmic localized fluorescence; and b) SBP fluorescence pattern established by formation of fluorescence puncta in a nuclear region of the mammalian cell and disappearance of fluorescence puncta. A G1BP fluorescence pattern established by nuclear localized fluorescence is indicative of G1 phase of a cell cycle. Furthermore, a G1BP fluorescence pattern established by cytoplasmic localized fluorescence is indicative of S or G2 phase of a cell cycle, and a SBP fluorescence pattern established by formation of fluorescence puncta in a nuclear region of the mammalian cell is indicative of S phase of a cell cycle.

Screening for Agents That Modulate a Cell Cycle Phase

As further noted above the subject methods can also be used as a screening assays designed to identify an agent (e.g., a gene product or small molecule compound) that modulates the duration of a cell-cycle phase of a mammalian cell. In some embodiments, the modulating results in increasing the duration of a cell cycle phase, such as G1 or G2, etc. In other embodiments, the modulating results in decreasing the duration of a cell cycle phase, such as G1 or G2, etc.

In one embodiment, the subject method is carried out by culturing a mammalian cell comprising a mitosis biosensor polypeptide (MBP) in the presence of a candidate agent under conditions suitable for proliferation of the mammalian cell, wherein the MBP comprises a fluorescent label; and determining a time interval between at least two of nuclear envelope breakdown (NEB), metaphase, anaphase, and nuclear envelope reformation (NER) by detecting a MBP fluorescence pattern, wherein an increase or decrease in the time interval as compared to a time interval in the absence of a candidate agent indicates the candidate agent modulates duration of a cell-cycle phase of the mammalian cell. In such embodiments, the time interval between NEB and NER determines a time-duration of mitosis phase of a cell cycle. Furthermore, the time interval between NEB and metaphase determines a time-duration of prometaphase, the time interval between the onset of metaphase and anaphase determines a time-duration of metaphase, and the time interval between the onset of anaphase and NEB determines a time-duration of anaphase. In addition, the time interval between NER and NEB determines a time-duration of interphase (G1, S, and G2 phases) of a cell cycle. Furthermore, the time interval between NEB to NEB (mitosis to interphase to mitosis) or NER to NER (interphase to mitosis to interphase) determines the length of a complete cell cycle phase.

In further embodiments, the mammalian cell further comprises a G1 phase biosensor polypeptide (G1BP) comprising a fluorescent label and a S phase biosensor polypeptide (SBP) comprising a fluorescent label, wherein the G1BP fluorescent label has a different emission spectrum than the SBP fluorescent label. In still further embodiments, the G1BP fluorescent label and the SBP fluorescent label have different emission spectrum than the MBP fluorescent label, wherein each biosensor polypeptides has a fluorescent label that has a different emission spectrum than the fluorescent label of another biosensor polypeptide.

In such embodiments, the method further includes determining a time interval between at least two of NEB (e.g., as detected by a MBP pattern), NER (e.g., as detected by a MBP pattern), formation of fluorescence puncta in a nuclear region of the mammalian cell (e.g., as detected by a SBP pattern), disappearance of fluorescence puncta in the nuclear region of the mammalian cell (e.g., as detected by a SBP pattern), appearance of fluorescence in a nuclear region of the mammalian cell (e.g., as detected by a G1BP pattern), and translocation of fluorescence from a nuclear region to a cytoplasmic region of the mammalian cell (e.g., as detected by a G1BP pattern). In one embodiment, one or more time intervals between one or more cell cycle phases is determined by detecting changes in at least one of a MBP fluorescence pattern, a G1BP fluorescence pattern, and a SBP fluorescence pattern over time, wherein an increase or decrease in the time interval as compared to a time interval in the absence of a candidate agent indicates the candidate agent modulates duration of the cell-cycle phase of the mammalian cell. In some embodiments, the time interval between NER and formation of fluorescence puncta in a nuclear region of the mammalian cell determines a time-duration of G1 phase of a cell cycle. In other embodiments, the time interval between formation of fluorescence puncta in a nuclear region of the mammalian cell by the SBP and disappearance of fluorescence puncta in the nuclear region of the mammalian cell by the SBP determines a time-duration of S phase of a cell cycle. In still other embodiments, the time interval between disappearance of fluorescence puncta in a nuclear region of the mammalian cell by the SBP and NEB determines a time-duration of G2 phase of a cell cycle. In still other embodiments, the time interval between NER and translocation of fluorescence from a nuclear region to a cytoplasmic region of the mammalian cell by the G1BP determines a time-duration of G1 phase of a cell cycle. In still other embodiments, the time interval is between translocation of fluorescence from a nuclear region to a cytoplasmic region of the mammalian cell by the G1BP and disappearance of fluorescence puncta in a nuclear region of the mammalian cell by the SBP determines a time-duration of S phase of a cell cycle. In still other embodiments, the time interval between appearance of fluorescence in a nuclear region of the mammalian cell by the G1BP and translocation of fluorescence from a nuclear region to a cytoplasmic region of the mammalian cell by the G1BP determines a time-duration of G1 phase of a cell cycle.

Through use of the subject screening methods, one can identify compounds that have activity with respect to modulating the duration of a cell cycle, with particular interest in agents that have utility in treating cell cycle diseases, such as unregulated cellular division, including cancer. Compounds have activity with respect to the duration of a cell cycle if they modulate or have an effect on at least one cell cycle phase, such as a decrease in the duration of, for example, S phase or mitosis. Modulation (including a decrease or an increase) in duration of a cell cycle phase includes a change (increase or decrease in time relative to that in the absence of the agent) by at least about 10% or more, about 12% or more, about 15% or more, about 17% or more, about 20% or more, including about 30% or more, about 40% or more, about 50% or more, about 75% or more, and the like. Thus, the screening methods of subject invention can be used to identify compounds that modulate the duration of a cell cycle, e.g. by decreasing the duration of a cell cycle phase.

Screening to determine drugs that do not significantly modulate duration of a cell cycle phase is also of interest. Assays of the invention make it possible to identify agents (such as a gene product or a compound) which ultimately: (1) have a positive effect with respect to modulating the duration of a cell cycle phase and as such are potential therapeutics, e.g. agents which arrest uncontrolled cellular proliferation; or (2) have an adverse affect with respect to the cell cycle and as such should be avoided as therapeutic agents (e.g., to screen candidate agents for toxicity to mammalian cells).

Generally a plurality of assay mixtures is performed in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate agents are tested in parallel using a large number of cell populations. By "large number" is meant a plurality, where plurality means at least 10 to 50, usually at least 100, and more usually at least 1000, where the number of may be 10,000 or 50,000 or more, but in many instances will not exceed 5000.

Of particular interest in certain embodiments is the use of the subject methods in a high throughput toxicity screening assays. In such high throughput screening (HTS) assays, a plurality of different compound compositions, usually at least 10 different compound compositions, are simultaneously assayed for their activity, if any. Each compound composition in the plurality is assayed for activity by contacting it with a cell comprising the subject biosensor polypeptides and determining the effect of the compound composition on the cell cycle phase. Such HTS methods find particular use in finding agents for use in the treatment of cell cycle diseases, e.g. cancer, as only those compounds that treat the disease and yet are sufficiently non-toxic are identified as positives for further study.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

The above screening methods may be part of a multi-step screening process of evaluating candidate agents for their efficacy (and safety) in the treatment of cell cycle diseases, e.g., cancer, in mammalian hosts, e.g. humans. In multi-step screening processes of the subject invention, a candidate compound or library of compounds is subjected to screening in a second in vivo model, e.g. a mouse model, following screening in the subject cell lines. Following the initial screening in the cell lines of the subject invention, the positive compounds are then screened in non-human mammalian animal models. In addition, a pre in vivo screening step may be employed, in which the compound is first subjected to an in vitro screening assay for its potential as a therapeutic agent in the treatment of cell cycle disease. Any convenient in vitro screening assay may be employed, where a variety of suitable in vitro screening assays are known to those of skill in the art.

In some embodiments, the subject methods are useful for identifying a endogenous gene product that has an activity in modulating the duration of a cell cycle phase of a cell. Genes that have a beneficial effect on the phenotype when their activity is modulated through mutation encode proteins that represent therapeutic targets for the development of compounds that inhibit the function of the protein. Gene based therapies can be identified by doing traditional enhancer/suppressor analyses in the subject cells. In these analyses, genes in the subject cells are mutated to identify ones that either increase or decrease the duration of a cell cycle. Methods of mutating genes and carrying out enhancer/suppressor analyses are well known to those of skill in the art (Hays, T S et al., Molecular and Cellular Biology (March 1989) 9(3): 875-84; Deuring, R; Robertson, B; Prout, M; and Fuller, M T. Mol. Cell. Biol., 1989 9:875-84; Fuller, M T et al., Cell Mot. Cyto. (1989) 14:128-35; Rottgen G, Wagner T, Hinz U Mol. Gen. Genet. 1998 257:442-51). In some embodiments, siRNA is used to disrupt the expression of an endogenous gene to determine whether the endogenous gene had an effect on modulating the duration of a cell cycle phase.

Genes that mutate to modulate the duration of a cell cycle in a recessive manner yield potential protein therapeutics for disease conditions associated with the cell cycle, such as cancer, since elevating the normal gene product level of such genes potentially alleviates the disease condition. Genes that mutate to suppress the disease condition in a recessive manner yield gene targets for disruption to alleviate the disease conditions, where disruption of these genes can be achieved using a variety of methods, ranging from deleting the DNA for the target gene to inhibiting its transcription, translation, or protein activity. For screening candidate agents, small molecule antagonists to these genes can be constructed and evaluated for efficacy in the subject methods. Alternatively, the human homolog of the gene can be identified and small molecular antagonists that inhibit the gene product of the human homolog can be identified in high-throughput in vitro or cellular screens and validated in rodent models. Alternatively, large molecular antagonists can be delivered by gene therapy.

Automated Screening Methods

The methods of the present invention may be automated to provide convenient, real time, high volume methods of screening compounds for activity in modulation of a cell cycle phase. Automated methods are designed to detect changes in the localization of the fluorescence of one or more of the biosensor polypeptides over time (i.e., comparing the same apparatus before and after exposure to a test sample), or by comparison to a control apparatus, which is not exposed to the test sample, or by comparison to pre-established indicia. Both qualitative assessments (positive/negative) and quantitative assessments (e.g., duration or comparative degree of translocation) may be provided by the present automated methods.

An embodiment of the present invention includes an apparatus for duration of a cell cycle phase in a test sample of cells according to the subject methods of the present invention. This apparatus comprises means, such as a fluorescence measurement tool, for measuring change in the localization of fluorescence associated with one or more biosensor polypeptides during the cell cycle of a cell in response to a particular candidate agent.

Measurement points may be over time, or among test and control samples. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool is preferably operatively coupled to a general purpose or application specific computer controller. The controller preferably comprises a computer program produce for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

Kits and Systems

Also provided by the subject invention are kits and systems for use in practicing the subject methods, where the subject kits typically include elements for making the subject biosensor polypeptides e.g., a construct comprising a vector that includes a coding region for the subject biosensor polypeptides. In some embodiments, the subject kits and systems can include, in separate compartments or containers, one or more of the following: 1) one or more constructs encoding one or more of the biosensor polypeptides, such as MBP, SBP and G1BP; 2) a candidate agent; and 3) a cell containing an expression construct for producing one or more of the biosensor polypeptides, such as MBP, SBP and G1BP. The components of the kits may be modified commensurate to the disclosure provided above.

The subject kit components are typically present in a suitable storage medium, e.g., buffered solution, typically in a suitable container. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression of a biosensor polypeptide, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials are used in the examples below.

Engineering of the Mitosis Biosensor Polypeptide pFMB

Nucleic acid encoding twenty-eight amino acids defining a plasma membrane targeting domain of the carboxy terminus of the small GTPase Ras like protein (Ritl) was amplified from a fusion protein of cyan fluorescent protein and Ritl (CFP-Rit) expression clone using the following primers: 5' GCCG GCT AGC ATG GAG AAA AAA TCT AAG CCC AA 3' (SEQ ID NO:10); 5' GGC CAC CGG TCC AGT TAC TGA ATC TTT CTT CT 3' (SEQ ID NO:11). The 5' primer used for PCR included a Nhe I site and the 3' primer included an Age I site. These restriction digest sites were used to facilitate ligation of the PCR product into a vector encoding fusion protein of an enhanced yellow fluorescent protein (EYFP) and a triplet repeat of the SV40 nuclear localization signal (EYFP-NLS, Clontech laboratories, Palo Alto Calif., Catalogue No. 632354 The resulting vector encoded a fusion protein composed of, from N- to C-terminus, Ritl PM targeting domain-EYFP-NLS.

FIGS. 14A-14D show the nucleic acid and amino acid sequence of the MBP used in the examples below.

Engineering of the S Phase Biosensor Polypeptide (SBP)

The SV40 NLS was inserted into the pEVRF (Matthias, et al., Nuc. Acid Res. 17:6418 (1989)) expression vector backbone between the BamHI and AgeI restriction sites. EYFP (Clontech Cat. No. 6006-1) was inserted between the AgeI and BsrGI restriction sites, the linker between the BsrGI and ClaI restriction sites, and PCNA (Genbank Accession No. NM_002592) was inserted between the ClaI and XbaI restriction sites.

FIGS. 10A and 10B show the nucleic acid and amino acid sequence of the SBP used in the examples below.

Engineering of the G1 Phase Biosensor Polypeptide (G1BP)

Nucleic acids from the carboxy terminus of human DNA helicase B (HDHB) (GenBank Accession No. AF319995) were amplified from a full human brain cDNA library using the following primers: 5' CCC AAG CTT GGG CTC TCC TCT AGC GGC GCA 3' (SEQ ID NO:12); 5' CGG GGT ACC CCG AGT TTC TTG ATT ATC GGT GGG C 3' (SEQ ID NO:13). The 5' primer used for PCR included a HindIII site and the 3' primer included a KpnI site. These restriction digest sites were used to facilitate ligation of the PCR product into a vector encoding a red fluorescent protein (tdimer2) (Campbell et al., PNAS 19:7877-7882 (2002)). The resulting vector encoded a fusion protein composed of, from N- to C-terminus, HDHB carboxy terminus-tdimer2.

FIGS. 10C and 10D show the nucleic acid and amino acid sequence of the G1BP used in the examples below.

Generation of rMad2 d-siRNAs

The rat mitotic spindle checkpoint protein Mad2 (mitotic arrest-deficient 2) was isolated from an RBL cDNA library using the following primers: 5' GCG <u>TAATACGACTCACTATAG</u>GAT GGC ACA GCA GCT CGC CCG 3' (SEQ ID NO:14); 5' GCG <u>TAATACGACTCACTATAG</u>GTC AGT CAC TGA CAG GTG TTT 3' (SEQ ID NO:15) (T7 promoters are represented by underlined typeface). The resulting cDNA was subjected to in vitro transcription to yield a 600 dsRNA. In Vitro dicing was done as previously described (Myers et al., Nat. Biotechnology 21:324-328 (2003)).

Cell Culture and Transfections

Rat Basophilic Leukemia Cells (RBL) were grown in Dulbecco's modified Eagles Media (DMEM) supplemented with 10% fetal calf serum, 2 mM glutamine, 100 U/ml penicillin, and 100 μg/ml streptomycin (all from Invitrogen, Carlsbad, Calif.). 10 million cells were electroporated (BioRad, Hercules, Calif.) in 600 μl of media with 40 μg of pFMB. These were allowed to recover for 48 hours and cells stably expressing the biosensor were selected for by the addition of 1 μg/ml Geneticin (Invitrogen, Carlsbad, Calif.). 10 days after the addition of Geneticin the cells were sorted based on EYFP fluorescence using a fluorescence activated cell sorter.

Transfection of the d-siRNAs was performed as follows. 750,000 cells were incubated in cytomix buffer (25 mM HEPES (pH 7.6), 120 mM KCl, 10 mM $K_2HPO_4$, 5 mM $MgCl_2$, 0.15 mM $CaCl_2$, 2 mM EGTA, 1.9 mM ATP, 4.7 mM Glutathione), 10 μg of ECFP (Clontech laboratories, Palo Alto Calif.), pGL3 (Promega, Madison, Wis.), and 1 ug of the relevant d-siRNA for 10 minutes at room temperature while shaking. The cells were electroporated with an ECM 830 square wave 8 well electoporator (BTX, Holliston, Mass.). Cells were immediately plated onto a 25 mm, No°2 coverslip and allowed to recover for 48 hours before imaging or lysis for western blot analysis.

Confocal and Total Internal Reflection Microscopy

The localization of the mitosis biosensor was examined using a CFP/YFP custom built spinning disc confocal microscope. An argon-ion laser (120 mW; Melles Griot, Carlsbad, Calif.) provided 514 nm light for excitation of the biosensor. Laser light homogenized with a rotating diffuser (Physical Optics, Torrance, Calif.) was coupled into a Yokogawa spinning disc head (Perkin Elmer, Boston, Mass.) mounted on an Olympus microscope. Exposure of the RBL-FMBs to laser light was controlled by a Sutter Lambda 10-2 filter wheel (Sutter Instrument, Novato, Calif.). 530 nm emitted light was detected with a 530 long pass interference filter (Chroma Technology, Brattleboro, Vt.) mounted in a Sutter Lambda 10-2 filter wheel (Sutter Instrument, Novato, Calif.). Images were captured every 15 minutes with an Orca II cooled CCD camera (Hamamatsu, Bridgewater, N.J.). The shutters, filter wheel, and camera were controlled by Metamorph software (Universal Imaging, Downington, Pa.).

TIRF microscopy was carried out as described previously (Tengholm et al., Science's Stke. 2003 PL4 (2004)). Briefly, an argon-ion laser provided 514-nm laser light for excitation of the biosensor (Lexel Laser, Fremont, Calif.). Exposure of the RBL-FMBs to laser light was controlled by a Uniblitz shutter (Vincent, Rochester, N.Y.). Laser light homogenized with a rotating diffuser (Physical Optics, Torrance, Calif.) was refocused onto a dove prism at an angle yielding total internal reflection (>61° C. for a glass-water interface at 37° C.). The excitation light could also be redirected to the back of the microscope and down to the sample via appropriate dichroic mirrors (Chroma Technology, Brattleboro, Vt.) for epi-illumination. Fluorescence was recorded at 530 nm with bandpass interference filters (30-50 nm half-bandwidth; Chroma Technology, Brattleboro, Vt.) mounted in a Sutter Lambda 10-2 filter wheel (Sutter Instrument, Novato, Calif.). Images were captured every 2 minutes with a cooled CCD camera (Micromax; Roper Scientific, Tuscon, Azir.). The shutters, filter wheel, and camera were controlled by Metamorph software (Universal Imaging, Downington, Pa.).

Both systems were heated with an ASI 400 Air Stream Incubator (Nevtek, Burnsville, Va.). The cells were perfused with fresh growth media saturated with 10% CO2 that was heated with an inline solution heater (Warner Instruments, Hamden, Conn.).

Data Analysis

Metamorph software (Universal Imaging, Downington Pa.) was used for data image analysis. Fluorescence intensity was recorded over the entire stack of images by drawing regions of interest over each mitotic cell. Background correction was performed by subtracting the intensity of a background region of identical size next to each cell to account for the somewhat uneven background in the field of view over the time of the data collection. Background corrected intensity values were exported to a Microsoft Excel file and plotted. NEB was determined as the time just prior to the dramatic increase in fluorescence intensity. Anaphase onset is defined as the time point immediately preceding the second smaller increase in fluorescence. NER was determined as the point in time when fluorescence intensity starts to decrease back to baseline levels.

Immunofluorescence

Mitotic index was determined as previously described (Jordan et al., PNAS 56:816-825 (1996)). Briefly, 15,000 RBL-FMB cells plated in 8 well Labtek chambers (Nalge Nunc, Naperville, Ill.) and exposed to paclitaxel (Sigma Aldrich, St Louis) for 20 hours. The cells were fixed and permeablized with −20° C. cold methanol for 5 minutes at −20° C. They were blocked with 10% fetal calf serum in PBS for 10 minutes at RT. Alpha Tubulin was detected with a mouse monoclonal antibody clone GTU-88 (Sigma Aldrich, St. Louis Mo.). DNA was stained with Hoescht 33342 (Molecular Probes, Eugene, Oreg.). Only cells that were clearly in metaphase or anaphase were counted as a percentage of the total. The cells were imaged with a Zeiss epifluorescence microscope (Carl Zeiss, Germany).

Western Blot Analysis

Cells were lysed 48 hours after transfection with the d-siRNAs by vortexing in cold lysis buffer (0.42 M NaCl, 100 mM Tris pH 7.9, 0.5% Triton X-100, 1 mM EDTA, 1 mM EGTA) supplemented with protease inhibitors (aprotonin 1 µg/ml, 0.2 mM phenylmethylsulfonyl fluoride, pepstatin, leupeptin, and chymostatin, all at 0.2 µg/ml). Lysates were subjected to SDS-PAGE and transferred to polyvinylidene difluoride (PVDF; Amersham, Piscataway, N.J.). Blots were probed with α-Mad2 (1; 1000; a kind gift of Dr Guowei Fang), or anti-actin (1:400, Santa Cruz, Santa Cruz, Calif.). Secondary antibodies conjugated to horseradish peroxidase (Amersham, Piscataway, N.J.) were used at 1:2500. The Immun-Star HRP chemiluminescent detection kit (Bio-Rad, Hercules, Calif.) was used for HRP detection. Films were scanned and protein level was quantified using Adobe Photoshop (Adobe, San Jose, Calif.). Regions of the same size were drawn around the bands corresponding to Mad2 and the background subtracted average intensities were recorded. These data were normalized for protein amount with the actin band intensities. Mad2 protein levels were compared in cells treated with the Mad2 d-siRNA versus the control GL3 d-siRNA.

Example 1

Design of the Live-Cell Biosensor Polypeptide

A mitosis biosensor polypeptide composed of three components—a reversible plasma membrane (PM) targeting domain, a fluorescent polypeptide, and a nuclear localization signal (NLS)—was produced as described above. In this example, the MBP included a reversible PM targeting domain fused to the $NH_2$ terminus of a yellow fluorescent protein (EYFP), which was in turn fused to the $NH_2$ terminus of a nuclear localization signal (EYFP-NLS, Clontech laboratories, Palo Alto Calif.) (FIG. 1).

A plasma membrane (PM) targeting motif based on polybasic residues was added at the N-terminus of an YFP-NLS (yellow fluorescent protein—nuclear localization signal) construct, as described in greater detail in the Examples section. The structure of YFP was adapted from Rekas et al., J. Biol. Chem. 50:573-578 (2002). It was hypothesized that a nuclear localization signal would ensure the biosensors localization to the nucleus during the G1, S, and G2 phases (interphase) of the cell cycle. Accordingly, upon nuclear envelope breakdown (NEB) at the onset of prometaphase, the plasma membrane binding domain would cause the reversible translocation of the biosensor to the plasma membrane where the fluorescence could be monitored by TIRF microscopy.

Figure 2:
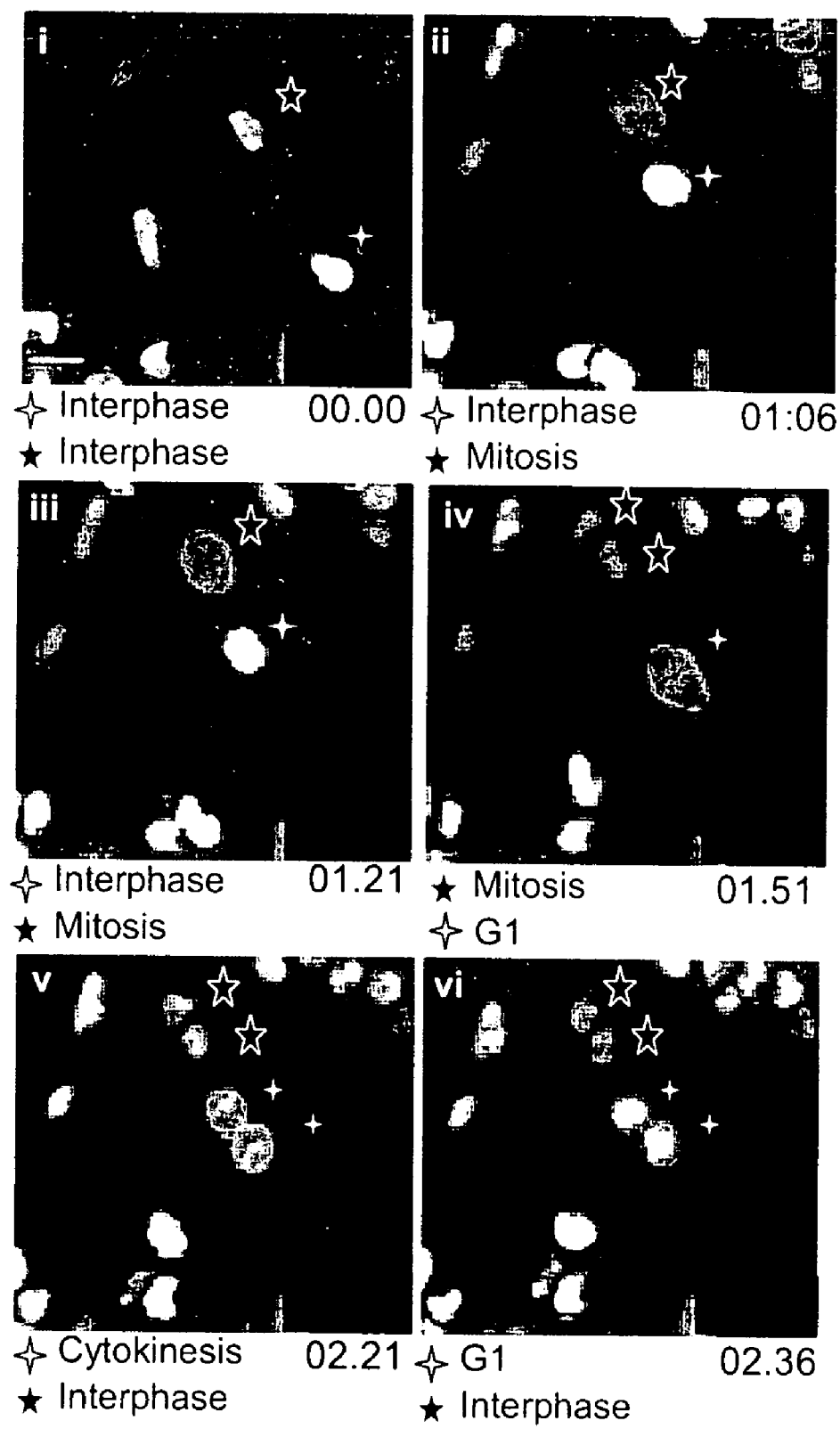
FIG. 2 shows a series of confocal images of RBL-FMB cells during interphase and mitosis (stars mark individual cells). The time elapsed (hours:minutes) between images is provided in the lower right hand corner of each image.

Confocal microscopy was first used to monitor the location of the biosensor during the cell cycle in a rat basophilic leukemia cell line that constitutively expressed the biosensor (RBL-FMBs). As hypothesized, the biosensor was found to reside in the nucleus during interphase, and upon NEB indicating onset of mitosis, the biosensor rapidly translocated to the plasma membrane (FIG. 2, panels i-iv). During telophase and cytokinesis, when the nuclear envelope reforms around the daughter chromatids at the end of mitosis, the biosensor translocated back into the nucleus where it resided until the subsequent mitosis (FIG. 2, panels v-vi).

Example 2

Location of the Biosensor Monitored by TIRF Microscopy

Figure 3:
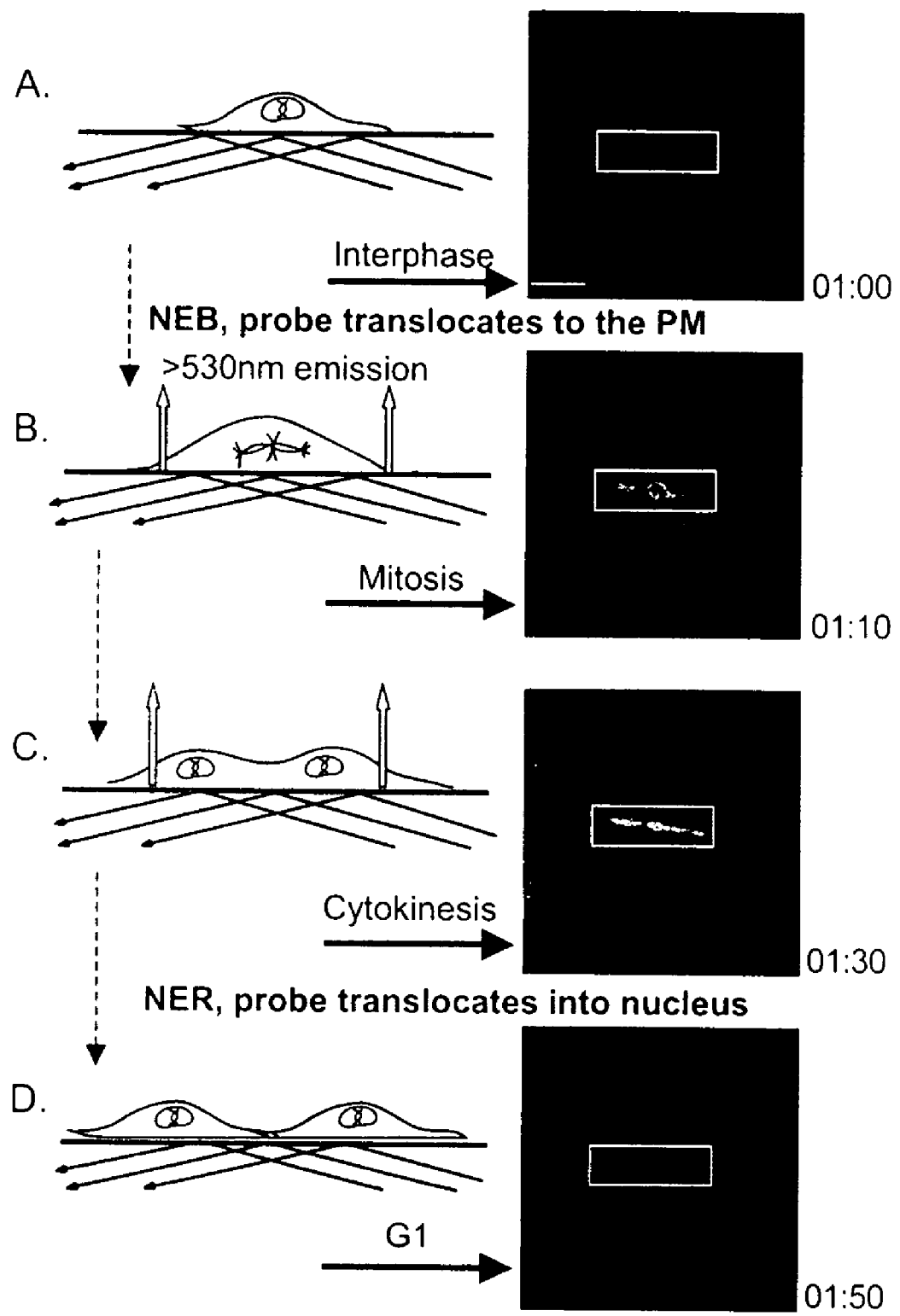
FIG. 3 is a series of schematics (left side of panels A-D) and photographs (right side of panels A-D) showing localization of the biosensor monitored by TIRF microscopy. The left side of panels A-D is a schematic representation of the mitosis monitoring system. The right side of panels A-D are TIRF images of a RBL-FMB cell in the cell cycle phase corresponding to the schematic in the left panel. The time elapsed (hours:minutes) between images is in the lower right hand corner. Scale bars represent 20 µm.

To determine if the change in fluorescence at the membrane could be monitored by TIRF microscopy, the same live cell imaging setup used in the confocal experiments above was adapted to a prism-based CFP/YFP TIRF system (FIG. 3). During interphase, no significant plasma membrane fluorescence was measured with TIRF, however, after NEB there was a large increase in plasma membrane fluorescence (FIG. 3, panels B and C). This fluorescence was maintained until the nuclear envelopes of the two daughter cells reformed and the biosensor translocated back into the nucleus. Translocation into the nucleus was paralleled by a rapid loss in plasma membrane fluorescence measured by TIRF microscopy (FIG. 3, panel D). Because the MBP is monitored by the less toxic TIRF microscopy, we were able take images at a rate of up to 2 images per minute, compared to every 5 minutes with epifluorescence imaging and 15 with confocal imaging, thus greatly increasing the temporal resolution. Similarly, since the MBP is only excited for approximately 30 minutes (when the cells are in mitosis) during the course of the experiments no significant bleaching of the YFP was seen.

Example 3

Monitoring Many Mitotic Events Using Wide Field TIRF

Figure 4:
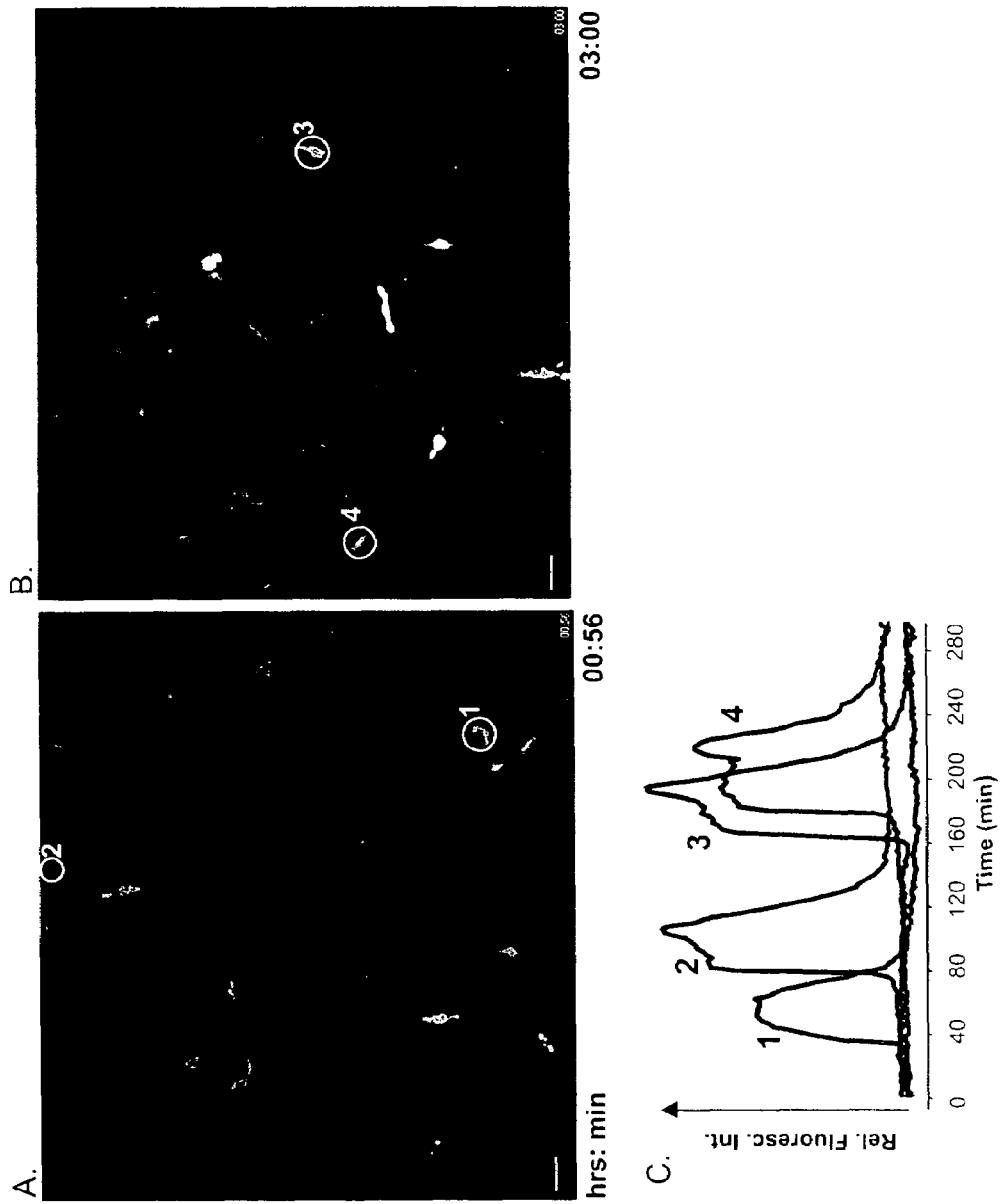
FIG. 4 shows the monitoring of multiple mitotic events in one experiment. Panels A and B are two frames from a 5 hour wide field TIRF time lapse experiment. Circles represent a location where a cell underwent mitosis. Scale bar represents 50 µm. The time (hours:minutes) is in the lower right hand corner. Panel C is a plot of fluorescence intensity versus time for the four corresponding cells circled in Panels A and B.

Based on the findings in the example above, a wide field TIRF microscope was used to monitor many mitotic events in the same experiment. FIG. 4 (panels A and B) shows two planes of a 5-hour TIRF experiment that was recorded through a 10× objective in which 70 cells proceeded through mitosis. In order to analyze these traces, the background was measured and subtracted from the fluorescence over time at each location where a mitotic event occurred. Typical examples of such individual traces are shown in FIG. 4, panel C. These results confirm that the time-period between nuclear envelope breakdown and reformation can indeed be measured from the TIRF signal, enabling an accurate quantification of the duration of mitosis.

Example 4

Detecting NEB, Anaphase, and NER with the Mitosis Biosensor

Figure 5:
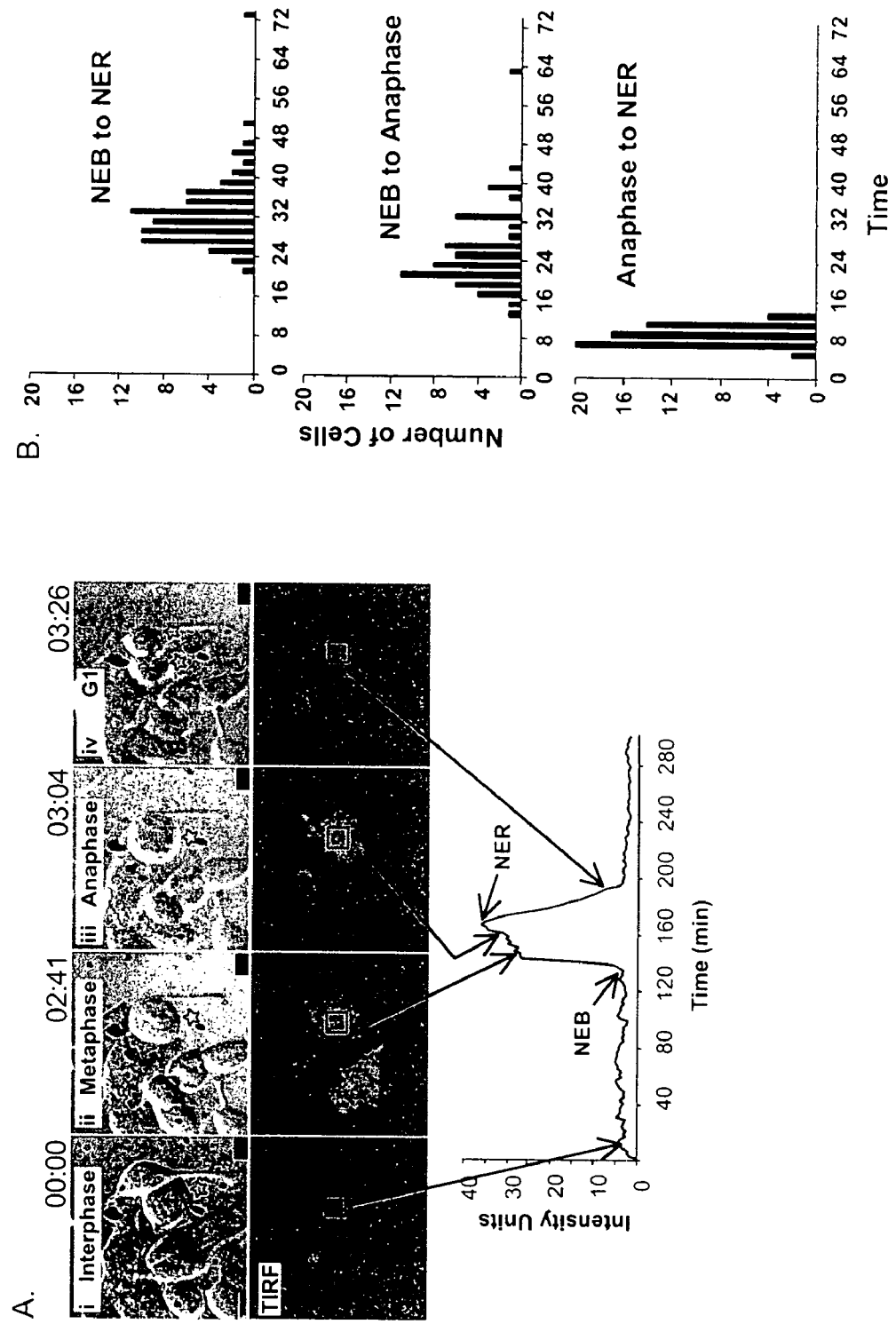
FIG. 5 shows the results of RBL-FMB cells imaged in parallel with TIRF (lower panels) and transmitted light (upper panels) microscopy through a 40× objective. The stars in the transmitted light images in Panel A mark the monitored cell. The region used to quantify the membrane fluorescence is shown in the TIRF images. The corresponding time point on the fluorescence intensity trace is shown below the image in Panel A with an arrow. Scale bars represent 10 μm. Panel B shows measurements of the time between nuclear envelope breakdown (NEB) to nuclear envelope reformation (NER), NEB to anaphase, and anaphase to NER based on the intensity traces obtained in the experiment represented in FIG. 4 Panels A-B.

In 58 of the 70 cells (83%) that went through mitosis in the experiment above, a second smaller increase in plasma membrane fluorescence was noted 6 to 12 minutes prior to the decrease in plasma membrane fluorescence (NER). Since previous studies in HeLa cells concluded that anaphase onset occurs approximately 8 minutes before nuclear import is reactivated, it was hypothesized that the second smaller increase in the TIRF signal was a reflection of anaphase onset. This was addressed by simultaneously monitoring plasma membrane fluorescence with TIRF and cell morphology with transmitted light (FIG. 5, panel A). Consistent with the hypothesis, anaphase onset occurred immediately preceding the second marked increase of plasma membrane fluorescence that lasted until nuclear envelope reformation (NER) when the probe started to translocate back into the nucleus. This same correlation was observed in 11 out of the 15 cells (73%) monitored at this higher resolution. One explanation for the observed second increase in fluorescence intensity at anaphase is that the cells are moving closer to the adhesion surface. Another possibility is that the membrane interaction of the biosensor increases during anaphase, and the resulting increased membrane translocation causes the fluorescence increase. Regardless of the mechanism, the second peak of the fluorescence intensity trace provides a useful measurement of the time between anaphase onset and NER.

A detailed analysis of three independent experiments in which 217 mitotic events were tracked is provided in FIG. 5, panel B, and Table 1. The first finding was the consistency by which mitosis is executed in these cells. In 80% of the cells, the timing of mitosis fell between 26 and 38 minutes. To be precise, this measures the onset of prometaphase where NEB occurs and the end of telophase where the nuclear import machinery is reactivated. Even though these experiments were measured at different days with different cell preparations, the mean mitotic clock time was consistently 32 minutes. When the intensity traces had the second spike in plasma membrane fluorescence, (n=152, 70% of cells), the mean time between NEB and anaphase was 23±7 minutes and the mean time between anaphase and NER was 8 minutes±2 minutes. These results show that the mitotic machinery in these cells has a marked precision and consistency in keeping time even in unsynchronized cell cultures. These data also convincingly demonstrate the reproducibility of the TIRF based method to monitor mitosis, as well as a significant improvement in the ability to monitor more mitotic events in much less time.

TABLE 1

Fidelity of the TIRF-Based Mitosis Monitoring System

| | NEB-NER | | | | | NEB-anaphase | | | | | Anaphase-NER | | | | |
|---|---|---|---|---|---|---|---|---|---|---|---|---|---|---|---|
| Expt. | No. | Med. | Ave. | S.D. | SEM | No. | Med. | Ave. | S.D. | SEM | No. | Med. | Ave. | S.D. | SEM |
| 1 | 70 | 30 | 31.9 | 7.6 | 0.9 | 58 | 22 | 24.5 | 8.2 | 1.1 | 58 | 8 | 8.0 | 2.1 | 0.3 |
| 2 | 69 | 30 | 31.3 | 6.0 | 0.7 | 49 | 22 | 22.7 | 4.7 | 0.7 | 49 | 8 | 8.0 | 2.0 | 0.3 |
| 3 | 78 | 30 | 31.7 | 7.4 | 0.8 | 45 | 22 | 23.5 | 6.9 | 1.0 | 45 | 8 | 8.0 | 2.3 | 0.3 |

Data from 3 experiments taken on 3 different days are shown.
All units are minutes with the exception of cell number.
No. = cell number,
Med. = median,
Ave. = average,
S.D. = standard deviation,
SEM = standard error of the mean.

Example 4

Detecting the Durations of Prometaphase, Metaphase, NEB to Anaphase and NER to NER Using the Mitosis Biosensor and Wide Field Epifluorescence Microscopy The advantages of the total internal reflection fluorescence (TIRF) microscopy based mitosis monitoring system described above include the high signal to noise ratio as well as the low phototoxicity, which makes it suitable for long term live cell imaging. The system provides the ability to observe tens to hundreds of cells proceeding through mitosis with high temporal resolution in a single experiment versus one or two cells with conventional high magnification DIC microscopy.

Figure 6:
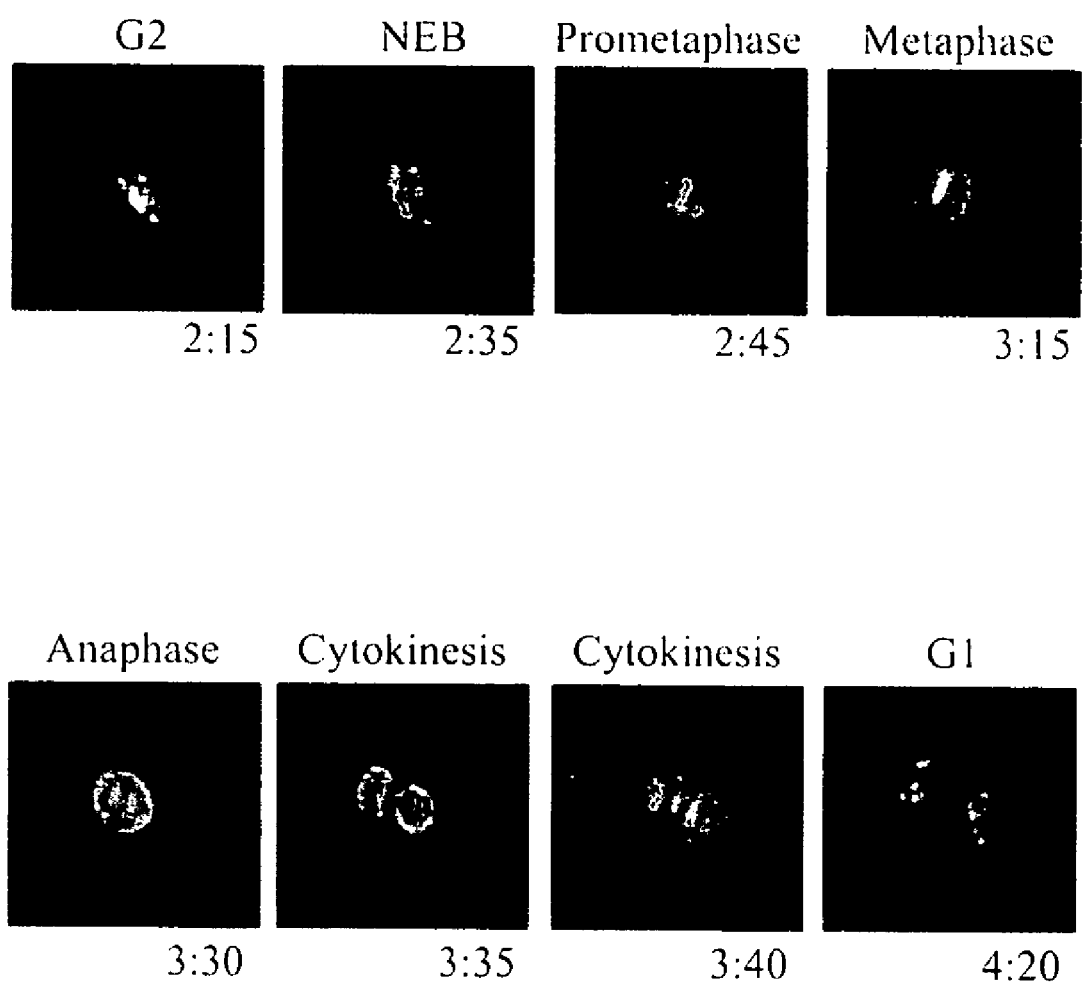
FIG. 6 is a series of photographs showing the localization of the mitosis biosensor in Hela cells during cell division. Hela cells were imaged with the automated imaging system Axon ImageXpress 5000A equipped with a 10× objective.

However, the throughput of the mitosis monitoring system needed to be increased to enable genome wide screens to dissect which gene products control the mitotic clock. To increase the throughput needed for a compound or siRNA library screen the MBP can be used with currently available automated imaging systems. Hela cells were transfected in a 96-well format with the MBP and imaged with an Axon ImageXpress 5000A (Axon Instruments, Union City, Calif.) equipped with a live cell imaging chamber over a course of 12 hours. As shown in FIG. 6, when monitored with the automated imaging system the MBP has a dramatic localization pattern, clearly localizing to the plasma membrane and the condensed chromatin of mitotic cells upon nuclear envelope breakdown. The MBP remains associated with both the plasma membrane and the condensed chromatin until after anaphase onset when the nuclear envelopes are reformed around the daughter chromatin (FIG. 6) The results show that because of the MBP's association with the chromatin, use of an automated epifluorescent imaging systems enables visualization of nuclear envelope breakdown, prometaphase, metaphase, anaphase, cytokinesis, and nuclear envelope reformation, in tens to hundreds of cells in a single well of a 96-well plate.

Figure 7:
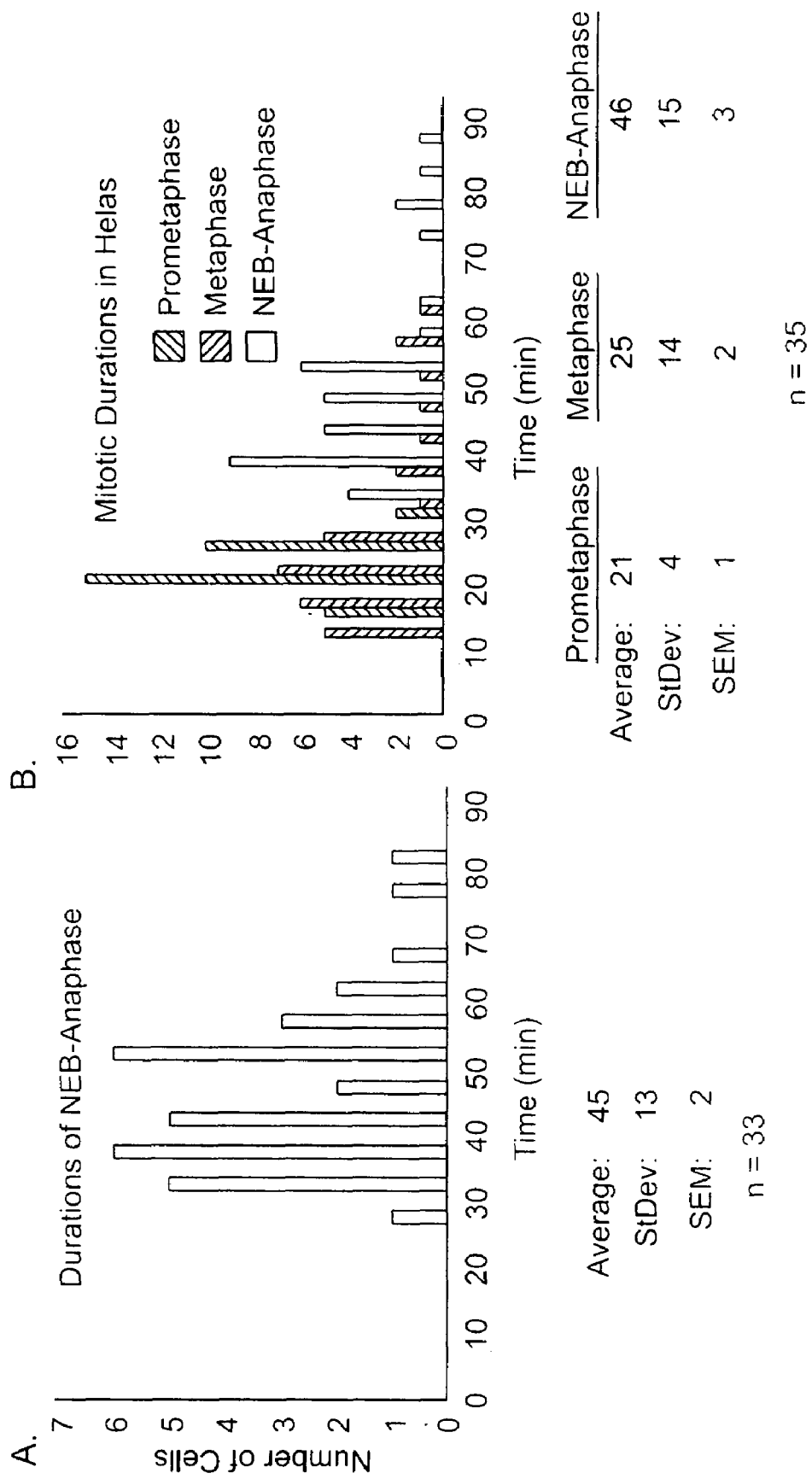
FIG. 7 is a series of graphs showing mitotic durations in Hela cells with the mitosis biosensor and automated imaging systems. Panel A is a histogram representing the duration of NEB to anaphase in 33 Hela cells imaged overnight using the Axon ImageXpress. The average time, standard deviation (Stdev), and standard error of the mean (SEM) are shown below the graph. Panel B is a histogram representing the duration of prometaphase, metaphase, and NEB-anaphase from 35 cells in an experiment independent from Panel A. The average, standard deviation, and standard error of the mean are shown below the histogram for the phase of mitosis.

To ensure that mitotic timing was not affected because of the light used for imaging, the duration between nuclear envelope breakdown (NEB) to anaphase of 30 to 35 cells in two separate experiments was analyzed (FIG. 7). The resulting duration of 45±3 min and 46±2 min in the two experiments is nearly identical to what has been shown experimentally with the same cells using high magnification DIC microscopy. In addition, the results show that because the MBP shows the location of the chromatin the duration of prometaphase (NEB to metaphase), metaphase (metaphase to anaphase), as well as NEB to anaphase can be measured (FIG. 7).

Figure 8:
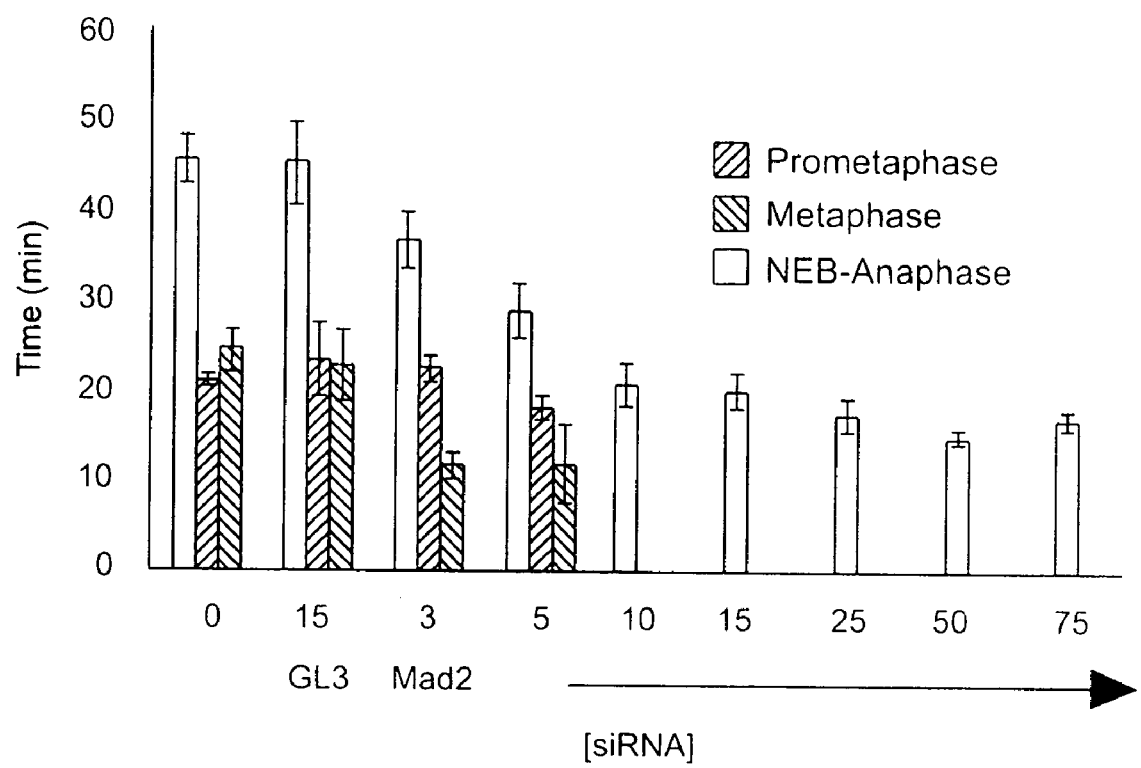
FIG. 8 is graph showing that knockdown of Mad2 with d-siRNA results in a decrease in mitotic duration. Hela cells were transfected with d-siRNA targeting either the firefly luciferase gene GL3 as a control or Mad2 at the above transfection concentrations. The duration of prometaphase, metaphase, and NEB-anaphase was quantified.

To minimize the light-induced phototoxicity from the imaging, the framing rate was optimized at one image every 5 minutes. To ensure that the temporal resolution achieved with this framing rate was sufficient to observe subtle effects on mitotic timing, d-siRNAs targeted to the critical mitotic regulator Mad2 were added and their effect on the mitotic times was observed. When Hela cells constitutively expressing the probe were transfected with the Mad2 d-siRNA, effects on mitotic duration (e.g. reduction in timing) were seen when concentrations as low as 3 nM of d-siRNA were used in the transfection (FIG. 8). Mitotic durations decreased even further when larger amounts of d-siRNA were used in the transfection until the RNA became nonspecifically toxic to the cells at concentrations above 75 nM. The results show that the MBP allows observation of reductions of mitotic durations with high confidence using the automated imaging system. In addition, the results also show that the MBP allows use of a range of concentrations of d-siRNAs and enables observation of significant effects on mitotic duration.

The results show that it is now possible to monitor with the throughput needed for compound or siRNA screens, the timing between prometaphase, metaphase, and NEB to anaphase. The localization of the MBP also allows visualization of the timing and the affect on mitosis of a perturbation such as the knockdown of a gene product with RNAi, or overexpression of the gene product with an expression cassette.

Example 5

A Loss of Function Screen for Mitotic Regulators

A set of 96 d-siRNAs targeting members of each subclass (Ras, Rho, Ran, Rab, and Arf) of the small GTPase superfamily were generated. These d-siRNAs were subsequently transfected into Hela cells constitutively expressing the MBP in a 96-well plate format. Approximately 36 hours after transfection, cells were imaged at a maximum of 1 image every 5 minutes using the Axon ImageXpress 5000A (Molecular Devices, Sunnyvale Calif.) for a minimum of 10 hours. The individual tiff files were then organized into time-lapse sequences and mitotic cells were easily identified by the localization pattern of the MBP.

Figure 9A:
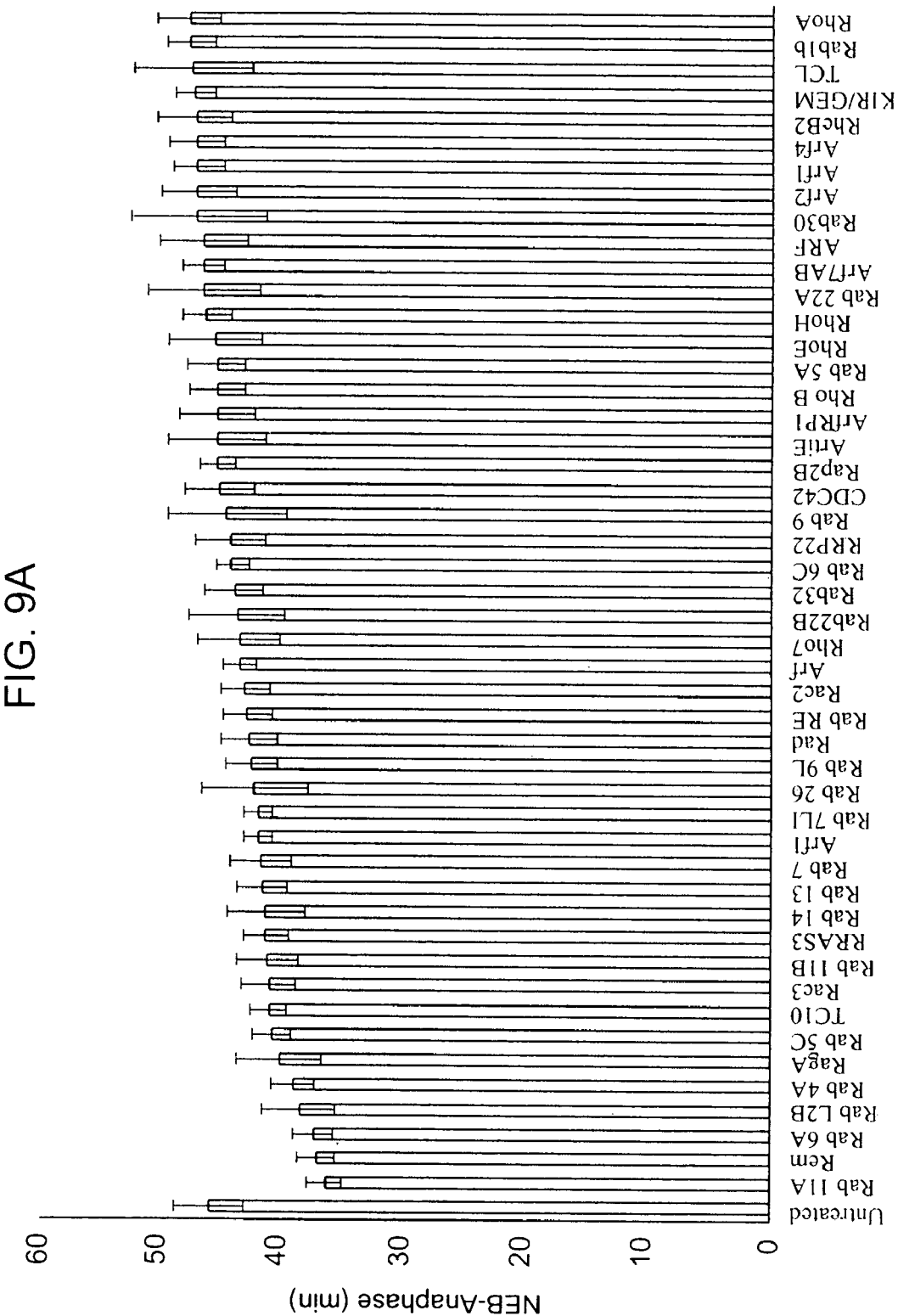
FIGS. 9A-9B shows the duration of NEB-anaphase in Hela cells transfected with d-siRNAs targeting 96 small GTPases. Hela cells were plated and transfected with the d-siRNAs in a 96-well format and imaged overnight with an automated imaging system. NEB and anaphase was scored and the duration of time in between was recorded for an average of 10 cells per well. Bars marked Rab 11A, REM, and Rab 6A (FIG. 9A) indicate the wells in which the mitotic duration was significantly less then control transfected cells (p value≦0.05). Bars marked RhoD through Rab3B (FIG. 9B) indicate the wells in which the mitotic duration was significantly greater then control transfected cells (p value≦0.05).
Figure 9B:
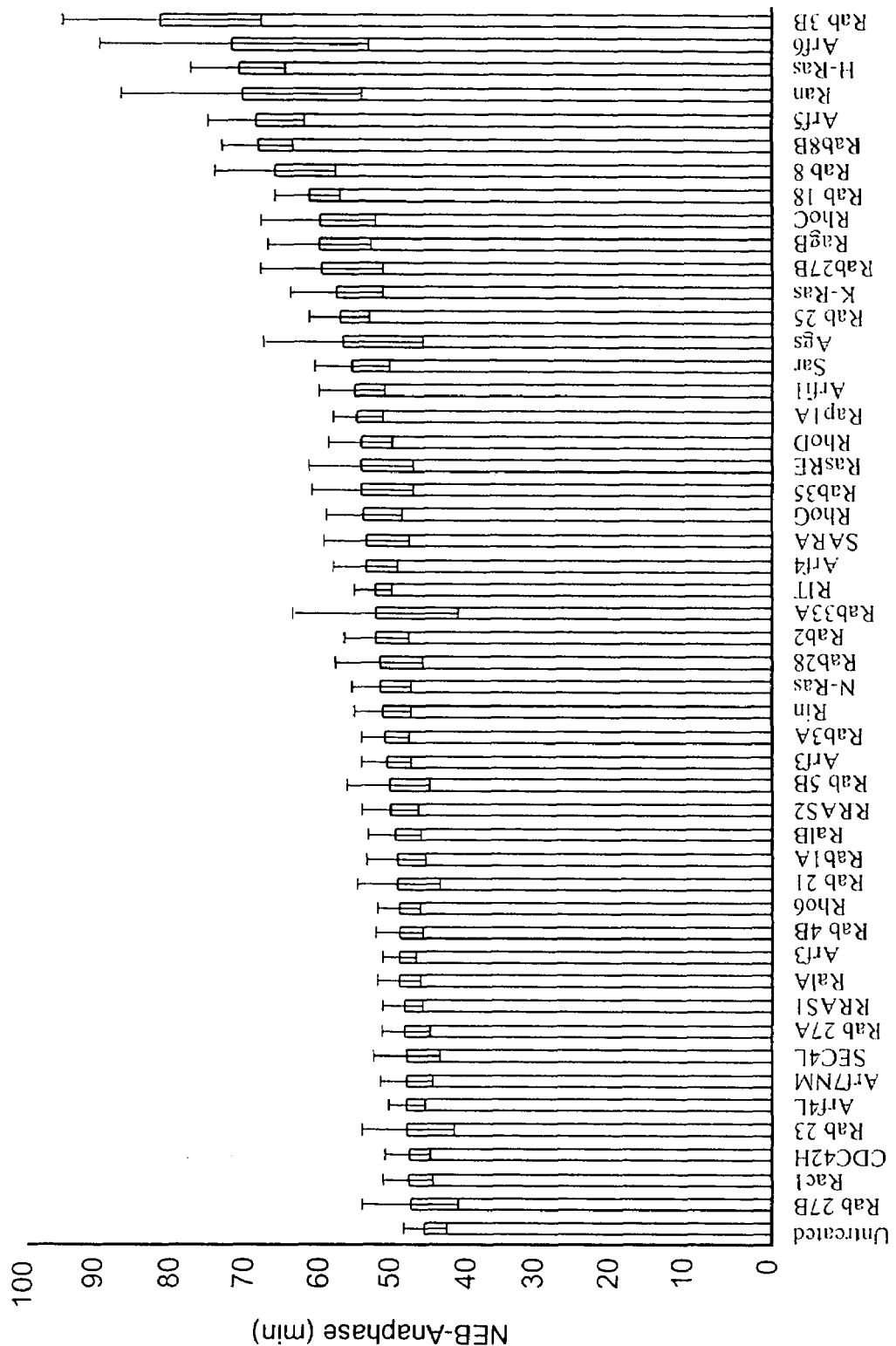
Figure 11:
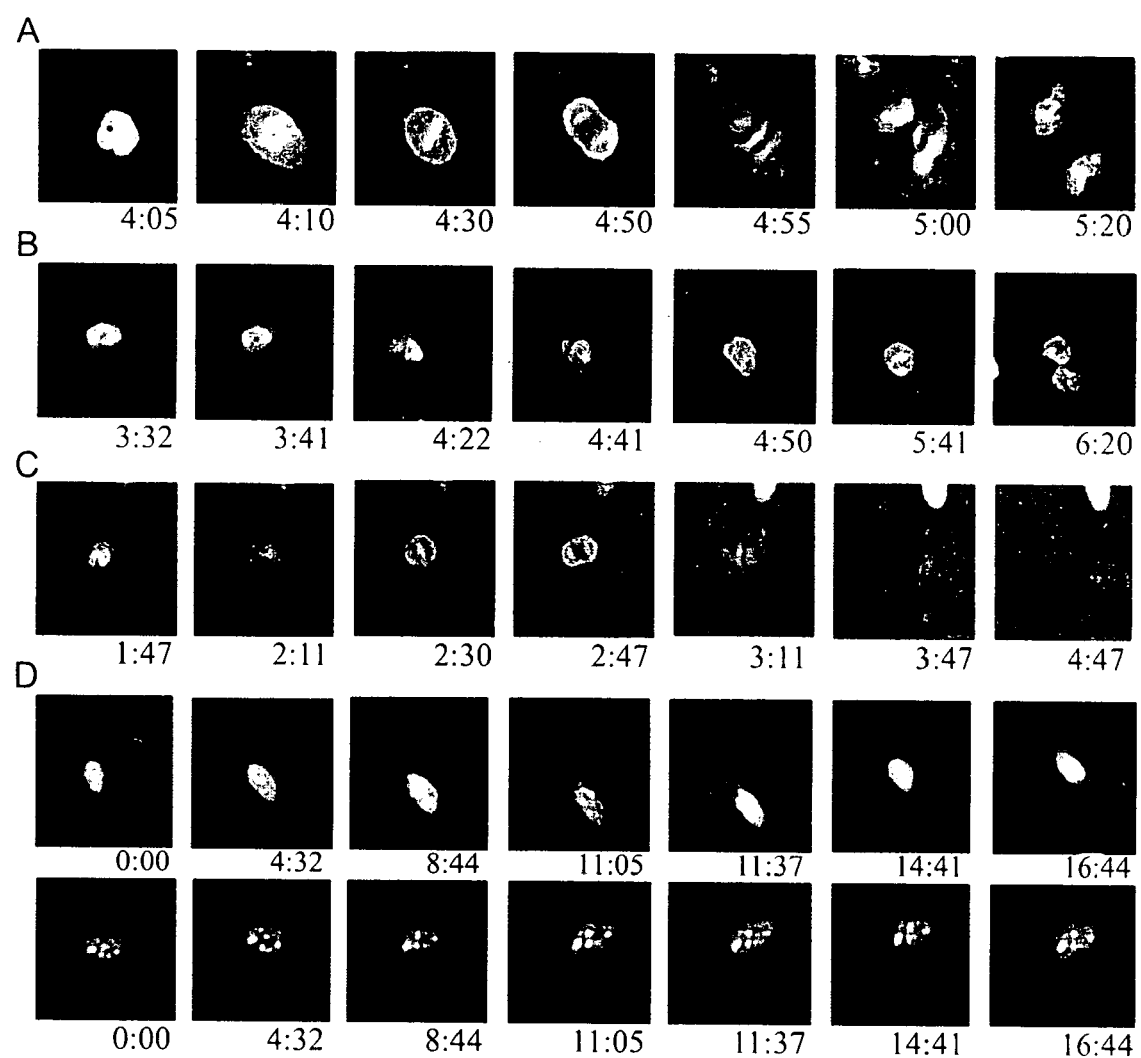
FIG. 11 is a series of photographs showing that the mitosis biosensor polypeptide is able to detect defects in nuclear envelope breakdown (NEB), nuclear envelope reformation (NER), cytokinesis, and nucleo-cytoplasmic transport. Panel A shows A control transfected cell representing a normal NEB (≦5 min duration), cytokinesis and NER. Panel B shows a cell transfected with a constitutively active version of the small GTPase Rap1a with defects in NEB. Complete NEB takes over 70 minutes in this cell as compared to less than 5 minutes for a control transfected cell. Panel C shows a cell transfected with a constitutively active version of the small GTPase Rab18. Due to the plasma membrane localization of the mitosis biosensor, failures in these cells to complete cytokinesis can be observed by the fluorescence at the cleavage furrow. Similarly, the probe fails to translocate back into the nucleus showing defects in functional NER. Panel D, top row, shows a representative cell (top panels) transfected with the constitutively active version of the small GTPase Rap1A. At 3 different points during the time-lapse the mitosis biosensor loses exclusive localization to the nucleus and "leaks" into the cytoplasm. The bottom row represents an untransfected cell in the same well of the experiment with no defect in nucleo-cytoplasmic transport.
Figure 15:
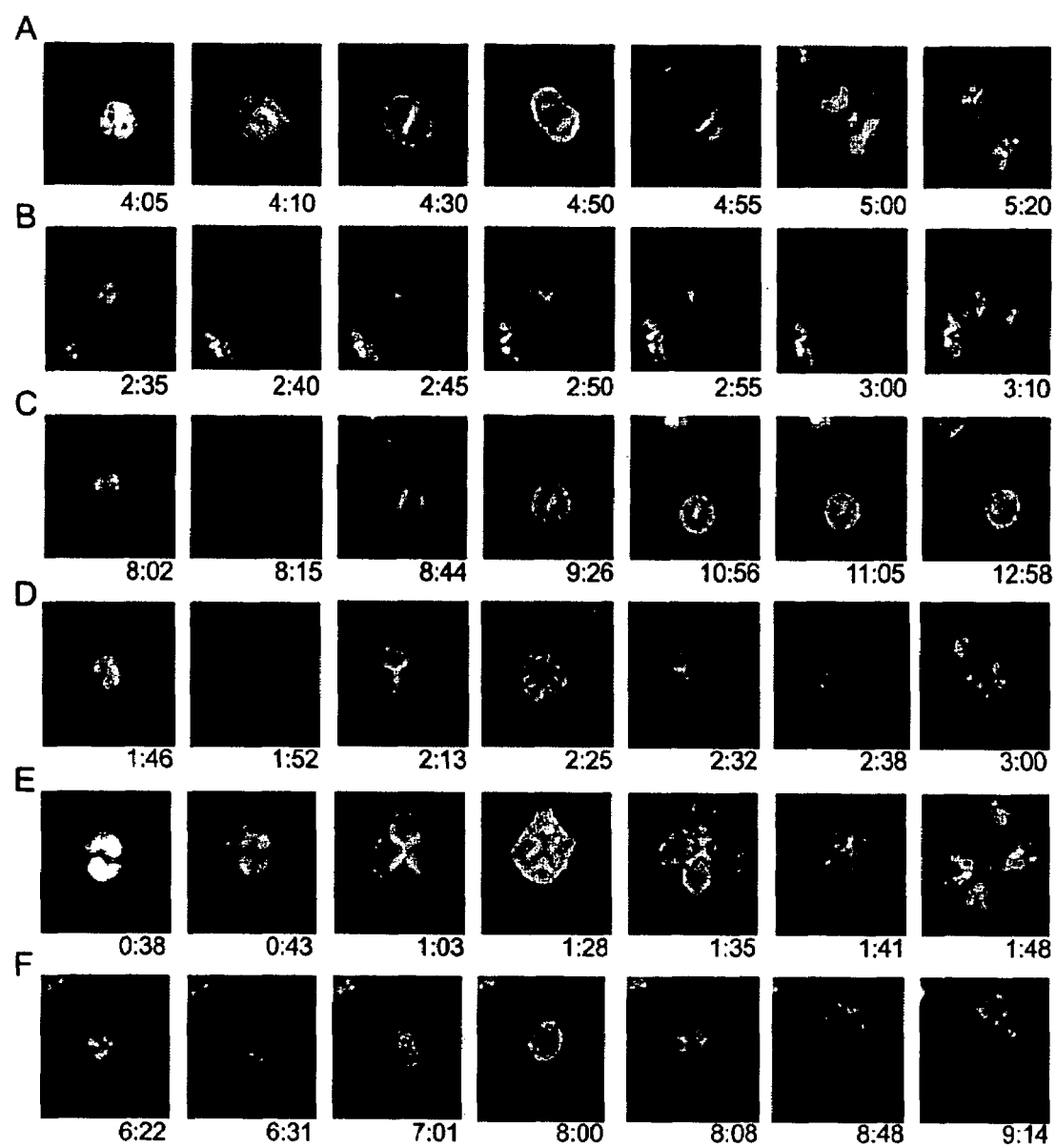
FIG. 15 is a series of photographs showing that chromatin organization defects can be recorded by the live cell fluorescent mitosis biosensor polypeptide. Panel A shows a control transfected cell representing a normal mitotic event as reported by the mitosis biosensor polypeptide. Panel B shows that a Mad2 d-siRNA transfected cell is unable to organize the chromatin at the metaphase plate, which results in an undefined metaphase. Panel C shows a cell transfected with a d-siRNA targeting the small GTPase Ran. The cell appears to organize the chromatin at the metaphase plate, but is unable to maintain organization and anaphase onset does not occur before the end of the time series. Panel D shows a cell transfected with a d-siRNA targeting the small GTPase N-Ras results in a tripolar spindle. Panel E shows that a dominant negative mutant form of Rab 3B transfected into a cell results in a tetrapolar spindle. Panel F shows transfection with a dominant negative version of Ran results in a monopolar spindle so that the cell undergoes anaphase and cytokinesis resulting in a binucleate and anucleate daughter cells.

FIGS. 9A and 9B show the duration of NEB to anaphase in Hela cells transfected with the 96 d-siRNAs targeting the small GTPases. 75 of the 96 small GTPases did not have a significant effect on the timing of the mitotic clock. This result is encouraging because it eliminated the possibility that knockdown of the small GTPases would result in global non-specific effects on cell health resulting in increased mitotic times. 18 of the 96 small GTPases did result in a significant increase in the duration of NEB to anaphase ($p \leq 0.05$ using the Student's t test), (FIGS. 9A and 9B). As predicted from previously published results, knockdown of Ran had dramatic effects on mitotic timing increasing its duration from 45 min (NEB-anaphase anaphase for a normal cell) to 70 min. These data show that the other 17 small GTPases are necessary for the mitotic clock to function with the appropriate timing The dramatic localization pattern of the mitosis biosensor allows us to not only observe effects on mitotic durations but also to observe changes in mitotic morphologies. FIG. 15 shows the dramatic phenotypes that were detected with the MBP using the Axon ImageXpress 5000A. In untreated or control transfected cells, the establishment of a metaphase plate is clear based on the congregation of the chromosome-localized fluorescence in the middle of the cell. Because the mitosis biosensor localizes to the plasma membrane during mitosis, effects on cytokinesis, as well as defects in nuclear envelope breakdown, reformation, and integrity, were also observable (FIG. 11).

Example 6

Taxol has a Graded Effect on Mitotic Timing

Given this precision in mitotic timing, sub-maximal doses of the mitosis inhibitor TAXOL™ (paclitaxel) were examined to determine whether the drug has a graded or an all-or-none effect on delaying the exit from mitosis. TAXOL™ is a potent broad-spectrum anticancer agent that is particularly useful in the treatment of ovarian, breast, and lung carcinomas (Wang et al., Cancer, 88:2619-2628 (2000)). It acts by binding and stabilizing microtubules, which results in mitotic arrest (Wang et al., Cancer 88:2619-28 (2000); Jordan et al., PNAS 90:9552-6 (1993); Jordan et al., Cancer Res. 56:816-25 (1996); Sorger et al., Curr. Opin. Cell Biol. 9:807-814 (1997)). Immunofluorescence studies in HeLa cells suggested that TAXOL™ has a microtubule stabilization effect in the nM concentration range (Jordan et al., 1993).

The sensitivity of the TIRF based mitosis monitoring system allowed for detection of a significant shift in the timing between NEB and NER, from an average time of 31.8 minutes to 35.6 minutes (p=0.014) when concentrations of TAXOL™ as low as 10 pM were applied to the cells (FIG. 12, Panel A, and Table 2). This mitotic time increased as more TAXOL™ was added until the cells arrested for the duration of the experiment at 10 nM (FIG. 12, Panel A, and Table 2). In traces where it was possible to monitor the timing between NEB and anaphase, the pre-checkpoint mitosis phase was significantly prolonged while the post-checkpoint anaphase to NER phase showed smaller and ungraded effects (Table 2).

As a control, it was confirmed that the percentage of mitotic cells increased at higher taxol concentrations using conventional immunofluorescence experiments with the same RBL-FMBs (Jordan et al., 1993). RBL-FMB cells were treated with TAXOL™ at varying doses for 20 hours, fixed and stained with an antibody that recognizes alpha-tubulin and the DNA stain Hoeschst 33342 (Molecular Probes, Eugene, Oreg.) (FIG. 12, Panel B). With these two stains mitotic spindles are easily recognized and the mitotic index can be quantified. Nevertheless, the effects at low TAXOL™ concentrations went unseen in those experiments (FIG. 12, Panel B). Consistent with the first hypothesis, these results show that the mitotic clock is slowed down by TAXOL™ in a graded way by delaying anaphase onset. Furthermore, these studies also highlight the sensitivity of this approach and how it can be used to measure small changes in the mitotic clock at clinically relevant drug concentrations.

spindle checkpoint, the assay was then assessed for the ability to detect whether the mitotic checkpoint is only engaged when these RBL cells are perturbed or if it imposes a significant delay on mitosis even in unsynchronized and unperturbed cells. The mitotic control system in these cells could function in two ways: (i) it could be driven by a fast internal mitotic timer that gets stopped during each cell cycle at the checkpoint and waits for a checkpoint release to continue or, (ii) by a checkpoint that only significantly delays the internal mitotic timer if the chromosome assembly is disrupted. It has been shown previously that PtK1 cells entered anaphase 23 minutes±1 minute after the last kinetochore was attached to the spindle suggesting an active checkpoint in unperturbed cells (Reider et al., J. Cell Biol. 127:1301-1310 (1994)).

When an antibody recognizing Mad2 was microinjected into Ptk-1 cells, or primary human keratinocytes, early in mitosis the cells underwent premature anaphase onset suggesting the spindle checkpoint plays an important role in the normal timing of mitosis Gorbsky et al., J. Cell Biol. 141:1193-1205 (1998)). This issue was addressed directly by disabling the spindle checkpoint using RNAi to suppress the expression of Mad2 and observe any reduction in mitotic timing. Mad2, in conjunction with Bub1/Bub3, arrests cells in metaphase by inhibiting the ubiquitin ligase activity of the anaphase-promoting complex (APC), which is responsible for degrading securing (Yu et al., Curr. Opin. Cell Biol. 14:706-714 (2002); Fang et al., Genes. Dev. 12:1871-1883 (1998)). Mouse embryonic cells lacking Mad2 were unable to arrest at metaphase and the absence of this checkpoint resulted in chromosome missegregation, genetic instability, and apoptosis (Michel et al., Nature 409:355-359 (2001); Dobles et al., Cell 101:635-645 (2000)). Studies of arrested cells suggested that a dominant negative Mad2 can induce precocious anaphase onset (Mikhailov et al., Curr. Biol. 12:1979-1806 (2002); Canman et al., Cell Mot. Cyto. 52:61-65 (2002)).

TABLE 2

Analysis of RBL-FMB Cells Treated with Varying Levels of TAXOL ™

| | NEB-NER | | | | | NEB-anaphase | | | | | Anaphase-NER | | | | |
|---|---|---|---|---|---|---|---|---|---|---|---|---|---|---|---|
| [Taxol] | No. | Med. | Ave. | S.D. | SEM | No. | Med. | Ave. | S.D. | SEM | No. | Med. | Ave. | S.D. | SEM |
| 0 | 217 | 30 | 31.8 | 8.1 | 1.0 | 152 | 22 | 23.7 | 7 | 1.1 | 152 | 8 | 8.0 | 2.1 | 0.3 |
| 0.01 | 104 | 34 | 35.6 | 12.3 | 1.2 | 65 | 26 | 28.4 | 14.2 | 1.8 | 65 | 8 | 8.4 | 2.6 | 0.3 |
| 0.1 | 41 | 36 | 38.1 | 9.6 | 1.5 | 23 | 26 | 29.6 | 10.1 | 1.6 | 23 | 8 | 8.8 | 3.0 | 0.5 |
| 1 | 140 | 38 | 40.0 | 9.9 | 0.8 | 100 | 28 | 29.8 | 9.6 | 1.0 | 100 | 10 | 10.3 | 3.6 | 0.5 |
| 3 | 36 | 50 | 62.8 | 36.4 | 6.1 | 14 | 34 | 44.6 | 25.8 | 6.9 | 14 | 8 | 10.3 | 4.4 | 1.2 |
| 4 | 25 | 70 | 89.7 | 50.4 | 10.1 | 18 | 60 | 77.7 | 49.3 | 11.6 | 18 | 10 | 9.8 | 2.7 | 0.6 |
| 5 | 37 | 102 | 112.2 | 59.6 | 9.8 | 26 | 114 | 107.4 | 57.5 | 11.3 | 26 | 12 | 11.3 | 4.0 | 0.8 |
| 6 | 53 | 186 | 194.5 | 66.5 | 9.1 | 25 | 175 | 183.3 | 69.9 | 14.0 | 25 | 11 | 13.3 | 6.7 | 1.3 |
| 7.5 | 48 | 195 | 202.1 | 63.6 | 9.2 | 24 | 166 | 171.1 | 65.0 | 13.3 | 24 | 12 | 12.3 | 5.0 | 1.0 |
| 8 | 63 | 189 | 192.7 | 47.4 | 6.1 | 46 | 178 | 180.3 | 46.4 | 6.8 | 46 | 12 | 12.1 | 3.8 | 0.6 |

The results are compared with those of untreated cells.
All units are minutes with the exception of cell number.
No. = cell number,
Med. = median,
Ave. = average,
S.D. = standard deviation,
SEM = standard error of the mean.

Example 7

Mad2 Knockdown Results in Shortened but Precise Mitoses

Since the TIRF based mitosis monitoring system detected extremely subtle and graded effects of TAXOL™ on the spindle checkpoint, the assay was then assessed for the ability In three separate experiments the expression of rat Mad2 (rMAD2) was reduced by electroporating dicer processed siRNAs (d-siRNAs) into RBL-FMB cells. The resulting time in between NEB and NER was on average only 26.8, 25.9, 24.9 minutes compared to 32 minutes for control treated (GL3 d-siRNA) or untreated cells (p=0.00008), (FIG. 13, Panels A-B, and Table 3) (Meyers et al., Nature Biotech.

Figure 13:
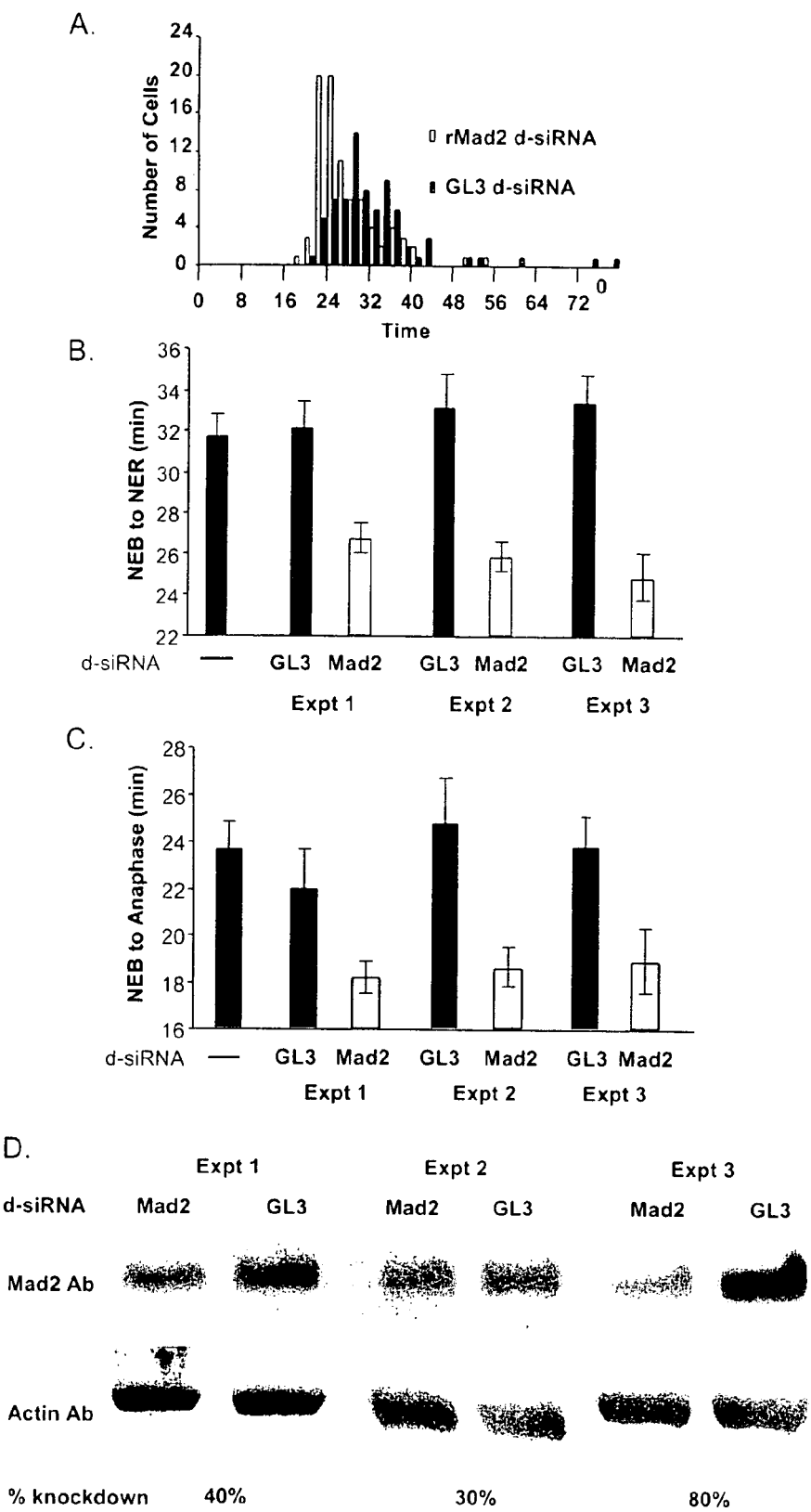
FIG. 13 summarizes data showing that a decrease in Mad2 activity with d-siRNA results in a shortened mitosis. RBL-FMB cells were transfected with dicer processed double stranded RNAs (d-siRNAs) corresponding to the rMad2 gene, or firefly luciferase (GL3) control d-siRNAs and imaged 48 hours later. Panel A shows histograms from experiment #1 (Table 3) comparing Mad2 d-siRNA treated RBL-FMBs (open bars) versus GL3 treated RBL-FMBs (black bars). The time between NEB and NER from all three experiments is compared in Panel B and NEB to anaphase in Panel C. See Table 3 for detailed analysis. Panel D shows a Western Blot analysis of Mad2 expression in d-siRNA treated RBL-FMB cells. RBL-FMB cells were transfected with d-siRNAs targeting Mad2 and the control firefly luciferase gene GL3. 48 hours post transfection the cells were lysed and prepared for western blot analysis. Protein levels were normalized with an actin antibody.

21:324-328 (2003). As expected, the reduced time was a result of a decrease in the timing between NEB and anaphase (FIG. 13 Panel C, and Table 3). Mad2 protein knockdown was verified by western analysis (FIG. 13, Panel D). The measurements show that even a partial knockdown of Mad2 leads to full inactivation of the spindle checkpoint suggesting an all or none activation/inactivation mechanism via Mad2. Furthermore, these RNAi measurements directly demonstrate that Mad2 has a critical role in the spindle checkpoint as has been suggested previously by other approaches (Gorbsky et al., 1998; Mikhailov et al., 2002; Canman et al., 2002). These data show that the first hypothesis is correct and that during a normal cell cycle the spindle checkpoint imposes a marked delay onto the mitotic clock even in these relatively fast mitotic cells.

localized throughout the cell, having no nuclear envelope to contain or exclude them, and the mitotic biosensor rapidly translocates to the plasma membrane of the cell.

Figure 17B:
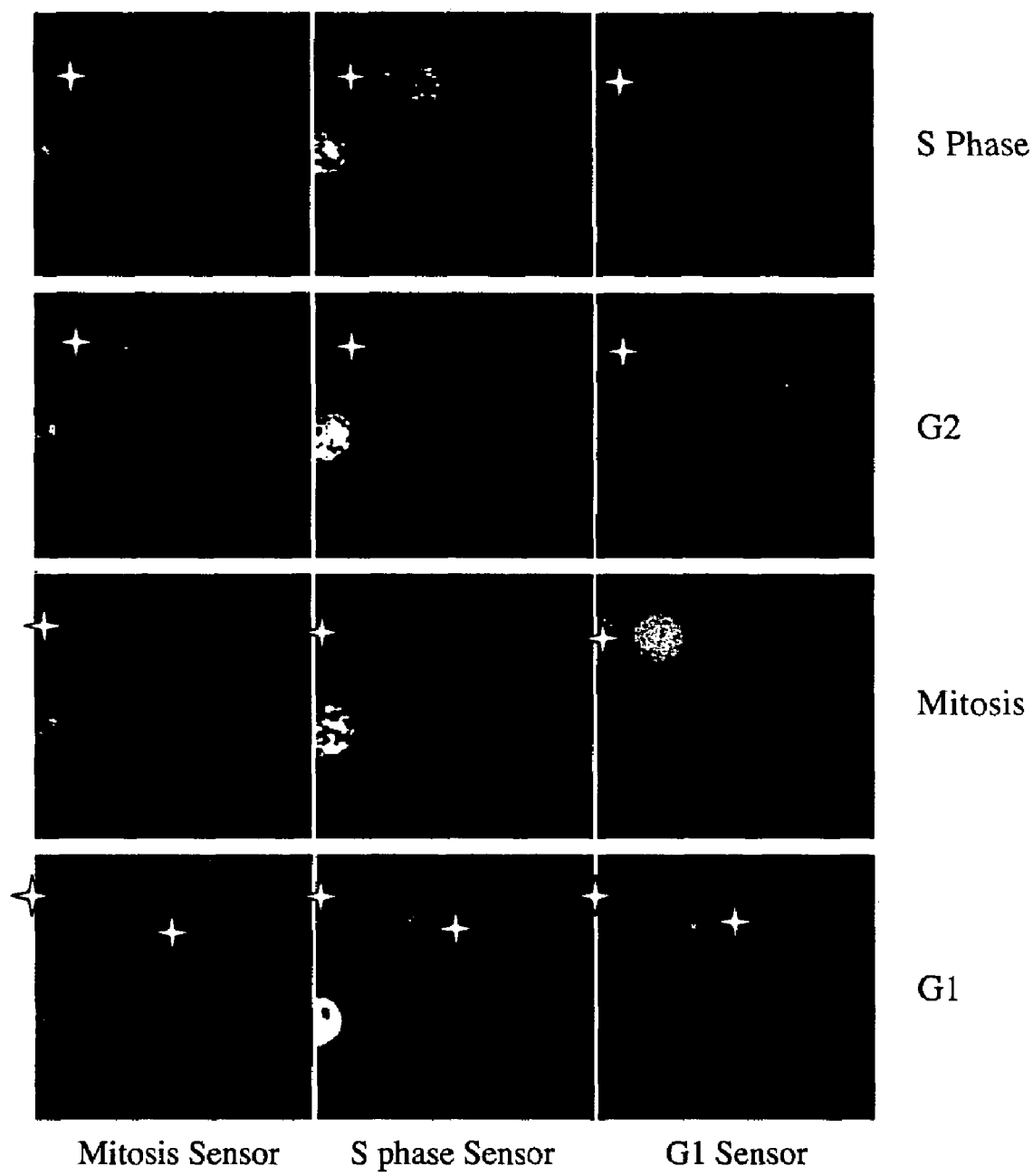
FIG. 17B is a set of images from overnight video microscopy of HeLa cells transiently transfected with three biosensor polypeptides, MBP, G1BP, and SBP. The cell marked with a star begins the experiment in S phase, indicated by punctate S phase sensor and cytoplasmic G1BP fluorescence pattern. When the cell enters G2, the localization of the G1BP fluorescence pattern remains in the cytoplasm but the SBP fluorescence pattern changes to a homogeneous nuclear stain, excluding the nucleoli.

The fluorescence patterns provided by the three biosensor polypeptides (e.g., as captured on an imaging system) make it possible to successfully score the timing of all four phases of the cell cycle. FIG. 17B provides exemplary fluorescent images taken with different filters so as to capture the different patterns provided by the different emission spectra of the MBP (mitosis sensor) SBP (S phase sensor) and G1BP (G2 sensor) according to the invention.

Figure 17C:
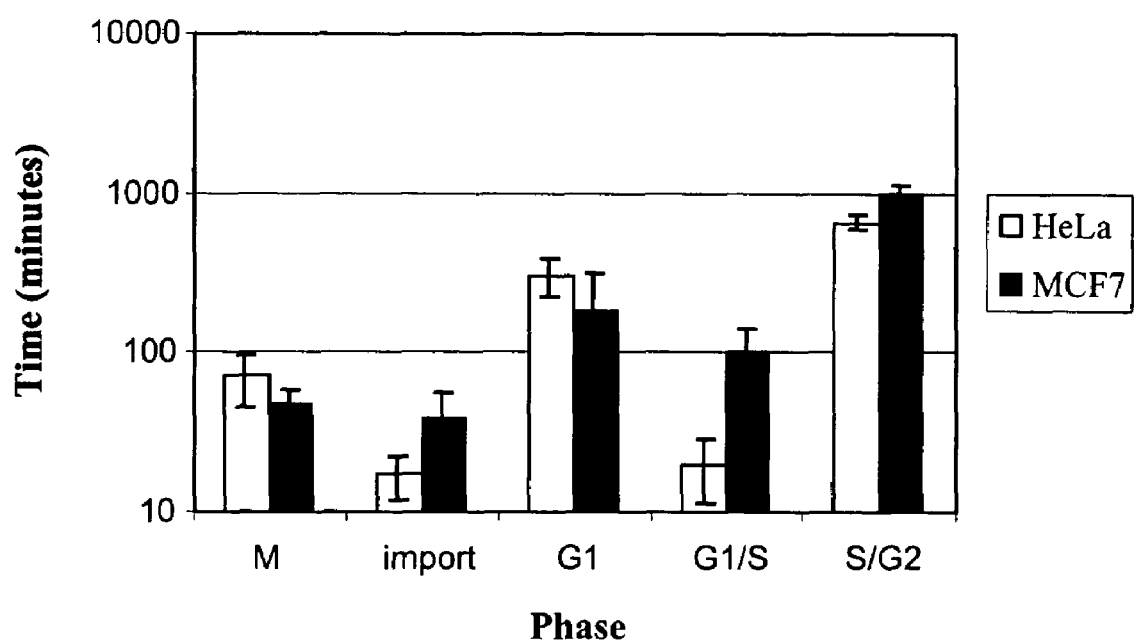
FIG. 17C is a graph of cell cycle timing in HeLa and MCF7 cells as determined using the G1 biosensor. The MCF7 cell line differs from the HeLa cell line in timing of the phases as well as in the transport of the G1 biosensor from the cytoplasm to the nucleus and the export of the G1 biosensor back into the cytoplasm (G1/S). Data on the timing in these two cell lines was collected from stacks of images taken over a duration of 15 hours with frames taken every 15 minutes on the Axon ImageXpress 5000A using a 10× objective.

FIG. 17C shows that the G1BP fluorescence pattern alone can provide for detection of a measurable variation between the duration of cell cycle phases in different cell types (MCF7

TABLE 3

Mitotic Times are Consistently Reduced as a Result of Mad2 Knockdown

| | NEB-NER | | | | | NEB-anaphase | | | | | Anaphase-NER | | | | |
|---|---|---|---|---|---|---|---|---|---|---|---|---|---|---|---|
| | No. | Med. | Ave. | S.D. | SEM | No. | Med. | Ave. | S.D. | SEM | No. | Med. | Ave. | S.D. | SEM |
| Untreated Expt. 1 | 218 | 30 | 31.8 | 8.1 | 1.0 | 152 | 22 | 23.7 | 7.0 | 1.1 | 152 | 8 | 8.0 | 2.1 | 0.3 |
| GL3 d-siRNA | 74 | 30 | 32.2 | 10.2 | 1.2 | 51 | 20 | 22.1 | 10.4 | 1.6 | 51 | 8 | 8.9 | 2.7 | 0.4 |
| Mad2 d-siRNA Expt. 2 | 86 | 26 | 26.8 | 6.5 | 0.7 | 39 | 17 | 18.2 | 4.7 | 0.7 | 39 | 8 | 7.9 | 2.8 | 0.4 |
| GL3 d-siRNA | 41 | 30 | 33.2 | 9.9 | 1.6 | 25 | 22 | 24.8 | 9.1 | 1.9 | 25 | 8 | 7.6 | 2.0 | 0.4 |
| Mad2 d-siRNA Expt. 3 | 62 | 26 | 25.9 | 5.8 | 0.7 | 31 | 20 | 18.6 | 4.7 | 0.8 | 31 | 6.0 | 7.4 | 2.6 | 0.5 |
| GL3 d-siRNA | 43 | 32 | 33.5 | 7.7 | 1.2 | 17 | 24 | 23.8 | 5.8 | 1.3 | 17 | 8 | 7.4 | 1.8 | 0.4 |
| Mad2 d-siRNA | 38 | 24 | 24.9 | 6.6 | 1.1 | 23 | 18 | 18.9 | 6.6 | 1.4 | 23 | 8 | 7.8 | 1.9 | 0.4 |

Detailed analysis of three independent experiments in which RBL-FMB cells were transfected with d-siRNAs targeting Mad2 or firefly luciferase (GL3) as a control. The results are compared with the results obtained for untreated cells.
All units are minutes with the exception of cell number.
No. = cell number,
Med. = median,
Ave. = average,
S.D. = standard deviation,
SEM = standard error of the mean.

Example 8

Monitoring Cell Cycle Timing in Human Cells using the Fluorescent Biosensor Polypeptides As described in the specification above, the three different biosensor polypeptides of the invention can be used in conjunction to assess various cell cycle phases. Each of the biosensor polypeptides provide distinct fluorescent patterns that can be used to monitor the cell cycle and determine the duration of one or more phases of cell cycle as demonstrated in FIG. 16.

For example, all three biosensors can be expressed in a single cell to provide for analysis of the complete cell cycle. FIG. 17A provides a schematic of the patterns provided during the cell cycle by the MBP, G1BP and SBP biosensors. In G1, the mitotic (MBP), G1 (G1BP) and S (SBP) phase biosensors are each localized to the nucleus. As the cell enters S phase the MBP remains in the nucleus while the G1BP translocates into the cytoplasm and the SBP forms foci throughout the nucleus but excluded from the nucleoli. When the puncta from the SBP disappear in late S phase and the cell enters G2, this SBP biosensor again localizes homogenously in the nucleus. Throughout S phase and G2, the G1BP localizes to the cytoplasm while the MBP remains nuclear. After NEB (in mitosis), the G1 (G1BP) and S (SBP) phase biosensors are and HeLa cells). The results show that the biosensor-based strategy is capable of monitoring cell cycle timing throughout all phases of the cell cycle in tens to hundreds of unsynchronized individual cells in a single experiment.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of monitoring a cell-cycle phase of a mammalian cell, the method comprising:
culturing a mammalian cell comprising
a mitosis biosensor polypeptide (MBP) comprising a plasma membrane targeting domain, a nuclear localization signal and a fluorescent label,
a G1 phase biosensor polypeptide (G1BP) comprising a fluorescent label, and
a S phase biosensor polypeptide (SBP) comprising a fluorescent label,
under conditions suitable for proliferation of the mammalian cell, wherein each of the fluorescent labels of the G1BP, SBP, and MBP emit different fluorescence emission spectra; and
detecting a MBP fluorescence pattern and at least one of
a) G1BP fluorescence pattern established by a nuclear localized fluorescence and a cytoplasmic localized fluorescence; and
b) SBP fluorescence pattern established by formation of fluorescence puncta in a nuclear region of the mammalian cell and disappearance of fluorescence,
wherein nuclear envelope breakdown (NEB) is characterized by MBP fluorescence localized to a plasma membrane, indicating a mitosis phase of the cell cycle, and nuclear envelope reformation (NER) is characterized by MBP fluorescence localized to a nucleus, indicating interphase of the cell cycle.

2. The method according to claim 1, wherein prior to said detecting the cells are fixed.

3. The method according to claim 1, wherein a G1BP fluorescence pattern established by nuclear localized fluorescence is indicative of G1 phase of a cell cycle.

4. The method according to claim 1, wherein a G1BP fluorescence pattern established by cytoplasmic localized fluorescence is indicative of S or G2 phase of a cell cycle.

5. The method according to claim 1, wherein a SBP fluorescence pattern established by formation of fluorescence puncta in a nuclear region of the mammalian cell is indicative of S phase of a cell cycle.

6. The method according to claim 1, wherein detection of the MBP fluorescent pattern is by total internal reflection fluorescence (TIRF) microscopy.

7. The method according to claim 1, wherein cell cycle phase duration is determined in a plurality of cells and in parallel.

8. A method for determining duration of a cell-cycle phase of a mammalian cell, the method comprising:
culturing a mammalian cell comprising
a mitosis biosensor polypeptide (MBP) comprising a plasma membrane targeting domain, a nuclear localization signal and a fluorescent label,
a G1 phase biosensor polypeptide (G1BP) comprising a fluorescent label and
a S phase biosensor polypeptide (SBP) comprising a fluorescent label
under conditions suitable for proliferation of the mammalian cell, wherein each of the fluorescent labels of the G1BP, SBP, and MBP emit different fluorescence emission spectra; and
determining a time interval between at least two of
a) NEB,
b) NER,
c) formation of fluorescence puncta in a nuclear region of the mammalian cell,
d) disappearance of fluorescence puncta in a nuclear region of the mammalian cell,
e) appearance of fluorescence in a nuclear region of the mammalian cell, and
f) translocation of fluorescence from a nuclear region to a cytoplasmic region of the mammalian cell,
wherein a), b), c), d), e), and f) are established by detection of at least one of a MBP fluorescence pattern, a G1BP fluorescence pattern, or a SBP fluorescence pattern
wherein the time interval between NEB and NER is indicative of duration of a mitosis phase of the cell cycle and the time interval between NER and NEB is indicative of duration of interphase of the cell cycle.

9. The method according to claim 8, further comprising determining a time interval between at least two of NEB, prometaphase, metaphase, anaphase, cytokinesis, and NER, wherein NEB and NER are established by detection of a MBP fluorescence pattern and prometaphase, metaphase, anaphase, cytokinesis are established by detection of a condensed chromatin associated MBP fluorescence pattern.

10. The method according to claim 8, wherein the time interval is between NER and formation of fluorescence puncta in a nuclear region of the mammalian cell, which time interval is indicative of duration of G1 phase of a cell cycle.

11. The method according to claim 8, wherein the time interval is between formation of fluorescence puncta in a nuclear region of the mammalian cell and disappearance of fluorescence puncta in the nuclear region of the mammalian cell, which time interval is indicative of duration of S phase of a cell cycle.

12. The method according to claim 8, wherein the time interval is between disappearance of fluorescence puncta in a nuclear region of the mammalian cell and NEB, which time interval is indicative of duration of G2 phase of a cell cycle.

13. The method according to claim 8, wherein the time interval is between NER and translocation of fluorescence from a nuclear region to a cytoplasmic region of the mammalian cell, which time interval is indicative of duration of G1 phase of a cell cycle.

14. The method according to claim 8, wherein the time interval is between translocation of fluorescence from a nuclear region to a cytoplasmic region of the mammalian cell and disappearance of fluorescence puncta in a nuclear region of the mammalian cell, which time interval is indicative of duration of S phase of a cell cycle.

15. The method according to claim 8, wherein the time interval is between appearance of fluorescence in a nuclear region of the mammalian cell and translocation of fluorescence from a nuclear region to a cytoplasmic region of the mammalian cell, which time interval is indicative of duration of G1 phase of a cell cycle.

16. The method according to claim 8, wherein detection of the MBP fluorescent pattern is by total internal reflection fluorescence (TIRF) microscopy.

17. The method according to claim 8, wherein cell cycle phase duration is determined in a plurality of cells and in parallel.

18. The method according to claim 8, wherein said culturing is performed in the presence of a candidate agent, wherein an increase or decrease in the time interval as compared to a time interval in the absence of a candidate agent indicates the candidate agent modulates duration of a phase of a cell cycle of the mammalian cell.

* * * * *

UNITED STATES PATENT AND TRADEMARK OFFICE
CERTIFICATE OF CORRECTION

| | | |
|---|---|---|
| PATENT NO. | : 7,655,434 B2 | Page 1 of 1 |
| APPLICATION NO. | : 11/052001 | |
| DATED | : February 2, 2010 | |
| INVENTOR(S) | : Jones et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 829 days.

Signed and Sealed this

Twenty-eighth Day of December, 2010

David J. Kappos
*Director of the United States Patent and Trademark Office*

SEQUENCE LISTING

<160> NUMBER OF SEQ ID NOS: 17

<210> SEQ ID NO 1
<211> LENGTH: 4844
<212> TYPE: DNA
<213> ORGANISM: Artificial Sequence
<220> FEATURE:
<223> OTHER INFORMATION: expression vector

<400> SEQUENCE: 1

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgtcagatcc | gctagcatgg | 600 |
| agaaaaatc | taagcccaaa | acagtgtat | ggaagaggct | aaaatcacca | ttccggaaga | 660 |
| agaaagattc | agtaactgga | ccggtcgcca | ccatggtgag | caagggcgag | gagctgttca | 720 |
| ccggggtggt | gcccatcctg | gtcgagctgg | acggcgacgt | aaacggccac | aagttcagcg | 780 |
| tgtccggcga | gggcgagggc | gatgccacct | acggcaagct | gaccctgaag | ttcatctgca | 840 |
| ccaccggcaa | gctgcccgtg | ccctggccca | ccctcgtgac | caccttcggc | tacggcctgc | 900 |
| agtgcttcgc | ccgctacccc | gaccacatga | agcagcacga | cttcttcaag | tccgccatgc | 960 |
| ccgaaggcta | cgtccaggag | cgcaccatct | tcttcaagga | cgacggcaac | tacaagaccc | 1020 |
| gcgccgaggt | gaagttcgag | ggcgacaccc | tggtgaaccg | catcgagctg | aagggcatcg | 1080 |
| acttcaagga | ggacggcaac | atcctggggc | acaagctgga | gtacaactac | aacagccaca | 1140 |
| acgtctatat | catggccgac | aagcagaaga | acggcatcaa | ggtgaacttc | aagatccgcc | 1200 |
| acaacatcga | ggacggcagc | gtgcagctcg | ccgaccacta | ccagcagaac | acccccatcg | 1260 |
| gcgacggccc | cgtgctgctg | cccgacaacc | actacctgag | ctaccagtcc | gccctgagca | 1320 |
| aagaccccaa | cgagaagcgc | gatcacatgg | tcctgctgga | gttcgtgacc | gccgccggga | 1380 |
| tcactctcgg | catggacgag | ctgtacaagt | ccggactcag | atctcgagct | gatccaaaaa | 1440 |
| agaagagaaa | ggtagatcca | aaaagaaga | gaaggtaga | tccaaaaaag | aagagaaagg | 1500 |
| taggatccac | cggatctaga | taactgatca | taatcagcca | taccacattt | gtagaggttt | 1560 |
| tacttgcttt | aaaaaacctc | ccacacctcc | ccctgaacct | gaaacataaa | atgaatgcaa | 1620 |
| ttgttgttgt | taacttgttt | attgcagctt | ataatggtta | caaataaagc | aatagcatca | 1680 |
| caaatttcac | aaataaagca | tttttttcac | tgcattctag | ttgtggtttg | tccaaactca | 1740 |
| tcaatgtatc | ttaaggcgta | aattgtaagc | gttaatattt | tgttaaaatt | cgcgttaaat | 1800 |
| ttttgttaaa | tcagctcatt | ttttaaccaa | taggccgaaa | tcggcaaaat | cccttataaa | 1860 |
| tcaaaagaat | agaccgagat | agggttgagt | gttgttccag | tttggaacaa | gagtccacta | 1920 |
| ttaaagaacg | tggactccaa | cgtcaaaggg | cgaaaaaccg | tctatcaggg | cgatggccca | 1980 |

```
ctacgtgaac catcacccta atcaagtttt tgggggtcga ggtgccgtaa agcactaaat    2040
cggaacccta agggagcccc ccgatttaga gcttgacggg gaaagccggc gaacgtggcg    2100
agaaaggaag ggaagaaagc gaaaggagcg ggcgctaggg cgctggcaag tgtagcggtc    2160
acgctgcgcg taaccaccac acccgccgcg cttaatgcgc cgctacaggg cgcgtcaggt    2220
ggcacttttc ggggaaatgt gcgcggaacc cctatttgtt tattttcta aatacattca    2280
aatatgtatc cgctcatgag acaataaccc tgataaatgc ttcaataata ttgaaaaagg    2340
aagagtcctg aggcggaaag aaccagctgt ggaatgtgtg tcagttaggg tgtggaaagt    2400
ccccaggctc cccagcaggc agaagtatgc aaagcatgca tctcaattag tcagcaacca    2460
ggtgtggaaa gtccccaggc tccccagcag gcagaagtat gcaaagcatg catctcaatt    2520
agtcagcaac catagtcccg cccctaactc cgcccatccc gcccctaact ccgcccagtt    2580
ccgcccattc tccgccccat ggctgactaa ttttttttat ttatgcagag gccgaggccg    2640
cctcggcctc tgagctattc cagaagtagt gaggaggctt ttttggaggc ctaggctttt    2700
gcaaagatcg atcaagagac aggatgagga tcgtttcgca tgattgaaca agatggattg    2760
cacgcaggtt ctccggccgc ttgggtggag aggctattcg gctatgactg ggcacaacag    2820
acaatcggct gctctgatgc cgccgtgttc cggctgtcag cgcaggggcg cccggttctt    2880
tttgtcaaga ccgacctgtc cggtgccctg aatgaactgc aagacgaggc agcgcggcta    2940
tcgtggctgg ccacgacggg cgttccttgc gcagctgtgc tcgacgttgt cactgaagcg    3000
ggaagggact ggctgctatt gggcgaagtg ccggggcagg atctcctgtc atctcacctt    3060
gctcctgccg agaaagtatc catcatggct gatgcaatgc ggcggctgca tacgcttgat    3120
ccggctacct gcccattcga ccaccaagcg aaacatcgca tcgagcgagc acgtactcgg    3180
atggaagccg gtcttgtcga tcaggatgat ctggacgaag agcatcaggg gctcgcgcca    3240
gccgaactgt tcgccaggct caaggcgagc atgcccgacg cgaggatct cgtcgtgacc    3300
catggcgatg cctgcttgcc gaatatcatg gtggaaaatg gccgcttttc tggattcatc    3360
gactgtggcc ggctgggtgt ggcggaccgc tatcaggaca tagcgttggc tacccgtgat    3420
attgctgaag agcttggcgg cgaatgggct gaccgcttcc tcgtgcttta cggtatcgcc    3480
gctcccgatt cgcagcgcat cgccttctat cgccttcttg acgagttctt ctgagcggga    3540
ctctggggtt cgaaatgacc gaccaagcga cgcccaacct gccatcacga gatttcgatt    3600
ccaccgccgc cttctatgaa aggttgggct tcggaatcgt tttccgggac gccggctgga    3660
tgatcctcca gcgcggggat ctcatgctgg agttcttcgc ccaccctagg gggaggctaa    3720
ctgaaacacg gaaggagaca ataccggaag gaacccgcgc tatgacggca ataaaaagac    3780
agaataaaac gcacggtgtt gggtcgtttg ttcataaacg cggggttcgg tcccagggct    3840
ggcactctgt cgatacccca ccgagacccc attgggccaa atacgcccgc gtttcttcct    3900
tttccccacc ccaccccca gttcgggtg aaggcccagg gctcgcagcc aacgtcgggg    3960
cggcaggccc tgccatagcc tcaggttact catatatact ttagattgat ttaaaacttc    4020
attttaatt taaaaggatc taggtgaaga tccttttga taatctcatg accaaaatcc    4080
cttaacgtga gttttcgttc cactgagcgt cagaccccgt agaaaagatc aaaggatctt    4140
cttgagatcc tttttttctg cgcgtaatct gctgcttgca acaaaaaaa ccaccgctac    4200
cagcggtggt ttgtttgccg gatcaagagc taccaactct ttttccgaag gtaactggct    4260
tcagcagagc gcagatacca aatactgtcc ttctagtgta gccgtagtta ggccaccact    4320
```

```
tcaagaactc tgtagcaccg cctacatacc tcgctctgct aatcctgtta ccagtggctg    4380
ctgccagtgg cgataagtcg tgtcttaccg ggttggactc aagacgatag ttaccggata    4440
aggcgcagcg gtcgggctga acgggggtt cgtgcacaca gcccagcttg agcgaacga     4500 cctacaccga actgagatac ctacagcgtg agctatgaga aagcgccacg cttcccgaag    4560
ggagaaaggc ggacaggtat ccggtaagcg cagggtcgg aacaggagag cgcacgaggg    4620
agcttccagg gggaaacgcc tggtatcttt atagtcctgt cgggtttcgc cacctctgac    4680
ttgagcgtcg atttttgtga tgctcgtcag ggggcggag cctatggaaa aacgccagca    4740
acgcggcctt tttacggttc ctggccttt gctggccttt tgctcacatg ttctttcctg     4800
cgttatcccc tgattctgtg gataaccgta ttaccgccat gcat                    4844
```

<210> SEQ ID NO 2
<211> LENGTH: 308
<212> TYPE: PRT
<213> ORGANISM: Artificial Sequence
<220> FEATURE:
<223> OTHER INFORMATION: fluorescent fusion protein

<400> SEQUENCE: 2

```
Met Glu Lys Lys Ser Lys Pro Lys Asn Ser Val Trp Lys Arg Leu Lys
1               5                   10                  15

Ser Pro Phe Arg Lys Lys Asp Ser Val Thr Gly Pro Val Ala Thr
            20                  25                  30

Met Val Ser Lys Gly Glu Glu Leu Phe Thr Gly Val Val Pro Ile Leu
        35                  40                  45

Val Glu Leu Asp Gly Asp Val Asn Gly His Lys Phe Ser Val Ser Gly
    50                  55                  60

Glu Gly Glu Gly Asp Ala Thr Tyr Gly Lys Leu Thr Leu Lys Phe Ile
65                  70                  75                  80

Cys Thr Thr Gly Lys Leu Pro Val Pro Trp Pro Thr Leu Val Thr Thr
                85                  90                  95

Phe Gly Tyr Gly Leu Gln Cys Phe Ala Arg Tyr Pro Asp His Met Lys
            100                 105                 110

Gln His Asp Phe Phe Lys Ser Ala Met Pro Glu Gly Tyr Val Gln Glu
        115                 120                 125

Arg Thr Ile Phe Phe Lys Asp Asp Gly Asn Tyr Lys Thr Arg Ala Glu
    130                 135                 140

Val Lys Phe Glu Gly Asp Thr Leu Val Asn Arg Ile Glu Leu Lys Gly
145                 150                 155                 160

Ile Asp Phe Lys Glu Asp Gly Asn Ile Leu Gly His Lys Leu Glu Tyr
                165                 170                 175

Asn Tyr Asn Ser His Asn Val Tyr Ile Met Ala Asp Lys Gln Lys Asn
            180                 185                 190

Gly Ile Lys Val Asn Phe Lys Ile Arg His Asn Ile Glu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Tyr Gln Ser Ala Leu
225                 230                 235                 240

Ser Lys Asp Pro Asn Glu Lys Arg Asp His Met Val Leu Leu Glu Phe
                245                 250                 255

Val Thr Ala Ala Gly Ile Thr Leu Gly Met Asp Glu Leu Tyr Lys Ser
            260                 265                 270
```

Gly Leu Arg Ser Arg Ala Asp Pro Lys Lys Arg Lys Val Asp Pro
        275                 280                 285

Lys Lys Lys Arg Lys Val Asp Pro Lys Lys Lys Arg Lys Val Gly Ser
        290                 295                 300

Thr Gly Ser Arg
305

<210> SEQ ID NO 3
<211> LENGTH: 1614
<212> TYPE: DNA
<213> ORGANISM: Artificial Sequence
<220> FEATURE:
<223> OTHER INFORMATION: expression vector

<400> SEQUENCE: 3

```
atggcttcgt ggggatcccc gaagaagaag cgcaaagtac tggtaccggt cgccaccatg      60
gtgagcaagg gcgaggagct gttcaccggg gtggtgccca tcctggtcga gctggacggc     120
gacgtaaacg gccacaagtt cagcgtgtcc ggcgagggcg agggcgatgc cacctacggc     180
aagctgaccc tgaagttcat ctgcaccacc ggcaagctgc ccgtgccctg cccaccctc     240
gtgaccaccc tcggctacgg cctgcagtgc ttcgcccgct accccgacca catgaagcag     300
cacgacttct tcaagtccgc catgcccgaa ggctacgtcc aggagcgcac catcttcttc     360
aaggacgacg gcaactacaa gacccgcgcc gaggtgaagt tcgagggcga caccctggtg     420
aaccgcatcg agctgaaggg catcgacttc aaggaggacg gcaacatcct ggggcacaag     480
ctggagtaca actacaacag ccacaacgtc tatatcatgg ccgacaagca gaagaacggc     540
atcaaggtga acttcaagat ccgccacaac atcgaggacg gcagcgtgca gctcgccgac     600
cactaccagc agaacacccc catcggcgac ggccccgtgc tgctgcccga caaccactac     660
ctgagctacc agtccgccct gagcaaagac cccaacgaga gcgcgatca catggtcctg     720
ctggagttcg tgaccgccgc cgggatcact ctcggcatgg acgagctgta caagggcgaa     780
gggcaagggc aagggcaagg gccgggccgc ggctacgcgt atcgatccat gttcgaggcg     840
cgcctggtcc agggctccat cctcaagaag gtgttggagg cactcaagga cctcatcaac     900
gaggcctgct gggatattag ctccagcggt gtaaacctgc agagcatgga ctcgtcccac     960
gtctctttgg tgcagctcac cctgcggtct gagggcttcg acacctaccg ctgcgaccgc    1020
aacctggcca tgggcgtgaa cctcaccagt atgtccaaaa tactaaaatg cgccggcaat    1080
gaagatatca ttacactaag ggccgaagat aacgcggata ccttggcgct agtatttgaa    1140
gcaccaaacc aggagaaagt ttcagactat gaaatgaagt tgatggattt agatgttgaa    1200
caacttggaa ttccagaaca ggagtacagc tgtgtagtaa agatgccttc tggtgaattt    1260
gcacgtatat gccgagatct cagccatatt ggagatgctg ttgtaatttc ctgtgcaaaa    1320
gacggagtga attttctgc aagtggagaa cttggaaatg aaacattaa attgtcacag    1380
acaagtaatg tcgataaaga ggaggaagct gttaccatag atgaatgaa accagttcaa    1440
ctaacttttg cactgaggta cctgaacttc tttacaaaag ccactccact ctcttcaacg    1500
gtgacactca gtatgtctgc agatgtaccc cttgttgtag agtataaaat tgcggatatg    1560
ggacacttaa atactactt ggctcccaag atcgaggatg aagaaggatc ttag          1614
```

<210> SEQ ID NO 4
<211> LENGTH: 536
<212> TYPE: PRT
<213> ORGANISM: Artificial Sequence
<220> FEATURE:

<223> OTHER INFORMATION: fluorescent fusion protein

<400> SEQUENCE: 4

```
Met Ala Ser Trp Gly Ser Pro Lys Lys Arg Lys Val Leu Val Pro
  1               5                  10                  15

Val Ala Thr Met Ser Lys Gly Glu Glu Leu Phe Thr Gly Val Val Pro
             20                  25                  30

Ile Leu Val Glu Leu Asp Gly Asp Val Asn Gly His Lys Phe Ser Val
             35                  40                  45

Ser Gly Glu Gly Glu Gly Asp Ala Thr Tyr Gly Lys Leu Thr Leu Lys
 50                  55                  60

Phe Ile Cys Thr Thr Gly Lys Leu Pro Val Pro Trp Pro Thr Leu Val
 65                  70                  75                  80

Thr Thr Phe Gly Tyr Gly Leu Gln Cys Phe Ala Arg Tyr Pro Asp His
                 85                  90                  95

Met Lys Gln His Asp Phe Phe Lys Ser Ala Met Pro Glu Gly Tyr Val
                100                 105                 110

Gln Glu Arg Thr Ile Phe Phe Lys Asp Asp Gly Asn Tyr Lys Thr Arg
            115                 120                 125

Ala Glu Val Lys Phe Glu Gly Asp Thr Leu Val Asn Arg Ile Glu Leu
        130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Asp
            180                 185                 190

Gly Ser Val Gln Leu Ala Asp His Tyr Gln Gln Asn Thr Pro Ile Gly
        195                 200                 205

Asp Gly Pro Val Leu Leu Pro Asp Asn His Tyr Leu Ser Tyr Gln Ser
210                 215                 220

Ala Leu Ser Lys Asp Pro Asn Glu Lys Arg Asp His Met Val Leu Leu
225                 230                 235                 240

Glu Phe Val Thr Ala Ala Gly Ile Thr Leu Gly Met Asp Glu Leu Tyr
                245                 250                 255

Lys Gly Glu Gly Gln Gly Gln Gly Pro Gly Arg Gly Tyr Ala
            260                 265                 270

Tyr Arg Ser Met Phe Glu Ala Arg Leu Val Gln Gly Ser Ile Leu Lys
        275                 280                 285

Lys Val Leu Glu Ala Leu Lys Asp Leu Ile Asn Glu Ala Cys Trp Asp
    290                 295                 300

Ile Ser Ser Ser Gly Val Asn Leu Gln Ser Met Asp Ser Ser His Val
305                 310                 315                 320

Ser Leu Val Gln Leu Thr Leu Arg Ser Glu Gly Phe Asp Thr Tyr Arg
                325                 330                 335

Cys Asp Arg Asn Leu Ala Met Gly Val Asn Leu Thr Ser Met Ser Lys
            340                 345                 350

Ile Leu Lys Cys Ala Gly Asn Glu Asp Ile Ile Thr Leu Arg Ala Glu
        355                 360                 365

Asp Asn Ala Asp Thr Leu Ala Leu Val Phe Glu Ala Pro Asn Gln Glu
370                 375                 380

Lys Val Ser Asp Tyr Glu Met Lys Leu Met Asp Leu Asp Val Glu Gln
385                 390                 395                 400
```

```
Leu Gly Ile Pro Glu Gln Glu Tyr Ser Cys Val Val Lys Met Pro Ser
            405                 410                 415
Gly Glu Phe Ala Arg Ile Cys Arg Asp Leu Ser His Ile Gly Asp Ala
        420                 425                 430
Val Val Ile Ser Cys Ala Lys Asp Gly Val Lys Phe Ser Ala Ser Gly
    435                 440                 445
Glu Leu Gly Asn Gly Asn Ile Lys Leu Ser Gln Thr Ser Asn Val Asp
450                 455                 460
Lys Glu Glu Glu Ala Val Thr Ile Glu Met Asn Glu Pro Val Gln Leu
465                 470                 475                 480
Thr Phe Ala Leu Arg Tyr Leu Asn Phe Phe Thr Lys Ala Thr Pro Leu
                485                 490                 495
Ser Ser Thr Val Thr Leu Ser Met Ser Ala Asp Val Pro Leu Val Val
                500                 505                 510
Glu Tyr Lys Ile Ala Asp Met Gly His Leu Lys Tyr Tyr Leu Ala Pro
            515                 520                 525
Lys Ile Glu Asp Glu Glu Gly Ser
530                 535

<210> SEQ ID NO 5
<211> LENGTH: 1809
<212> TYPE: DNA
<213> ORGANISM: Artificial Sequence
<220> FEATURE:
<223> OTHER INFORMATION: expression vector

<400> SEQUENCE: 5
ctctcctcta gcggcgcacc tccagcagat tttccgtccc cacggaagag ctctggagac    60
agtggaggac ccagcacacc gtcagcatct ccactccctg tagtcacaga ccacgccatg   120
acaaatgatg tcacctggag cgaggcctct tcgcctgatg agaggacact cacctttgct   180
gaaagatggc aattatcttc acctgatgga gtagatacag atgatgattt accaaaatcg   240
cgagcatcca aaagaacctg tggtgtgaat gatgatgaaa gtccaagcaa aatttttatg   300
gtgggagaat ctccacaagt gtcttccaga cttcagaatt tgagactgaa taatttaatt   360
cccaggcaac ttttcaagcc caccgataat caagaaactc ggggtaccgc caccatggtg   420
gcctcctccg aggacgtcat caaagagttc atgcgcttca aggtgcgcat ggagggctcc   480
gtgaacggcc acgagttcga gatcgagggc gagggcgagg ccgcccccta cgagggcacc   540
cagaccgcca gctgaaggt gaccaagggc ggccccctgc cttcgcctg gacatcctg    600
tccccccagt ccagtacgg ctccaaggcg tacgtgaagc accccgccga catccccgac   660
tacaagaagc tgtccttccc cgagggcttc aagtgggagc gcgtgatgaa cttcgaggac   720
ggcggcgtgg tgaccgtgac ccaggactcc tccctgcagg acggcacgct gatctacaag   780
gtgaagttcc gcggcaccaa cttccccccc gacggccccg taatgcagaa gaagaccatg   840
ggctgggagg cctccaccga gcgcctgtac cccgcgacg gcgtgctgaa gggcgagatc   900
caccaggccc tgaagctgaa ggacggcggc cactacctgg tggagttcaa gaccatctac   960
atggccaaga agcccgtgca gctgcccggc tactactacg tggacaccaa gctggacatc  1020
acctcccaca cgaggactac accatcgtg aacagtacg agcgctccga gggccgccac  1080
cacctgttcc tggggcatgg caccggcagc accggcagcg cagctccgg caccgcctcc  1140
tccgaggacg tcatcaaaga gttcatgcgc ttcaaggtgc gcatggaggg ctccgtgaac  1200
ggccacgagt tcgagatcga gggcgagggc gagggccgcc cctacgaggg cacccagacc  1260
```

```
gccaagctga aggtgaccaa gggcggcccc ctgcccttcg cctgggacat cctgtccccc    1320
cagttccagt acggctccaa ggcgtacgtg aagcaccccg ccgacatccc cgactacaag    1380
aagctgtcct tccccgaggg cttcaagtgg gagcgcgtga tgaacttcga ggacggcggc    1440
gtggtgaccg tgacccagga ctcctccctg caggacggca cgctgatcta caaggtgaag    1500
ttccgcggca ccaacttccc ccccgacggc cccgtaatgc agaagaagac catgggctgg    1560
gaggcctcca ccgagcgcct gtaccccgc  gacggcgtgc tgaagggcga gatccaccag    1620
gccctgaagc tgaaggacgg cggccactac ctggtggagt tcaagaccat ctacatggcc    1680
aagaagcccg tgcagctgcc cggctactac tacgtggaca ccaagctgga catcacctcc    1740
cacaacgagg actacaccat cgtggaacag tacgagcgct ccgagggccg ccaccacctg    1800
ttcctgtag                                                            1809
```

<210> SEQ ID NO 6
<211> LENGTH: 602
<212> TYPE: PRT
<213> ORGANISM: Artificial Sequence
<220> FEATURE:
<223> OTHER INFORMATION: fluorescent fusion protein

<400> SEQUENCE: 6

```
Leu Ser Ser Ser Gly Ala Pro Pro Ala Asp Phe Pro Ser Pro Arg Lys
 1               5                  10                  15

Ser Ser Gly Asp Ser Gly Gly Pro Ser Thr Pro Ser Ala Ser Pro Leu
            20                  25                  30

Pro Val Val Thr Asp His Ala Met Thr Asn Asp Val Thr Trp Ser Glu
        35                  40                  45

Ala Ser Ser Pro Asp Glu Arg Thr Leu Thr Phe Ala Glu Arg Trp Gln
    50                  55                  60

Leu Ser Ser Pro Asp Gly Val Asp Thr Asp Asp Leu Pro Lys Ser
65                  70                  75                  80

Arg Ala Ser Lys Arg Thr Cys Gly Val Asn Asp Asp Glu Ser Pro Ser
                85                  90                  95

Lys Ile Phe Met Val Gly Glu Ser Pro Gln Val Ser Ser Arg Leu Gln
            100                 105                 110

Asn Leu Arg Leu Asn Asn Leu Ile Pro Arg Gln Leu Phe Lys Pro Thr
        115                 120                 125

Asp Asn Gln Glu Thr Arg Gly Thr Ala Thr Met Val Ala Ser Ser Glu
    130                 135                 140

Asp Val Ile Lys Glu Phe Met Arg Phe Lys Val Arg Met Glu Gly Ser
145                 150                 155                 160

Val Asn Gly His Glu Phe Glu Ile Glu Gly Glu Gly Glu Gly Arg Pro
                165                 170                 175

Tyr Glu Gly Thr Gln Thr Ala Lys Leu Lys Val Thr Lys Gly Gly Pro
            180                 185                 190

Leu Pro Phe Ala Trp Asp Ile Leu Ser Pro Gln Phe Gln Tyr Gly Ser
        195                 200                 205

Lys Ala Tyr Val Lys His Pro Ala Asp Ile Pro Asp Tyr Lys Lys Leu
    210                 215                 220

Ser Phe Pro Glu Gly Phe Lys Trp Glu Arg Val Met Asn Phe Glu Asp
225                 230                 235                 240

Gly Gly Val Val Thr Val Thr Gln Asp Ser Ser Leu Gln Asp Gly Thr
                245                 250                 255

Leu Ile Tyr Lys Val Lys Phe Arg Gly Thr Asn Phe Pro Pro Asp Gly
```

```
                260                 265                 270
Pro Val Met Gln Lys Lys Thr Met Gly Trp Glu Ala Ser Thr Glu Arg
            275                 280                 285
Leu Tyr Pro Arg Asp Gly Val Leu Lys Gly Glu Ile His Gln Ala Leu
        290                 295                 300
Lys Leu Lys Asp Gly Gly His Tyr Leu Val Glu Phe Lys Thr Ile Tyr
305                 310                 315                 320
Met Ala Lys Lys Pro Val Gln Leu Pro Gly Tyr Tyr Val Asp Thr
            325                 330                 335
Lys Leu Asp Ile Thr Ser His Asn Glu Asp Tyr Thr Ile Val Glu Gln
        340                 345                 350
Tyr Glu Arg Ser Glu Gly Arg His His Leu Phe Leu Gly His Gly Thr
            355                 360                 365
Gly Ser Thr Gly Ser Gly Ser Ser Gly Thr Ala Ser Ser Glu Asp Val
        370                 375                 380
Ile Lys Glu Phe Met Arg Phe Lys Val Arg Met Glu Gly Ser Val Asn
385                 390                 395                 400
Gly His Glu Phe Glu Ile Glu Gly Glu Gly Glu Gly Arg Pro Tyr Glu
            405                 410                 415
Gly Thr Gln Thr Ala Lys Leu Lys Val Thr Lys Gly Gly Pro Leu Pro
            420                 425                 430
Phe Ala Trp Asp Ile Leu Ser Pro Gln Phe Gln Tyr Gly Ser Lys Ala
        435                 440                 445
Tyr Val Lys His Pro Ala Asp Ile Pro Asp Tyr Lys Lys Leu Ser Phe
            450                 455                 460
Pro Glu Gly Phe Lys Trp Glu Arg Val Met Asn Phe Glu Asp Gly Gly
465                 470                 475                 480
Val Val Thr Val Thr Gln Asp Ser Ser Leu Gln Asp Gly Thr Leu Ile
            485                 490                 495
Tyr Lys Val Lys Phe Arg Gly Thr Asn Phe Pro Pro Asp Gly Pro Val
        500                 505                 510
Met Gln Lys Lys Thr Met Gly Trp Glu Ala Ser Thr Glu Arg Leu Tyr
        515                 520                 525
Pro Arg Asp Gly Val Leu Lys Gly Glu Ile His Gln Ala Leu Lys Leu
530                 535                 540
Lys Asp Gly Gly His Tyr Leu Val Glu Phe Lys Thr Ile Tyr Met Ala
545                 550                 555                 560
Lys Lys Pro Val Gln Leu Pro Gly Tyr Tyr Val Asp Thr Lys Leu
            565                 570                 575
Asp Ile Thr Ser His Asn Glu Asp Tyr Thr Ile Val Glu Gln Tyr Glu
        580                 585                 590
Arg Ser Glu Gly Arg His His Leu Phe Leu
        595                 600

<210> SEQ ID NO 7
<211> LENGTH: 28
<212> TYPE: PRT
<213> ORGANISM: Artificial Sequence
<220> FEATURE:
<223> OTHER INFORMATION: plasma membrane targeting sequence

<400> SEQUENCE: 7

Met Glu Lys Lys Ser Lys Pro Lys Asn Ser Val Trp Lys Arg Leu Lys
1               5                   10                  15

Ser Pro Phe Arg Lys Lys Lys Asp Ser Val Thr Gly
```

```
          20              25

<210> SEQ ID NO 8
<211> LENGTH: 21
<212> TYPE: PRT
<213> ORGANISM: Artificial Sequence
<220> FEATURE:
<223> OTHER INFORMATION: plasma membrane targeting sequence

<400> SEQUENCE: 8

Lys Lys Ser Lys Pro Lys Asn Ser Val Trp Lys Arg Leu Lys Ser Pro
 1               5                  10                  15

Phe Arg Lys Lys Lys
            20

<210> SEQ ID NO 9
<211> LENGTH: 21
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: VARIANT
<222> LOCATION: 3, 7, 8, 15
<223> OTHER INFORMATION: Xaa = Any Amino Acid

<400> SEQUENCE: 9

Lys Lys Xaa Lys Pro Lys Xaa Xaa Val Trp Lys Arg Leu Lys Xaa Pro
 1               5                  10                  15

Phe Arg Lys Lys Lys
            20

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
gccggctagc atggagaaaa aatctaagcc caa                            33

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ggccaccggt ccagttactg aatctttctt ct                             32

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
cccaagcttg ggctctcctc tagcggcgca                                30

<210> SEQ ID NO 13
<211> LENGTH: 34
<212> TYPE: DNA
<213> ORGANISM: Artificial Sequence
```

```
<220> FEATURE:
<223> OTHER INFORMATION: primer

<400> SEQUENCE: 13
cggggtaccc cgagtttctt gattatcggt gggc                              34

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
gcgtaatacg actcactata ggatggcaca gcagctcgcc cg                     42

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
gcgtaatacg actcactata ggtcagtcac tgacaggtgt tt                     42

<210> SEQ ID NO 16
<211> LENGTH: 927
<212> TYPE: DNA
<213> ORGANISM: Artificial Sequence
<220> FEATURE:
<223> OTHER INFORMATION: fluorescent fusion protein coding sequence

<400> SEQUENCE: 16
atggagaaaa aatctaagcc caaaaacagt gtatggaaga ggctaaaatc accattccgg   60
aagaagaaag attcagtaac tggaccggtc gccaccatgg tgagcaaggg cgaggagctg  120
ttcaccgggg tggtgcccat cctggtcgag ctggacggcg acgtaaacgg ccacaagttc  180
agcgtgtccg gcgagggcga gggcgatgcc acctacggca agctgaccct gaagttcatc  240
tgcaccaccg gcaagctgcc cgtgccctgg cccaccctcg tgaccacctt cggctacggc  300
ctgcagtgct tcgcccgcta ccccgaccac atgaagcagc acgacttctt caagtccgcc  360
atgcccgaag gctacgtcca ggagcgcacc atcttcttca aggacgacgg caactacaag  420
acccgcgccg aggtgaagtt cgagggcgac accctggtga accgcatcga gctgaagggc  480
atcgacttca aggaggacgg caacatcctg ggcacaagc tggagtacaa ctacaacagc  540
cacaacgtct atatcatggc cgacaagcag aagaacggca tcaaggtgaa cttcaagatc  600
cgccacaaca tcgaggacgg cagcgtgcag ctcgccgacc actaccagca gaacaccccc  660
atcggcgacg gccccgtgct gctgcccgac aaccactacc tgagctacca gtccgccctg  720
agcaaagacc ccaacgagaa gcgcgatcac atggtcctgc tggagttcgt gaccgccgcc  780
gggatcactc tcggcatgga cgagctgtac aagtccggac tcagatctcg agctgatcca  840
aaaagaaga gaaaggtaga tccaaaaaag aagagaaagg tagatccaaa aagaagaga  900
aaggtaggat ccaccggatc tagataa                                      927

<210> SEQ ID NO 17
<211> LENGTH: 21
<212> TYPE: PRT
<213> ORGANISM: Artificial Sequence
<220> FEATURE:
```

```
-continued

<223> OTHER INFORMATION: targeting sequence
<220> FEATURE:
<221> NAME/KEY: VARIANT
<222> LOCATION: 1,2,4,6,10,11,12,14,18,19,20,21
<223> OTHER INFORMATION: Xaa = lysine, tryptaphan or arginine
<220> FEATURE:
<221> NAME/KEY: VARIANT
<222> LOCATION: 3, 5, 7, 8, 9, 13, 15, 16, 17
<223> OTHER INFORMATION: Xaa = Any Amino Acid

<400> SEQUENCE: 17

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
             20
```